United States Patent
Fischkoff et al.

(10) Patent No.: US 11,180,731 B2
(45) Date of Patent: Nov. 23, 2021

(54) METHODS OF TREATING ACUTE MYELOID LEUKEMIA AND MULTIPLE MYELOMA USING NATURAL KILLER CELLS

(71) Applicant: Celularity Inc., Florham Park, NJ (US)

(72) Inventors: Steven A. Fischkoff, Short Hills, NJ (US); Uri Herzberg, Bridgewater, NJ (US); Lin Kang, Basking Ridge, NJ (US); Brian Murphy, Livingston, NJ (US); Andrea Nordberg, Providence, NJ (US); Vanessa Voskinarian-Berse, Millington, NJ (US); Keith Wilson, Mountainside, NJ (US); Xiaokui Zhang, Martinsville, NJ (US); Han Myint, Bethesda, MD (US); Mohamad Hussein, Melbourne Beach, FL (US); Robert J Hariri, Bernardsville, NJ (US)

(73) Assignee: Celularity Inc., Florham Park, NJ (US)

( * ) Notice: Subject to any disclaimer, the term of this patent is extended or adjusted under 35 U.S.C. 154(b) by 0 days.

(21) Appl. No.: 16/099,676

(22) PCT Filed: May 5, 2017

(86) PCT No.: PCT/US2017/031255
§ 371 (c)(1),
(2) Date: Nov. 7, 2018

(87) PCT Pub. No.: WO2017/196657
PCT Pub. Date: Nov. 16, 2017

(65) Prior Publication Data
US 2019/0153389 A1    May 23, 2019

Related U.S. Application Data

(60) Provisional application No. 62/415,954, filed on Nov. 1, 2016, provisional application No. 62/415,918, filed on Nov. 1, 2016, provisional application No. 62/333,186, filed on May 7, 2016, provisional application No. 62/333,187, filed on May 7, 2016.

(51) Int. Cl.
| | |
|---|---|
| *A61P 35/02* | (2006.01) |
| *A61K 38/20* | (2006.01) |
| *C12N 5/0783* | (2010.01) |
| *A61K 35/17* | (2015.01) |
| *A61P 35/00* | (2006.01) |

(52) U.S. Cl.
CPC ............ *C12N 5/0638* (2013.01); *A61K 35/17* (2013.01); *A61K 38/2013* (2013.01); *A61P 35/00* (2018.01); *A61P 35/02* (2018.01); *C12N 5/0646* (2013.01); *C12N 2501/145* (2013.01); *C12N 2501/22* (2013.01); *C12N 2501/2302* (2013.01); *C12N 2501/2306* (2013.01); *C12N 2501/2307* (2013.01); *C12N 2501/2315* (2013.01); *C12N 2501/26* (2013.01); *C12N 2501/999* (2013.01); *C12N 2506/11* (2013.01)

(58) Field of Classification Search
None
See application file for complete search history.

(56) References Cited

U.S. PATENT DOCUMENTS

2015/0225697 A1*  8/2015  Law .................... C12N 5/0646
                                              424/93.71

FOREIGN PATENT DOCUMENTS

| WO | 2012128622 A1 | 9/2012 |
| WO | 2013119118 A1 | 8/2013 |
| WO | 2014028453 A2 | 2/2014 |
| WO | 2015174928    | 11/2015 |

OTHER PUBLICATIONS

Roeven et al., Stem Cells Dev. Dec. 15, 2015;24(24):2886-98 (Year: 2015).*
Hughes et al., Cell Rep, 2014, 8:150-162 (Year: 2014).*
Baer et al., "Low-dose interleukin-2 immunotherapy does not improve outcome of patients age 60 years and older with acute myeloid leukemia in first complete remission", J Clin Oncol, (Jun. 30, 2008), vol. 26, No. 30, pp. 4934-4939, XP055436488.
Office Action dated Dec. 7, 2020 for U.S. Appl. No. 16/099,676 (pp. 1-9).
Roeven et al., Stem Cells Dev. Dec. 1, 20155;24(24):2886-98 (Year: 2015).
Notice of Allowance dated Jul. 8, 2021 for U.S. Appl. No. 16/099,676 (pp. 1-9).

* cited by examiner

*Primary Examiner* — Daniel C Gamett
(74) *Attorney, Agent, or Firm* — Geoffry T. Knudsen

(57) ABSTRACT

Provided herein are methods of treating acute myeloid leukemia (AML) and multiple myeloma (MM) by administering an effective amount of a cell population comprising natural killer cells, wherein the cell population comprising natural killer cells is produced by a three-stage method comprising culturing a population of hematopoietic stem or progenitor cells in media comprising stem cell mobilizing factors, e.g., three-stage methods of producing NK cells in media comprising stem cell mobilizing factors starting with hematopoietic stem or progenitor cells from cells of the placenta, for example, from placental perfusate (e.g., human placental perfusate) or other tissues, for example, umbilical cord blood or peripheral blood. Further provided herein are methods of using the NK cells produced by the three-stage methods provided herein to suppress the proliferation of acute myeloid leukemia cells. In certain embodiments, the NK cells produced by the three-stage methods described herein are used in combination with IL-2.

18 Claims, No Drawings

METHODS OF TREATING ACUTE MYELOID LEUKEMIA AND MULTIPLE MYELOMA USING NATURAL KILLER CELLS

This application is the 35 USC § 371 national stage of international Application No. PCT/US2017/031255, filed May 5, 2017, which application claims the benefit of U.S. Provisional Application No. 62/333,186, filed May 7, 2016, U.S. Provisional Application No. 62/333,187, filed May 7, 2016, U.S. Provisional Application No. 62/415,918, filed Nov. 1, 2016, and U.S. Provisional Application No. 62/415,954, filed Nov. 1, 2016, each of which is hereby incorporated by reference in its entirety.

1. FIELD

Provided herein are methods of treating acute myeloid leukemia (AML) and multiple myeloma (MM) by administering an effective amount of a cell population comprising natural killer cells, wherein the cell population comprising natural killer cells is produced by a three-stage method comprising culturing a population of hematopoietic stem or progenitor cells in media comprising stem cell mobilizing factors, e.g., three-stage methods of producing NK cells in media comprising stem cell mobilizing factors starting with hematopoietic stem or progenitor cells from cells of the placenta, for example, from placental perfusate (e.g., human placental perfusate) or other tissues, for example, umbilical cord blood or peripheral blood. Further provided herein are methods of using the NK cells produced by the three-stage methods provided herein to suppress the proliferation of acute myeloid leukemia cells. In certain embodiments, the NK cells produced by the three-stage methods described herein are used in combination with IL-2.

2. BACKGROUND

Natural killer (NK) cells are cytotoxic lymphocytes that constitute a major component of the innate immune system. NK cells are activated in response to interferons or macrophage-derived cytokines. The cytotoxic activity of NK cells is largely regulated by two types of surface receptors, which may be considered "activating receptors" or "inhibitory receptors," although some receptors, e.g., CD94 and 2B4 (CD244), can work either way depending on ligand interactions.

Among other activities, NK cells play a role in the host rejection of tumors and have been shown capable of killing virus-infected cells. Natural killer cells can become activated by cells lacking, or displaying reduced levels of, major histocompatibility complex (MHC) proteins. Cancer cells with altered or reduced level of self-class I MHC expression result in induction of NK cell sensitivity. Activated and expanded NK cells, and in some cases LAK cells, from peripheral blood have been used in both ex vivo therapy and in vivo treatment of patients having advanced cancer, with some success against bone marrow related diseases, such as leukemia; breast cancer; and certain types of lymphoma.

In spite of the advantageous properties of NK cells in killing tumor cells and virus-infected cells, they remain difficult to apply in immunotherapy, primarily due to the difficulty in maintaining their tumor-targeting and tumoricidal capabilities during culture and expansion. Thus, there is a need in the art to develop an efficient method to produce and expand natural killer cells that retain tumoricidal functions.

3. SUMMARY

Provided herein are methods of treatment of an individual having acute myeloid leukemia using the NK cells produced using the methods described herein, e.g., NK cell populations produced using the three-stage method described herein. The methods of treatment provided herein can be part of an anticancer therapy regimen that includes administration of IL-2. In certain embodiments, the IL-2 is human IL-2. In certain embodiments, the IL-2 is recombinant human IL-2 (rhIL-2).

Further provided herein are methods of suppressing the proliferation of acute myeloid leukemia cells, comprising bringing NK cells produced using the methods described herein, e.g., NK cell populations produced using the three-stage method described herein, into proximity with the acute myeloid leukemia cells, e.g., contacting the acute myeloid leukemia cells with NK cells produced using the methods described herein. In certain embodiments, provided herein is a method of suppressing the proliferation of acute myeloid leukemia cells, comprising bringing NK cells produced using the methods described herein, e.g., NK cell populations produced using the three-stage method described herein, into proximity with the acute myeloid leukemia cells, e.g., contacting the acute myeloid leukemia cells with NK cells produced using the methods described herein, further comprising bringing IL-2 into proximity with the NK cells and/or the acute myeloid leukemia cells, e.g., contacting the NK cells and/or acute myeloid leukemia cells with IL-2. In specific embodiments, the IL-2 is rhIL-2.

Provided herein are methods of treatment of an individual having multiple myeloma using the NK cells produced using the methods described herein, e.g., NK cell populations produced using the three-stage method described herein. The methods of treatment provided herein can be part of an anticancer therapy regimen that includes administration of IL-2. In certain embodiments, the IL-2 is human IL-2. In certain embodiments, the IL-2 is recombinant human IL-2 (rhIL-2).

Further provided herein are methods of suppressing the proliferation of multiple myeloma cells, comprising bringing NK cells produced using the methods described herein, e.g., NK cell populations produced using the three-stage method described herein, into proximity with the multiple myeloma cells, e.g., contacting the multiple myeloma cells with NK cells produced using the methods described herein. In certain embodiments, provided herein is a method of suppressing the proliferation of multiple myeloma cells, comprising bringing NK cells produced using the methods described herein, e.g., NK cell populations produced using the three-stage method described herein, into proximity with the multiple myeloma cells, e.g., contacting the multiple myeloma cells with NK cells produced using the methods described herein, further comprising bringing IL-2 into proximity with the NK cells and/or the multiple myeloma cells, e.g., contacting the NK cells and/or multiple myeloma cells with IL-2. In specific embodiments, the IL-2 is rhIL-2.

Provided herein are methods of expanding and differentiating cells, for example, hematopoietic cells, such as hematopoietic stem cells, e.g., $CD34^+$ hematopoietic stem cells, to produce natural killer (NK) cells.

In one aspect, provided herein are methods of producing NK cell populations that comprise three stages as described herein (and referred to herein as the "three-stage method"). Natural killer cells produced by the three-stage methods provided herein are referred to herein as "NK cells produced by the three-stage method." In certain embodiments, said method does not comprise any fourth or intermediate step in which the cells are contacted (or cultured).

In one aspect, provided herein is a method of producing NK cells comprising culturing hematopoietic stem cells or progenitor cells, e.g., CD34+ stem cells or progenitor cells, in a first medium comprising a stem cell mobilizing agent and thrombopoietin (Tpo) to produce a first population of cells, subsequently culturing said first population of cells in a second medium comprising a stem cell mobilizing agent and interleukin-15 (IL-15), and lacking Tpo, to produce a second population of cells, and subsequently culturing said second population of cells in a third medium comprising IL-2 and IL-15, and lacking a stem cell mobilizing agent and low-molecular weight heparin (LMWH), to produce a third population of cells, wherein the third population of cells comprises natural killer cells that are CD56+, CD3−, and wherein at least 70%, for example 80%, of the natural killer cells are viable. In certain embodiments, such natural killer cells comprise natural killer cells that are CD16−. In certain embodiments, such natural killer cells comprise natural killer cells that are CD94+. In certain embodiments, such natural killer cells comprise natural killer cells that are CD94+ or CD16+. In certain embodiments, such natural killer cells comprise natural killer cells that are CD94− or CD16−. In certain embodiments, such natural killer cells comprise natural killer cells that are CD94+ and CD16+. In certain embodiments, such natural killer cells comprise natural killer cells that are CD94− and CD16−. In certain embodiments, at least one, two, or all three of said first medium, second medium, and third medium are not the medium GBGM®. In certain embodiments, the third medium lacks added desulphated glycosaminoglycans. In certain embodiments, the third medium lacks desulphated glycosaminoglycans.

In certain embodiments, said hematopoietic stem or progenitor cells are mammalian cells. In specific embodiments, said hematopoietic stem or progenitor cells are human cells. In specific embodiments, said hematopoietic stem or progenitor cells are primate cells. In specific embodiments, said hematopoietic stem or progenitor cells are canine cells. In specific embodiments, said hematopoietic stem or progenitor cells are rodent cells.

In certain aspects, the hematopoietic stem cells or progenitor cells cultured in the first medium are CD34+ stem cells or progenitor cells. In certain aspects, the hematopoietic stem cells or progenitor cells are placental hematopoietic stem cells or progenitor cells. In certain aspects, the placental hematopoietic stem cells or progenitor cells are obtained from, or obtainable from placental perfusate (e.g. obtained from or obtainable from isolated nucleated cells from placental perfusate). In certain aspects, said hematopoietic stem or progenitor cells are obtained from, or obtainable from, umbilical cord blood. In certain aspects, said hematopoietic stem or progenitor cells are fetal liver cells. In certain aspects, said hematopoietic stem or progenitor cells are mobilized peripheral blood cells. In certain aspects, said hematopoietic stem or progenitor cells are bone marrow cells.

In certain aspects, said first medium used in the three-stage method comprises a stem cell mobilizing agent and thrombopoietin (Tpo). In certain aspects, the first medium used in the three-stage method comprises, in addition to a stem cell mobilizing agent and Tpo, one or more of Low Molecular Weight Heparin (LMWH), Flt-3 Ligand (Flt-3L), stem cell factor (SCF), IL-6, IL-7, granulocyte colony-stimulating factor (G-CSF), or granulocyte-macrophage-stimulating factor (GM-CSF). In certain aspects, said first medium does not comprise added LMWH. In certain aspects, said first medium does not comprise added desulphated glycosaminoglycans. In certain aspects, said first medium does not comprise LMWH. In certain aspects, said first medium does not comprise desulphated glycosaminoglycans. In certain aspects, the first medium used in the three-stage method comprises, in addition to a stem cell mobilizing agent and Tpo, each of LMWH, Flt-3L, SCF, IL-6, IL-7, G-CSF, and GM-CSF. In certain aspects, the first medium used in the three-stage method comprises, in addition to a stem cell mobilizing agent and Tpo, each of Flt-3L, SCF, IL-6, IL-7, G-CSF, and GM-CSF. In certain aspects, said Tpo is present in the first medium at a concentration of from 1 ng/mL to 100 ng/mL, from 1 ng/mL to 50 ng/mL, from 20 ng/mL to 30 ng/mL, or about 25 ng/mL. In certain aspects, in the first medium, the LMWH is present at a concentration of from 1 U/mL to 10 U/mL; the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in the first medium, the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in the first medium, the LMWH is present at a concentration of from 4 U/mL to 5 U/mL; the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the first medium, the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the first medium, the LMWH is present at a concentration of about 4.5 U/mL; the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain aspects, in the first medium, the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain embodiments, said first medium is not GBGM®.

In certain aspects, said second medium used in the three-stage method comprises a stem cell mobilizing agent and interleukin-15 (IL-15), and lacks Tpo. In certain aspects, the second medium used in the three-stage method comprises, in addition to a stem cell mobilizing agent and IL-15, one or more of LMWH, Flt-3, SCF, IL-6, IL-7, G-CSF, and GM-CSF. In certain aspects, the second medium does not comprise added LMWH. In certain aspects, the second medium does not comprise added desulphated glycosaminoglycans. In certain aspects, the second medium does not comprise LMWH. In certain aspects, the second medium does not comprise desulphated glycosaminoglycans. In certain aspects, the second medium used in the three-stage method comprises, in addition to a stem cell mobilizing agent and IL-15, each of LMWH, Flt-3, SCF, IL-6, IL-7, G-CSF, and GM-CSF. In certain aspects, the second medium used in the three-stage method comprises, in addition to a stem cell mobilizing agent and IL-15, each of Flt-3, SCF, IL-6, IL-7, G-CSF, and GM-CSF. In certain aspects, said IL-15 is present in said second medium at a concentration of from 1 ng/mL to 50 ng/mL, from 10 ng/mL to 30 ng/mL, or about 20 ng/mL. In certain aspects, in said second medium, the LMWH is present at a concentration of from 1 U/mL to 10 U/mL; the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in the second medium, the LMWH is present in the second medium at a concentration of from 4 U/mL to 5 U/mL; the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the LMWH is present in the second medium at a concentration of from 4 U/mL to 5 U/mL; the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the LMWH is present in the second medium at a concentration of about 4.5 U/mL; the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain aspects, in the second medium, the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain embodiments, said second medium is not GBGM®.

In certain aspects, the stem cell mobilizing factor present in said first medium, said second medium, or said first and second media, is an aryl hydrocarbon receptor inhibitor, e.g., an aryl hydrocarbon receptor antagonist. In certain aspects, said aryl hydrocarbon receptor inhibitor is resveratrol. Is certain aspects, said aryl hydrocarbon receptor inhibitor is compound of the formula

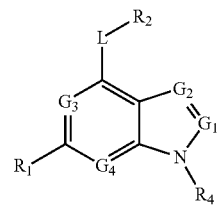

in which:

$G_1$ is selected from N and $CR_3$;

$G_2$, $G_3$ and $G_4$ are independently selected from CH and N; with the proviso that at least 1 of $G_3$ and $G_4$ is N; with the proviso that $G_1$ and $G_2$ are not both N;

L is selected from —$NR_{5a}(CH_2)_{0-3}$—, —$NR_{5a}CH(C(O)OCH_3)CH_2$—, —$NR_{5a}(CH_2)_2NR_{5b}$—, —$NR_{5a}(CH_2)_2S$—, —$NR_{5a}CH_2CH(CH_3)CH_2$—, —$NR_{5a}CH_2CH(OH)$— and —$NR_{5a}CH(CH_3)CH_2$—; wherein $R_{5a}$ and $R_{5b}$ are independently selected from hydrogen and $C_{1-4}$alkyl;

$R_1$ is selected from hydrogen, phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl and thiazolyl; wherein said phenyl, thiophenyl, furanyl, 1H-benzoimidazolyl, isoquinolinyl, 1H-imidazopyridinyl, benzothiophenyl, pyrimidinyl, 1H-pyrazolyl, pyridinyl, 1H-imidazolyl, pyrrolidinyl, pyrazinyl, pyridazinyl, 1H-pyrrolyl or thiazolyl of $R_1$ can be optionally substituted by 1 to 3 radicals independently selected from cyano, hydroxy, $C_{1-4}$alkyl, $C_{1-4}$alkoxy, halo, halo-substituted-$C_{1-4}$alkyl, halo-substituted-$C_{1-4}$alkoxy, hydroxy, amino, —C(O)$R_{8a}$, —S(O)$_{0-2}R_{8a}$, —C(O)O$R_{8a}$ and —C(O)N$R_{8a}R_{8b}$; wherein $R_{8a}$ and $R_{8b}$ are independently selected from hydrogen and $C_{1-4}$alkyl; with the proviso that $R_1$ and $R_3$ are not both hydrogen;

$R_2$ is selected from —S(O)$_2$N$R_{6a}R_{6b}$, —N$R_{9a}$C(O)$R_{9b}$, —N$R_{6a}$C(O)N$R_{6b}R_{6c}$, phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl and 1H-indazolyl; wherein $R_{6a}$, $R_{6b}$ and $R_{6c}$ are independently selected from hydrogen and $C_{1-4}$ alkyl; wherein said phenyl, 1H-pyrrolopyridin-3-yl, 1H-indolyl, thiophenyl, pyridinyl, 1H-1,2,4-triazolyl, 2-oxoimidazolidinyl, 1H-pyrazolyl, 2-oxo-2,3-dihydro-1H-benzoimidazolyl or 1H-indazolyl of $R_2$ is optionally substituted with 1 to 3 radicals independently selected from hydroxy, halo, methyl, methoxy, amino, —O(CH$_2$)$_n$NR$_{7a}$R$_{7b}$, —S(O)$_2$NR$_{7a}$R$_{7b}$, —OS(O)$_2$NR$_{7a}$R$_{7b}$ and —NR$_{7a}$S(O)$_2$R$_{7b}$; wherein $R_{7a}$ and $R_{7b}$ are independently selected from hydrogen and $C_{1-4}$alkyl;

$R_3$ is selected from hydrogen, $C_{1-4}$alkyl and biphenyl; and
$R_4$ is selected from $C_{1-10}$alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentylphenyl)(phenyl)methyl and 1-(1-(2-oxo-6,9,12-trioxa-3-azatetradecan-14-yl)-1H-1,2,3-triazol-4-yl)ethyl; wherein said alkyl, cyclopropyl, cyclohexyl, 2-(2-oxopyrrolidin-1-yl)ethyl, oxetan-3-yl, oxetan-2-yl, benzhydryl, tetrahydro-2H-pyran-3-yl, tetrahydro-2H-pyran-4-yl, phenyl, tetrahydrofuran-3-yl, tetrahydrofuran-2-yl, benzyl, (4-pentylphenyl)(phenyl)methyl or 1-(1-(2-oxo-6,9,12-trioxa-3-azatetradecan-14-yl)-1H-1,2,3-triazol-4-yl)ethyl can be optionally substituted with 1 to 3 radicals independently selected from hydroxy, $C_{1-4}$alkyl and halo-substituted-$C_{1-4}$ alkyl; or a salt thereof.

In certain aspects, said aryl hydrocarbon receptor inhibitor is StemRegenin-1 (SR-1) (4-(2-(2-(benzo[b]thiophen-3-yl)-9-isopropyl-9H-purin-6-ylamino)ethyl)phenol). In certain aspects, said aryl hydrocarbon receptor inhibitor is the compound CH223191 (1-Methyl-N-[2-methyl-4-[2-(2-methylphenyl)diazenyl]phenyl-1H-pyrazole-5-carboxamide].

In certain aspects, the stem cell mobilizing factor present in said first medium, said second medium, or said first and second mediums is a pyrimido(4,5-b)indole derivative. In certain aspects, said pyrimido(4,5-b)indole derivative is one or more of:

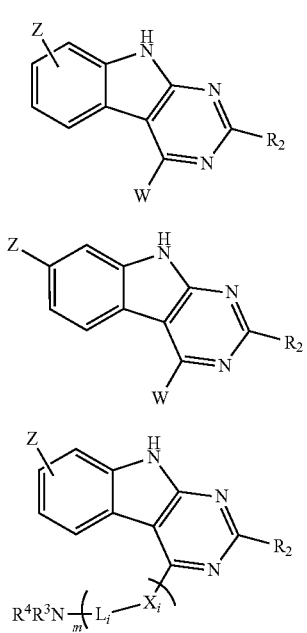

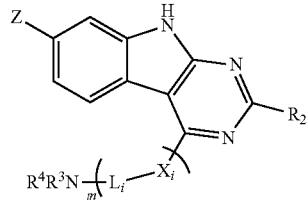

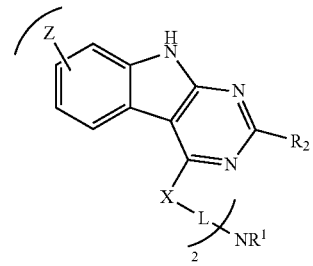

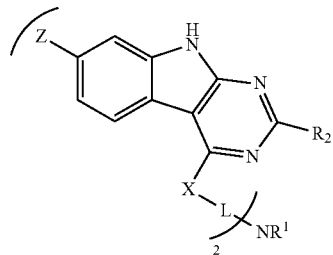

or a salt or a prodrug thereof, wherein:
Z is
1) —P(O) (OR<1>) (OR<1>),
2) —C(O)OR<1>,
3) —C(O)NHR<1>,
4) —C(O)N(R)R<1>,
5) —C(O)R<1>,
6) —CN,
7) —SR,
8) —S(O)2NH2,
9) —S(O)2NHR<1>,
10) —S(O)2N(R)R<1>,
11) —S(O)R<1>,
12) —S(O)2R<1>,
13) -L,
14) -benzyl optionally substituted with 1, 2 or 3 R<A> or R<1> substituents,
15) -L-heteroaryl optionally substituted with one or more R<A> or R<1> substituents attached on either or both the L and the heteroaryl groups,
16) -L-heterocyclyl optionally substituted with one or more R<A> or R<1> substituents attached on either one or both the L and the heterocyclyl groups, 17) -L-aryl optionally substituted with one or more R<A> or R<1> substituents attached on either or both the L and the heteroaryl groups,
18) -heteroaryl optionally substituted with one or more R<A> or R<1> substituents, or
19) -aryl optionally substituted with one or more R<A> or R<1> substituents,
and wherein each substituent is optionally attached to the L group if it is not already present, and wherein, when (R<1>) and R<1> are attached to a nitrogen atom, optionally they join together with the nitrogen atom to form a 3 to 7-membered ring which optionally includes one or more other heteroatom selected from N, O and S, optionally the is substituted with one or more R<1> or R<A>;

W is
1) —H,
2) -halogen,
3) —OR<1>,
4) -L-OH,
5) -L-OR<1>,
6) —SR<1>,
7) —CN,
8) —P(O)(OR<1>)(OR<1>),
9) —NHR<1>,
10) —N(R<1>)R<1>,
11) -L-NH2,
12) -L-NHR<1>,
13) -L-N(R<1>)R<1>,
14) -L-SR<1>,
15) -L-S(O)R<1>,
16) -L-S(O)2R<1>,
17) -L-P(O)(OR<1>)(OR<1>
18) —C(O)OR<1>,
19) —C(O)NH2,
20) —C(O)NHR<1>,
21) —C(O)N(R<1>)R<1>,
22) —NHC(O)R<1>,
23) —NR1C(O)R<1>, —NHC(O)OR<1>,
—NR1C(O)OR<1>,
—OC(O)NH2,
—OC(O)NHR<1>,
—OC(O)N(R)R<1>,
—OC(O)R<1>,
—C(O)R<1>,
—NHC(O)NH2,
—NHC(O)NHR<1>,
—NHC(O)N(R)R<1>,
—NR C(O)NH2,
—NR C(O)NHR<1>,
—NR C(O)N(R)R<1>,
—NHS(O)2R<1>,
—NR S(O)2R<1>,
—S(O)2NH2,
—S(O)2NHR<1>,
—S(O)2N(R)R<1>,
—S(O)R<1>,
—S(O)2R<1>,
—OS(O)2R1,
—S(O)2OR<1>,
-benzyl optionally substituted with 1, 2 or 3 R<A> or R<1> substituents,
-L-heteroaryl optionally substituted with one or more R<A> or R<1> substituents attached on either or both the L and the heteroaryl groups,
-L-heterocyclyl optionally substituted with one or more R<A> or R<1> substituents attached on either or both the L and the heterocyclyl groups,
-L-aryl optionally substituted with one or more R<A> or R<1> substituents attached on either or both the L and aryl groups,
-L-NR<1>(R<1>),
-L-)2 NR<1>,
-L-(N(R1)-L)n-N(R1)R1,  -L-(N(R<1>)-L)n-heteroaryl optionally substituted with one or more R<A> or R<1> substituents attached on either or both the L and heteroaryl groups,
-L-(N(R<1>)-L)n-heterocyclyl optionally substituted with one or more R<A> or R<1> substituents attached on either or both the L and heterocyclyl groups,
-L-(N(R<1>)-L)n-aryl optionally substituted with one or more R<A> or R<1> substituents attached on either or both the L and aryl groups,
—O-L-N(R)R<1>,
—O-L-heteroaryl optionally substituted with one or more R<A> or R<1> substituents attached on either or both the L and heteroaryl groups,
—O-L-heterocyclyl optionally substituted with one or more R<A> or R<1> substituents attached on either or both the L and heterocyclyl groups,
—O-L-aryl optionally substituted with one or more R<A> or R<1> substituents attached on either or both the L and aryl groups,
—O-L)2-NR<1>,
—O-L-(N(R)-L)n-N(R)R<1>,
—O-L-(N(R<1>)-L)n-heteroaryl optionally substituted with one or more R<A> or R<1> substituents attached on either or both the L and heteroaryl groups,
—O-L-(N(R<1>)-L)n-heterocyclyl optionally substituted with one or more R<A> or R<1> substituents attached on either or both the L and heterocyclyl groups,
—O-L-(N(R<1>)-L)n-aryl optionally substituted with one or more R<A> or R<1> substituents,
—S-L-heteroaryl optionally substituted with one or more R<A> or R<1> substituents,
—S-L-heterocyclyl optionally substituted with one or more R<A> or R<1> substituents,
—S-L-aryl optionally substituted with one or more R<A> or R<1> substituents attached on either or both the L and aryl groups,
—S-L)2 NR1,
—S-L-(N(R1)-L)"-N(R1)R1,
—S-L-(N(R<1>)-L)n-heteroaryl optionally substituted with one or more R<A> substituents, —S-L-(N(R<1>)-L)n-heterocyclyl optionally substituted with one or more R<A> substituents, —S-L-(N(R<1>)-L)n-aryl optionally substituted with one or more R<A> substituents,
—NR<1>(R<1>),
—(N(R1)-L)n-N(R1)R1,
—N(R1)L)2-NR1, 76) —(N(R1)-L)"-N(R1)RA,
77) —(N(R<1>)-L)n-heteroaryl optionally substituted with one or more R<A> or R<1> substituents,
78) —(N(R<1>)-L)n-heterocyclyl optionally substituted with one or more R<A> or R<1> substituents,
79) —(N(R<1>)-L)n-aryl optionally substituted with one or more R<A> or R<1> substituents,
80) -heteroaryl optionally substituted with one or more R<A> substituents, or
81) -aryl optionally substituted with one or more R<A> substituents,
and wherein each substituent is optionally attached to the L group if it is not already present, and wherein when two R<1> substituents are present on the same nitrogen atom, then each R<1> substituent is independently selected from the list of R<1> values described thereafter,
and wherein n is an integer equal to either 0, 1, 2, 3, 4, or 5,
and wherein, when (R<1>) and R<1> are attached to a nitrogen atom, optionally they join together with the nitrogen atom to form a 3 to 7-membered ring which optionally includes one or more other heteroatom selected from N, O and S, optionally the ring is substituted with one or more R<1> or R<A>;
L is
1) —Ci-6 alkyl,
2) —C2-6 alkenyl,
3) —C2-6 alkynyl,
4) —C3-7 cycloalkyl,
5) —C3-7 cycloalkenyl,
6) heterocyclyl,
7) —Ci-6 alkyl-C3-7 cycloalkyl,
8) —Ci-6 alkyl-heterocyclyl,
9) aryl, or
10) heteroaryl,
and wherein the alkyl, the alkenyl, the alkynyl, the cycloalkyl, the cycloalkenyl, the heterocyclyl, the aryl and the heteroaryl groups are each independently optionally substituted with one or two R<A> substituent;
Ri is
1) —H,
2) —C1-6 alkyl,
3) —C2-6 alkenyl,
4) —C2-6 alkynyl, 5) —C3-7 cycloalkyl,
6) —C3-7 cycloalkenyl,
7) —C1-5 perfluorinated,
8) -heterocycyl,
9) -aryl,
10) -heteroaryl,
11) -benzyl, or
12) 5-[(3aS,4S,6aR)-2-oxohexahydro-1H-thieno[3,4-d]imidazol-4-yl]pentanoyl,
and wherein the alkyl, the alkenyl, the alkynyl, the cycloalkenyl, the perfluorinated alkyl, the heterocycyl, the aryl, the heteroaryl and the benzyl groups are each independently optionally substituted with 1, 2 or 3 R<A> or R<1> substituents;
R2 is
1) —H,
2) —C1-6 alkyl,
3) —SR,
4) —C(O)R1,
5) —S(O)R1,
6) —S(O)2R<1>,
7) -benzyl optionally substituted with 1, 2 or 3 R<A> or R<1> substituents,
8) -L-heteroaryl optionally substituted with one or more R<A> or R<1> substituents attached on either one or both the L and the heteroaryl groups,
9) -L-heterocyclyl optionally substituted with one or more R<A> or R<1> substituents attached on either one or both the L and the heterocycyl groups,
10) -L-aryl optionally substituted with one or more R<A> or R<1> substituents attached on either one or both the L and the aryl groups,
11) -heteroaryl optionally substituted with one or more R<A> or R<1> substituents, or
12) -aryl optionally substituted with one or more R<A> or R<1> substituents,
and wherein each substituent is optionally attached to the L group if it is not already present;
R<A> is
1) -halogen,
2) —CFs, 3) —OH,
4) —OR<1>,
5) -L-OH,
6) -L-OR<1>,
7) —OCFs,
8) —SH,
9) —SR1,
10) —CN,
11) —NO2,
12) —NH2,
13) —NHR<1>,
14) —NR<1>R<1>,
15) -L-NH2,
16) -L-NHR<1>,
17) -L-NR<4>R<1>,
18) -L-SR<1>,
19) -L-S(O)R<1>,
20) -L-S(O)2R<1>,
21) —C(O)OH,
22) —C(O)OR<1>,
23) —C(O)NH2,
24) —C(O)NHR<1>,
25) —C(O)N(R<1>)R<1>,
26) —NHC(O)R<1>,
27) —NR1C(O)R<1>,
28) —NHC(O)OR<1>,
29) —NR1C(O)OR<1>,
30) —OC(O)NH2,
31) —OC(O)NHR<1>,
32) —OC(O)N(R)R<1>,
33) —OC(O)R<1>,
34) —C(O)R1, 35) —NHC(O)NH2,
36) —NHC(O)NHR1,
37) —NHC(O)N(R)R<1>,
38) —NR C(O)NH2,
39) —NR C(O)NHR<1>,
40) —NR1C(O)N(R1)R1,
41) —NHS(O)2R<1>,
42) —NR S(O)2R<1>,
43) —S(O)2NH2,
44) —S(O)2NHR<1>,
45) —S(O)2N(R)R<1>,
46) —S(O)R<1>,
47) —S(O)2R<1>,
48) —OS(O)2R<1>,
49) —S(O)2OR<1>,
50) -benzyl,
51) —N3, or
52) —C(—N=N—)(CF3),
and wherein the benzyl group is optionally substituted with 1, 2 or 3 R<A> or R<1> substituents.

In certain aspects, said pyrimido(4,5-b)indole derivative has the chemical structure

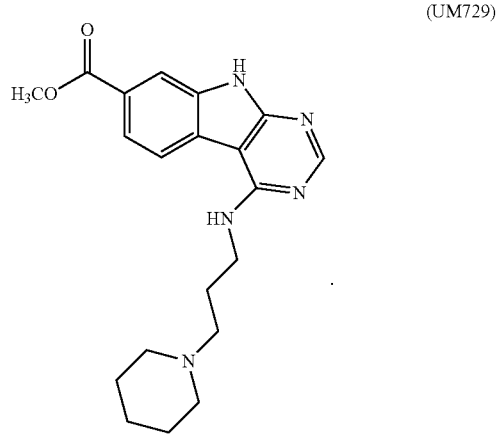 [SMILES: COC(=O)c1ccc2c(c1)[nH]c1ncnc(NCCCN3CCCCC3)c12]

(UM729)

In certain aspects, said pyrimido(4,5-b)indole derivative has the chemical structure

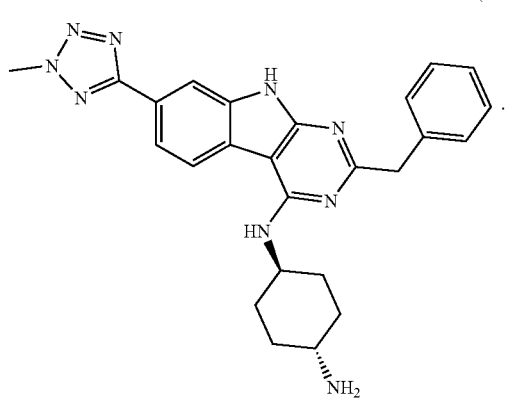

(UM171)

In certain aspects, said third medium used in the three-stage method comprises IL-2 and IL-15, and lacks a stem cell mobilizing agent and LMWH. In certain aspects, the third medium used in the three-stage method comprises, in addition to IL-2 and IL-15, one or more of SCF, IL-6, IL-7, G-CSF, or GM-CSF. In certain aspects, the third medium used in the three-stage method comprises, in addition to IL-2 and IL-15, each of SCF, IL-6, IL-7, G-CSF, and GM-CSF. In certain aspects, said IL-2 is present in said third medium at a concentration of from 10 U/mL to 10,000 U/mL and said IL-15 is present in said third medium at a concentration of from 1 ng/mL to 50 ng/mL. In certain aspects, said IL-2 is present in said third medium at a concentration of from 100 U/mL to 10,000 U/mL and said IL-15 is present in said third medium at a concentration of from 1 ng/mL to 50 ng/mL. In certain aspects, said IL-2 is present in said third medium at a concentration of from 300 U/mL to 3,000 U/mL and said IL-15 is present in said third medium at a concentration of from 10 ng/mL to 30 ng/mL. In certain aspects, said IL-2 is present in said third medium at a concentration of about 1,000 U/mL and said IL-15 is present in said third medium at a concentration of about 20 ng/mL. In certain aspects, in said third medium, the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in said third medium, the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in said third medium, the SCF is present at a concentration of about 22 ng/mL; the IL-6 is present at a concentration of about 0.05 ng/mL; the IL-7 is present at a concentration of about 20 ng/mL; the G-CSF is present at a concentration of about 0.25 ng/mL; and the GM-CSF is present at a concentration of about 0.01 ng/mL. In certain embodiments, said third medium is not GBGM®.

Generally, the particularly recited medium components do not refer to possible constituents in an undefined component of said medium, e.g., serum. For example, said Tpo, IL-2, and IL-15 are not comprised within an undefined component of the first medium, second medium or third medium, e.g., said Tpo, IL-2, and IL-15 are not comprised within serum. Further, said LMWH, Flt-3, SCF, IL-6, IL-7, G-CSF, and/or GM-CSF are not comprised within an undefined component of the first medium, second medium or third medium, e.g., said LMWH, Flt-3, SCF, IL-6, IL-7, G-CSF, and/or GM-CSF are not comprised within serum.

In certain aspects, said first medium, second medium or third medium comprises human serum-AB. In certain aspects, any of said first medium, second medium or third medium comprises 1% to 20% human serum-AB, 5% to 15% human serum-AB, or about 2, 5, or 10% human serum-AB.

In certain aspects, any of said first medium, second medium or third medium comprises 2-mercaptoethanol. In certain aspects, any of said first medium, second medium or third medium comprises gentamycin.

In certain embodiments, in the three-stage methods described herein, said hematopoietic stem or progenitor cells are cultured in said first medium for 1, 2, 3, 4, 5, 6, 7, 8, 9, 10, 11, 12, 13, 14, 15, 16, 17, 18, 19, or 20 days before said culturing in said second medium. In certain embodiments, cells are cultured in said second medium for 1, 2, 3, 4, 5, 6, 7, 8, 9, 10, 11, 12, 13, 14, 15, 16, 17, 18, 19, or 20 days before said culturing in said third medium. In certain embodiments, cells are cultured in said third medium for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or for more than 30 days.

In one embodiment, in the three-stage methods described herein, said hematopoietic stem or progenitor cells are cultured in said first medium for 7-13 days to produce a first population of cells; said first population of cells are cultured in said second medium for 2-6 days to produce a second population of cells; and said second population of cells are cultured in said third medium for 10-30 days, i.e., the cells are cultured a total of 19-49 days.

In one embodiment, in the three-stage methods described herein, said hematopoietic stem or progenitor cells are cultured in said first medium for 8-12 days to produce a first population of cells; said first population of cells are cultured in said second medium for 3-5 days to produce a second population of cells; and said second population of cells are cultured in said third medium for 15-25 days, i.e., the cells are cultured a total of 26-42 days.

In a specific embodiment, in the three-stage methods described herein, said hematopoietic stem or progenitor cells are cultured in said first medium for about 10 days to produce a first population of cells; said first population of cells are cultured in said second medium for about 4 days to produce a second population of cells; and said second population of cells are cultured in said third medium for about 21 days, i.e., the cells are cultured a total of about 35 days.

In certain aspects, said culturing in said first medium, second medium and third medium are all performed under static culture conditions, e.g., in a culture dish or culture flask. In certain aspects, said culturing in at least one of said first medium, second medium or third medium are performed in a spinner flask. In certain aspects, said culturing in said first medium and said second medium is performed under static culture conditions, and said culturing in said third medium is performed in a spinner flask.

In certain aspects, said culturing is performed in a spinner flask. In other aspects, said culturing is performed in a G-Rex device. In yet other aspects, said culturing is performed in a WAVE bioreactor.

In certain aspects, said hematopoietic stem or progenitor cells are initially inoculated into said first medium from $1\times10^4$ to $1\times10^5$ cells/mL. In a specific aspect, said hematopoietic stem or progenitor cells are initially inoculated into said first medium at about $3\times10^4$ cells/mL.

In certain aspects, said first population of cells are initially inoculated into said second medium from $5\times10^4$ to $5\times10^5$ cells/mL. In a specific aspect, said first population of cells is initially inoculated into said second medium at about $1\times10^5$ cells/mL.

In certain aspects said second population of cells is initially inoculated into said third medium from $1\times10^5$ to $5\times10^6$ cells/mL. In certain aspects, said second population of cells is initially inoculated into said third medium from $1\times10^5$ to $1\times10^6$ cells/mL. In a specific aspect, said second population of cells is initially inoculated into said third medium at about $5\times10^5$ cells/mL. In a more specific aspect, said second population of cells is initially inoculated into said third medium at about $5\times10^5$ cells/mL in a spinner flask. In a specific aspect, said second population of cells is initially inoculated into said third medium at about $3\times10^5$ cells/mL. In a more specific aspect, said second population of cells is initially inoculated into said third medium at about $3\times10^5$ cells/mL in a static culture.

In certain aspects, the three-stage method disclosed herein produces at least 5000-fold more natural killer cells as compared to the number of hematopoietic stem cells initially inoculated into said first medium. In certain aspects, said three-stage method produces at least 10,000-fold more natural killer cells as compared to the number of hematopoietic stem cells initially inoculated into said first medium. In certain aspects, said three-stage method produces at least 50,000-fold more natural killer cells as compared to the number of hematopoietic stem cells initially inoculated into said first medium. In certain aspects, said three-stage method produces at least 75,000-fold more natural killer cells as compared to the number of hematopoietic stem cells initially inoculated into said first medium. In certain aspects, the viability of said natural killer cells is determined by 7-aminoactinomycin D (7AAD) staining. In certain aspects, the viability of said natural killer cells is determined by annexin-V staining. In specific aspects, the viability of said natural killer cells is determined by both 7-AAD staining and annexin-V staining. In certain aspects, the viability of said natural killer cells is determined by trypan blue staining.

In certain aspects, the three-stage method disclosed herein produces natural killer cells that comprise at least 20% CD56+CD3− natural killer cells. In certain aspects, the three-stage method produces natural killer cells that comprise at least 40% CD56+CD3− natural killer cells. In certain aspects, the three-stage method produces natural killer cells that comprise at least 60% CD56+CD3− natural killer cells. In certain aspects, the three-stage method produces natural killer cells that comprise at least 70% CD56+CD3− natural killer cells. In certain aspects, the three-stage method produces natural killer cells that comprise at least 75% CD56+CD3− natural killer cells. In certain aspects, the three-stage method produces natural killer cells that comprise at least 80% CD56+CD3− natural killer cells.

In certain aspects, the three-stage method disclosed herein, produces natural killer cells that exhibit at least 20% cytotoxicity against K562 cells when said natural killer cells and said K562 cells are co-cultured in vitro at a ratio of 10:1. In certain aspects, the three-stage method produces natural killer cells that exhibit at least 35% cytotoxicity against the K562 cells when said natural killer cells and said K562 cells are co-cultured in vitro at a ratio of 10:1. In certain aspects, the three-stage method produces natural killer cells that exhibit at least 45% cytotoxicity against the K562 cells when said natural killer cells and said K562 cells are co-cultured in vitro at a ratio of 10:1. In certain aspects, the three-stage method produces natural killer cells that exhibit at least 60% cytotoxicity against the K562 cells when said natural killer cells and said K562 cells are co-cultured in vitro at a ratio of 10:1. In certain aspects, the three-stage method produces natural killer cells that exhibit at least 75% cytotoxicity against the K562 cells when said natural killer cells and said K562 cells are co-cultured in vitro at a ratio of 10:1.

In certain aspects, after said third culturing step, said third population of cells, e.g., said population of natural killer cells, is cryopreserved.

In certain aspects, provided herein are populations of cells comprising natural killer cells, i.e., natural killers cells produced by a three-stage method described herein. Accordingly, provided herein is an isolated natural killer cell population produced by a three-stage method described herein. In a specific embodiment, said natural killer cell population comprises at least 20% CD56+CD3− natural killer cells. In a specific embodiment, said natural killer cell population comprises at least 40% CD56+CD3− natural killer cells. In a specific embodiment, said natural killer cell population comprises at least 60% CD56+CD3− natural killer cells. In a specific embodiment, said natural killer cell population comprises at least 80% CD56+CD3− natural killer cells.

In one embodiment, provided herein is an isolated NK progenitor cell population, wherein said NK progenitor cells are produced according to the three-stage method described herein.

In another embodiment, provided herein is an isolated mature NK cell population, wherein said mature NK cells are produced according to the three-stage method described herein.

In another embodiment, provided herein is an isolated NK cell population, wherein said NK cells are activated, wherein said activated NK cells are produced according to the three-stage method described herein.

Accordingly, in another aspect, provided herein is the use of NK cell populations produced using the three-stage methods described herein to suppress acute myeloid leukemia cell proliferation. In certain embodiments, the NK cell populations are used in combination with IL-2.

In another aspect, provided herein is the use of NK cell populations produced using the three-stage methods described herein to suppress multiple myeloma cell proliferation. In certain embodiments, the NK cell populations are used in combination with IL-2.

In another specific embodiment, the hematopoietic cells, e.g., hematopoietic stem cells or progenitor cells, from which the NK cell populations are produced, are obtained from placental perfusate, umbilical cord blood or peripheral blood. In one embodiment, the hematopoietic cells, e.g., hematopoietic stem cells or progenitor cells, from which NK cell populations are produced, are obtained from placenta, e.g., from placental perfusate. In one embodiment, the hematopoietic cells, e.g., hematopoietic stem cells or progenitor cells, from which the NK cell populations are produced, are not obtained from umbilical cord blood. In one embodiment, the hematopoietic cells, e.g., hematopoietic stem cells or progenitor cells, from which the NK cell populations are produced, are not obtained from peripheral blood. In another specific embodiment, the hematopoietic cells, e.g., hematopoietic stem cells or progenitor cells, from which the NK cell populations are produced, are combined cells from placental perfusate and cord blood, e.g., cord blood from the same placenta as the perfusate. In another specific embodiment, said umbilical cord blood is isolated from a placenta other than the placenta from which said placental perfusate is obtained. In certain embodiments, the combined cells can be obtained by pooling or combining the cord blood and placental perfusate. In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by volume to obtain the combined cells. In a specific embodiment, the cord blood and placental perfusate are combined at a ratio of from 10:1 to 1:10, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10. In a more specific embodiment, the cord blood and placental perfusate are combined at a ratio of 8.5:1.5 (85%:15%).

In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like, as determined by total nucleated cells (TNC) content to obtain the combined cells. In a specific embodiment, the cord blood and placental perfusate are combined at a ratio of from 10:1 to 10:1, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10.

In one embodiment, therefore, provided herein is a method of treating an individual having acute myeloid leukemia, comprising administering to said individual an effective amount of cells from an isolated NK cell population produced using a three-stage method described herein. In certain aspects, said natural killer cells have been cryopreserved prior to said contacting or said administering. In other aspects, said natural killer cells have not been cryopreserved prior to said contacting or said administering.

In one embodiment, therefore, provided herein is a method of treating an individual having multiple myeloma, comprising administering to said individual an effective amount of cells from an isolated NK cell population produced using a three-stage method described herein. In certain aspects, said natural killer cells have been cryopreserved prior to said contacting or said administering. In other aspects, said natural killer cells have not been cryopreserved prior to said contacting or said administering.

In a specific embodiment, the NK cell populations produced using the three-stage methods described herein have been treated with an immunomodulatory compound, e.g. an immunomodulatory compound described herein, or thalidomide, prior to said administration. In a specific embodiment, the NK cell populations produced using the three-stage methods described herein have been treated with IL2 and IL12 and IL18, IL12 and IL15, IL12 and IL18, IL2 and IL12 and IL15 and IL18, or IL2 and IL15 and IL18 prior to said administration. In another specific embodiment, the method comprises administering to the individual (1) an effective amount of an isolated NK cell population produced using a three-stage method described herein; and (2) an effective amount of an immunomodulatory compound or thalidomide. An "effective amount" in this context means an amount of cells in an NK cell population, and optionally immunomodulatory compound or thalidomide, that results in a detectable improvement in one or more symptoms of said cancer or said infection, compared to an individual having said cancer or said infection who has not been administered said NK cell population and, optionally, an immunomodulatory compound or thalidomide. In a specific embodiment, said immunomodulatory compound is lenalidomide or pomalidomide.

In another embodiment, provided herein is a method of suppressing the proliferation of acute myeloid leukemia cells comprising bringing a therapeutically effective amount of an NK cell population into proximity with the acute myeloid leukemia cells, e.g., contacting the acute myeloid leukemia cells with the cells in an NK cell population. Hereinafter, unless noted otherwise, the term "proximity" refers to sufficient proximity to elicit the desired result; e.g., in certain embodiments, the term proximity refers to contact. In certain embodiments, said contacting takes place in vitro. In other embodiments, said contacting takes place in vivo.

In another embodiment, provided herein is a method of suppressing the proliferation of multiple myeloma cells comprising bringing a therapeutically effective amount of an NK cell population into proximity with the acute myeloid leukemia cells, e.g., contacting the multiple myeloma cells with the cells in an NK cell population. In certain embodiments, said contacting takes place in vitro. In other embodiments, said contacting takes place in vivo.

Administration of an isolated population of NK cells or a pharmaceutical composition thereof is systemic. In specific embodiments, administration of an isolated population of NK cells or a pharmaceutical composition thereof to a subject is by infusion. In specific embodiments, administration of an isolated population of NK cells or a pharmaceutical composition thereof to a subject is by intravenous (IV) infusion.

In another aspect, provided herein is a method of treating an individual having acute myeloid leukemia, comprising administering to the individual NK cells, wherein said NK cells are effective to treat AML, in said individual. In a specific embodiment, said NK cells are cord blood NK cells, or NK cells produced from cord blood hematopoietic cells, e.g., hematopoietic stem cells. In another embodiment, said NK cells have been produced by any of the methods described herein for producing NK cells, e.g., for producing NK cell populations using a three-stage method as set forth herein. In certain specific embodiments of the method of treating an individual with acute myeloid leukemia, said NK cell populations are produced by a three-stage method, as described herein. In a particular embodiment, the acute myeloid leukemia to be treated by the foregoing methods comprises refractory acute myeloid leukemia, poor-prognosis acute myeloid leukemia, or childhood acute myeloid leukemia. In certain embodiments, said individual has acute myeloid leukemia that has failed at least one non-natural killer cell therapeutic against acute myeloid leukemia. In specific embodiments, said individual is 65 years old or greater, and is in first remission. In specific embodiments, said individual has been conditioned with chemotherapies, for example, fludarabine, cytarabine, or both, prior to administering said natural killer cells.

In another aspect, provided herein is a method of treating an individual having multiple myeloma, comprising administering to the individual NK cells, wherein said NK cells are effective to treat multiple myeloma in said individual. In a specific embodiment, said NK cells are cord blood NK cells, or NK cells produced from cord blood hematopoietic cells, e.g., hematopoietic stem cells. In another embodiment, said NK cells have been produced by any of the methods described herein for producing NK cells, e.g., for producing NK cell populations using a three-stage method as set forth herein. In certain specific embodiments of the method of treating an individual with multiple myeloma, said NK cell populations are produced by a three-stage method, as described herein. In specific embodiments, said individual has received an autologous stem cell transplant prior to administering said natural killer cells. In specific embodiments, said individual has received melphalan prior to administering said natural killer cells.

In certain embodiments, the NK cell populations produced using a three-stage method described herein are cryopreserved, e.g., cryopreserved using a method described herein. In a certain embodiments, the NK cell populations produced using a three-stage method described herein are cryopreserved in a cryopreservation medium, e.g., a cryopreservation medium described herein. In a specific embodiment, cryopreservation of the NK progenitor cell populations and/or NK cell populations produced using a three-stage method described herein comprises (1) preparing a cell suspension solution comprising an NK progenitor cell population and/or an NK cell population produced using a three-stage method described herein; (2) adding cryopreservation medium to the cell suspension solution from step (1) to obtain a cryopreserved cell suspension; (3) cooling the cryopreserved cell suspension from step (3) to obtain a cryopreserved sample; and (4) storing the cryopreserved sample below −80° C.

In certain embodiments of the methods of treatment or tumor suppression above, NK cell populations produced by a three-stage method described herein are combined with other natural killer cells, e.g., natural killer cells isolated from placental perfusate, umbilical cord blood or peripheral blood, or produced from hematopoietic cells by a different method. In specific embodiments, the natural killer cell populations are combined with natural killer cells from another source, or made by a different method, in a ratio of about 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In another aspect, provided herein is a composition comprising isolated NK cells produced by a three-stage method described herein. In a specific embodiment, said NK cells are produced from hematopoietic cells, e.g., hematopoietic stem or progenitor cells isolated from placental perfusate, umbilical cord blood, and/or peripheral blood. In another specific embodiment, said NK cells comprise at least 70% of cells in the composition. In another specific embodiment, said NK cells comprise at least 80%, 85%, 90%, 95%, 98% or 99% of cells in the composition. In certain embodiments, at least 80%, 82%, 84%, 86%, 88% or 90% of NK cells in said composition are CD3⁻ and CD56⁺. In certain embodiments, at least 65%, 70%, 75%, 80%, 82%, 84%, 86%, 88% or 90% of NK cells in said composition are CD16−. In certain embodiments, at least 5%, 10%, 15%, 20%, 25%, 30%, 35%, 40%, 45%, 50%, 55% or 60% of NK cells in said composition are CD94+.

In a specific embodiment, said NK cells are from a single individual. In a more specific embodiment, said NK cells comprise natural killer cells from at least two different individuals. In another specific embodiment, said NK cells are from a different individual than the individual for whom treatment with the NK cells is intended. In another specific embodiment, said NK cells have been contacted or brought into proximity with an immunomodulatory compound or thalidomide in an amount and for a time sufficient for said NK cells to express detectably more granzyme B or perforin than an equivalent number of natural killer cells, i.e. NK cells, not contacted or brought into proximity with said immunomodulatory compound or thalidomide.

In a more specific embodiment, the composition comprises NK cells produced by a three-stage method described herein and natural killer cells from another source, or made by another method. In a specific embodiment, said other source is placental blood and/or umbilical cord blood. In another specific embodiment, said other source is peripheral blood. In more specific embodiments, the NK cells are combined with natural killer cells from another source, or made by another method in a ratio of about 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In another aspect, provided herein is a composition, e.g., a pharmaceutical composition, comprising an isolated NK cell population, e.g., produced by the three-stage method described herein. In a specific embodiment, said isolated NK cell population is produced from hematopoietic cells, e.g., hematopoietic stem or progenitor cells isolated from placenta, e.g., from placental perfusate, umbilical cord blood, and/or peripheral blood. In another specific embodiment, said isolated NK cell population comprises at least 70% of cells in the composition. In another specific embodiment, said isolated NK cell population comprises at least 80%, 85%, 90%, 95%, 98% or 99% of cells in the composition. In another specific embodiment, said NK cells comprise at least 70% of cells in the composition. In certain embodiments, at least 80%, 82%, 84%, 86%, 88% or 90% of NK cells in said composition are CD3⁻ and CD56⁺. In certain embodiments, at least 65%, 70%, 75%, 80%, 82%, 84%, 86%, 88% or 90% of NK cells in said composition are CD16−. In certain embodiments, at least 5%, 10%, 15%, 20%, 25%, 30%, 35%, 40%, 45%, 50%, 55% or 60% of NK cells in said composition are CD94+.

In another specific embodiment, said isolated NK cells in said composition are from a single individual. In a more specific embodiment, said isolated NK cells comprise NK cells from at least two different individuals. In another specific embodiment, said isolated NK cells in said composition are from a different individual than the individual for whom treatment with the NK cells is intended. In another specific embodiment, said NK cells have been contacted or brought into proximity with an immunomodulatory compound or thalidomide in an amount and for a time sufficient for said NK cells to express detectably more granzyme B or perforin than an equivalent number of natural killer cells, i.e.

NK cells not contacted or brought into proximity with said immunomodulatory compound or thalidomide.

In a more specific embodiment, the composition comprises NK cells from another source, or made by another method. In a specific embodiment, said other source is placental blood and/or umbilical cord blood. In another specific embodiment, said other source is peripheral blood. In more specific embodiments, the NK cell population in said composition is combined with NK cells from another source, or made by another method in a ratio of about 100:1, 95:5, 90:10, 85:15, 80:20, 75:25, 70:30, 65:35, 60:40, 55:45, 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

3.1. Terminology

As used herein, the terms "immunomodulatory compound" and "IMiD™" do not encompass thalidomide.

As used herein, "lenalidomide" means 3-(4'aminoisoindoline-1'-one)-1-piperidine-2,6-dione (Chemical Abstracts Service name) or 2,6-Piperidinedione,3-(4-amino-1,3-dihydro-1-oxo-2H-isoindol-2-yl)-(International Union of Pure and Applied Chemistry (IUPAC) name). As used herein, "pomalidomide" means 4-amino-2-(2,6-dioxopiperidin-3-yl)isoindole-1,3-dione.

As used herein, "multipotent," when referring to a cell, means that the cell has the capacity to differentiate into a cell of another cell type. In certain embodiments, "a multipotent cell" is a cell that has the capacity to grow into a subset of the mammalian body's approximately 260 cell types. Unlike a pluripotent cell, a multipotent cell does not have the capacity to form all of the cell types.

As used herein, "feeder cells" refers to cells of one type that are co-cultured with cells of a second type, to provide an environment in which the cells of the second type can be maintained, and perhaps proliferate. Without being bound by any theory, feeder cells can provide, for example, peptides, polypeptides, electrical signals, organic molecules (e.g., steroids), nucleic acid molecules, growth factors (e.g., bFGF), other factors (e.g., cytokines), and metabolic nutrients to target cells. In certain embodiments, feeder cells grow in a mono-layer.

As used herein, the "natural killer cells" or "NK cells" produced using the methods described herein, without further modification, include natural killer cells from any tissue source.

As used herein, "placental perfusate" means perfusion solution that has been passed through at least part of a placenta, e.g., a human placenta, e.g., through the placental vasculature, and includes a plurality of cells collected by the perfusion solution during passage through the placenta.

As used herein, "placental perfusate cells" means nucleated cells, e.g., total nucleated cells, isolated from, or isolatable from, placental perfusate.

As used herein, "tumor cell suppression," "suppression of tumor cell proliferation," and the like, includes slowing the growth of a population of tumor cells, e.g., by killing one or more of the tumor cells in said population of tumor cells, for example, by contacting or bringing, e.g., NK cells or an NK cell population produced using a three-stage method described herein into proximity with the population of tumor cells, e.g., contacting the population of tumor cells with NK cells or an NK cell population produced using a three-stage method described herein. In certain embodiments, said contacting takes place in vitro. In other embodiments, said contacting takes place in vivo.

As used herein, the term "hematopoietic cells" includes hematopoietic stem cells and hematopoietic progenitor cells.

As used herein, the "undefined component" is a term of art in the culture medium field that refers to components whose constituents are not generally provided or quantified. Examples of an "undefined component" include, without limitation, serum, for example, human serum (e.g., human serum AB) and fetal serum (e.g., fetal bovine serum or fetal calf serum).

As used herein, "+", when used to indicate the presence of a particular cellular marker, means that the cellular marker is detectably present in fluorescence activated cell sorting over an isotype control; or is detectable above background in quantitative or semi-quantitative RT-PCR.

As used herein, "−", when used to indicate the presence of a particular cellular marker, means that the cellular marker is not detectably present in fluorescence activated cell sorting over an isotype control; or is not detectable above background in quantitative or semi-quantitative RT-PCR.

4. DETAILED DESCRIPTION

Provided herein are methods of treatment of an individual having acute myeloid leukemia using the NK cells produced using the methods described herein, e.g., NK cell populations produced using the three-stage method described herein. The methods of treatment provided herein can be part of an anticancer therapy regimen that includes administration of IL-2. In certain embodiments, the IL-2 is human IL-2. In certain embodiments, the IL-2 is recombinant human IL-2 (rhIL-2).

Further provided herein are methods of suppressing the proliferation of acute myeloid leukemia cells, comprising bringing NK cells produced using the methods described herein, e.g., NK cell populations produced using the three-stage method described herein, into proximity with the acute myeloid leukemia cells, e.g., contacting the acute myeloid leukemia cells with NK cells produced using the methods described herein. In certain embodiments, provided herein is a method of suppressing the proliferation of acute myeloid leukemia cells, comprising bringing NK cells produced using the methods described herein, e.g., NK cell populations produced using the three-stage method described herein, into proximity with the acute myeloid leukemia cells, e.g., contacting the acute myeloid leukemia cells with NK cells produced using the methods described herein, further comprising bringing IL-2 into proximity with the NK cells and/or the acute myeloid leukemia cells, e.g., contacting the NK cells and/or acute myeloid leukemia cells with IL-2. In specific embodiments, the IL-2 is rhIL-2.

Provided herein are methods of treatment of an individual having multiple myeloma using the NK cells produced using the methods described herein, e.g., NK cell populations produced using the three-stage method described herein. The methods of treatment provided herein can be part of an anticancer therapy regimen that includes administration of IL-2. In certain embodiments, the IL-2 is human IL-2. In certain embodiments, the IL-2 is recombinant human IL-2 (rhIL-2). In certain embodiments, said individual has received chemotherapy prior to administering said natural killer cells. In specific embodiments, the chemotherapy is an alkylating agent. In more specific embodiments, the alkylating agent is melphalan. In certain embodiments, melphalan is administered according to the label. In certain embodiments, the individual having multiple myeloma is an individual that has received an autologous stem cell transplant before said administering. In certain embodiments, the autologous stem cell transplant was in treatment of said multiple myeloma. In certain embodiments, the stem cells in the autologous stem cell transplant are peripheral blood mononuclear cells.

Further provided herein are methods of suppressing the proliferation of multiple myeloma cells, comprising bringing NK cells produced using the methods described herein, e.g., NK cell populations produced using the three-stage method described herein, into proximity with the multiple myeloma cells, e.g., contacting the acute myeloid leukemia cells with NK cells produced using the methods described herein. In certain embodiments, provided herein is a method of suppressing the proliferation of multiple myeloma cells, comprising bringing NK cells produced using the methods described herein, e.g., NK cell populations produced using the three-stage method described herein, into proximity with the multiple myeloma cells, e.g., contacting the multiple myeloma cells with NK cells produced using the methods described herein, further comprising bringing IL-2 into proximity with the NK cells and/or the multiple myeloma cells, e.g., contacting the NK cells and/or multiple myeloma cells with IL-2. In specific embodiments, the IL-2 is rhIL-2.

Provided herein are novel methods of producing and expanding NK cells from hematopoietic cells, e.g., hematopoietic stem cells or progenitor cells. Also provided herein are methods, e.g., three-stage methods, of producing NK cell populations from hematopoietic cells, e.g., hematopoietic stem cells or progenitor cells. The hematopoietic cells used to produce the NK cells, and NK cell populations, may be obtained from any source, for example, without limitation, placenta, umbilical cord blood, placental blood, peripheral blood, spleen or liver. In certain embodiments, the NK cells or NK cell populations are produced from expanded hematopoietic cells, e.g., hematopoietic stem cells and/or hematopoietic progenitor cells. In one embodiment, hematopoietic cells are collected from a source of such cells, e.g., placenta, for example from placental perfusate, umbilical cord blood, placental blood, peripheral blood, spleen, liver and/or bone marrow.

The hematopoietic cells used to produce the NK cells and NK cell populations may be obtained from any animal species. In certain embodiments, the hematopoietic stem or progenitor cells are mammalian cells. In specific embodiments, said hematopoietic stem or progenitor cells are human cells. In specific embodiments, said hematopoietic stem or progenitor cells are primate cells. In specific embodiments, said hematopoietic stem or progenitor cells are canine cells. In specific embodiments, said hematopoietic stem or progenitor cells are rodent cells.

4.1. Hematopoietic Cells

Hematopoietic cells useful in the methods disclosed herein can be any hematopoietic cells able to differentiate into NK cells, e.g., precursor cells, hematopoietic progenitor cells, hematopoietic stem cells, or the like. Hematopoietic cells can be obtained from tissue sources such as, e.g., bone marrow, cord blood, placental blood, peripheral blood, liver or the like, or combinations thereof. Hematopoietic cells can be obtained from placenta. In a specific embodiment, the hematopoietic cells are obtained from placental perfusate. In one embodiment, the hematopoietic cells are not obtained from umbilical cord blood. In one embodiment, the hematopoietic cells are not obtained from peripheral blood. Hematopoietic cells from placental perfusate can comprise a mixture of fetal and maternal hematopoietic cells, e.g., a mixture in which maternal cells comprise greater than 5% of the total number of hematopoietic cells. In certain embodiments, hematopoietic cells from placental perfusate comprise at least about 90%, 95%, 98%, 99% or 99.5% fetal cells.

In another specific embodiment, the hematopoietic cells, e.g., hematopoietic stem cells or progenitor cells, from which the NK cell populations produced using a three-stage method described herein are produced, are obtained from placental perfusate, umbilical cord blood, fetal liver, mobilized peripheral blood, or bone marrow. In another specific embodiment, the hematopoietic cells, e.g., hematopoietic stem cells or progenitor cells, from which the NK cell populations produced using a three-stage method described herein are produced, are combined cells from placental perfusate and cord blood, e.g., cord blood from the same placenta as the perfusate. In another specific embodiment, said umbilical cord blood is isolated from a placenta other than the placenta from which said placental perfusate is obtained. In certain embodiments, the combined cells can be obtained by pooling or combining the cord blood and placental perfusate. In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by volume to obtain the combined cells. In a specific embodiment, the cord blood and placental perfusate are combined at a ratio of from 10:1 to 1:10, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10. In a more specific embodiment, the cord blood and placental perfusate are combined at a ratio of 8.5:1.5 (85%:15%).

In certain embodiments, the cord blood and placental perfusate are combined at a ratio of 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like by total nucleated cells (TNC) content to obtain the combined cells. In a specific embodiment, the cord blood and placental perfusate are combined at a ratio of from 10:1 to 10:1, from 5:1 to 1:5, or from 3:1 to 1:3. In another specific embodiment, the cord blood and placental perfusate are combined at a ratio of 10:1, 5:1, 3:1, 1:1, 1:3, 1:5 or 1:10.

In another specific embodiment, the hematopoietic cells, e.g., hematopoietic stem cells or progenitor cells from which said NK cell populations produced using a three-stage method described herein are produced, are from both umbilical cord blood and placental perfusate, but wherein said umbilical cord blood is isolated from a placenta other than the placenta from which said placental perfusate is obtained.

In certain embodiments, the hematopoietic cells are $CD34^+$ cells. In specific embodiments, the hematopoietic cells useful in the methods disclosed herein are $CD34^+$ $CD38^+$ or $CD34^+CD38^-$. In a more specific embodiment, the hematopoietic cells are $CD34^+CD38^-Lin^-$. In another specific embodiment, the hematopoietic cells are one or more of $CD2^-$, $CD3^-$, $CD11b^-$, $CD11c^-$, $CD14^-$, $CD16^-$, $CD19^-$, $CD24^-$, $CD56^-$, $CD66b^-$ and/or glycophorin K. In another specific embodiment, the hematopoietic cells are CD2⁻, CD3⁻, CD11b⁻, CD11c⁻, CD14⁻, CD16⁻, CD19⁻, CD24⁻, CD56⁻, CD66b⁻ and glycophorin K. In another more specific embodiment, the hematopoietic cells are CD34⁺CD38⁻CD33⁻CD117⁻. In another more specific embodiment, the hematopoietic cells are CD34⁺CD38⁻CD33⁻CD117⁻CD235⁻CD36⁻.

In another embodiment, the hematopoietic cells are CD45⁺. In another specific embodiment, the hematopoietic cells are CD34⁺CD45⁺. In another embodiment, the hematopoietic cell is Thy-1⁺. In a specific embodiment, the hematopoietic cell is CD34⁺Thy-1⁺. In another embodiment, the hematopoietic cells are CD133⁺. In specific embodiments, the hematopoietic cells are CD34⁺CD133⁺ or CD133⁺Thy-1⁺. In another specific embodiment, the CD34⁺ hematopoietic cells are CXCR4⁺. In another specific embodiment, the CD34⁺ hematopoietic cells are CXCR4⁻. In another embodiment, the hematopoietic cells are positive for KDR (vascular growth factor receptor 2). In specific embodiments, the hematopoietic cells are CD34⁺KDR⁺, CD133⁺KDR⁺ or Thy-1⁺KDR⁺. In certain other embodiments, the hematopoietic cells are positive for aldehyde dehydrogenase (ALDH⁺), e.g., the cells are CD34⁺ALDH⁺.

In certain embodiments, the hematopoietic cells are CD34⁻.

The hematopoietic cells can also lack certain markers that indicate lineage commitment, or a lack of developmental naiveté. For example, in another embodiment, the hematopoietic cells are HLA-DR⁻. In specific embodiments, the hematopoietic cells are CD34⁺HLA-DR⁻, CD133⁺HLA-DR⁻, Thy-1⁺HLA-DR⁻ or ALDH⁺HLA-DR⁻ In another embodiment, the hematopoietic cells are negative for one or more, or all, of lineage markers CD2, CD3, CD11b, CD11c, CD14, CD16, CD19, CD24, CD56, CD66b and glycophorin A.

Thus, hematopoietic cells can be selected for use in the methods disclosed herein on the basis of the presence of markers that indicate an undifferentiated state, or on the basis of the absence of lineage markers indicating that at least some lineage differentiation has taken place. Methods of isolating cells, including hematopoietic cells, on the basis of the presence or absence of specific markers is discussed in detail below.

Hematopoietic cells used in the methods provided herein can be a substantially homogeneous population, e.g., a population comprising at least about 95%, at least about 98% or at least about 99% hematopoietic cells from a single tissue source, or a population comprising hematopoietic cells exhibiting the same hematopoietic cell-associated cellular markers. For example, in various embodiments, the hematopoietic cells can comprise at least about 95%, 98% or 99% hematopoietic cells from bone marrow, cord blood, placental blood, peripheral blood, or placenta, e.g., placenta perfusate.

Hematopoietic cells used in the methods provided herein can be obtained from a single individual, e.g., from a single placenta, or from a plurality of individuals, e.g., can be pooled. Where the hematopoietic cells are obtained from a plurality of individuals and pooled, the hematopoietic cells may be obtained from the same tissue source. Thus, in various embodiments, the pooled hematopoietic cells are all from placenta, e.g., placental perfusate, all from placental blood, all from umbilical cord blood, all from peripheral blood, and the like.

Hematopoietic cells used in the methods disclosed herein can, in certain embodiments, comprise hematopoietic cells from two or more tissue sources. For example, in certain embodiments, when hematopoietic cells from two or more sources are combined for use in the methods herein, a plurality of the hematopoietic cells used to produce natural killer cells using a three-stage method described herein comprise hematopoietic cells from placenta, e.g., placenta perfusate. In various embodiments, the hematopoietic cells used to produce NK cell populations produced using a three-stage method described herein, comprise hematopoietic cells from placenta and from cord blood; from placenta and peripheral blood; from placenta and placental blood, or placenta and bone marrow. In one embodiment, the hematopoietic cells comprise hematopoietic cells from placental perfusate in combination with hematopoietic cells from cord blood, wherein the cord blood and placenta are from the same individual, i.e., wherein the perfusate and cord blood are matched. In embodiments in which the hematopoietic cells comprise hematopoietic cells from two tissue sources, the hematopoietic cells from the sources can be combined in a ratio of, for example, 1:10, 2:9, 3:8, 4:7, 5:6, 6:5, 7:4, 8:3, 9:2, 1:10, 1:9, 1:8, 1:7, 1:6, 1:5, 1:4, 1:3, 1:2, 1:1, 2:1, 3:1, 4:1, 5:1, 6:1, 7:1, 8:1 or 9:1.

4.1.1. Placental Hematopoietic Stem Cells

In certain embodiments, the hematopoietic cells used in the methods provided herein are placental hematopoietic cells. In one embodiment, placental hematopoietic cells are CD34⁺. In a specific embodiment, the placental hematopoietic cells are predominantly (e.g., at least about 50%, 55%, 60%, 65%, 70%, 75%, 80%, 85%, 90%, 95% or 98%) CD34⁺CD38⁻ cells. In another specific embodiment, the placental hematopoietic cells are predominantly (e.g., at least about 50%, 55%, 60%, 65%, 70%, 75%, 80%, 85%, 90%, 95% or 98%) CD34⁺CD38⁺ cells. Placental hematopoietic cells can be obtained from a post-partum mammalian (e.g., human) placenta by any means known to those of skill in the art, e.g., by perfusion.

In another embodiment, the placental hematopoietic cell is CD45⁻. In a specific embodiment, the hematopoietic cell is CD34⁺CD45⁻. In another specific embodiment, the placental hematopoietic cells are CD34⁺CD45⁺.

4.2. Production of Natural Killer Cells and Natural Killer Cell Populations

Production of NK cells and NK cell populations by the present methods comprises expanding a population of hematopoietic cells. During cell expansion, a plurality of hematopoietic cells within the hematopoietic cell population differentiate into NK cells. In one aspect, provided herein is a method of producing NK cells comprising culturing hematopoietic stem cells or progenitor cells, e.g., CD34⁺ stem cells or progenitor cells, in a first medium comprising a stem cell mobilizing agent and thrombopoietin (Tpo) to produce a first population of cells, subsequently culturing said first population of cells in a second medium comprising a stem cell mobilizing agent and interleukin-15 (IL-15), and lacking Tpo, to produce a second population of cells, and subsequently culturing said second population of cells in a third medium comprising IL-2 and IL-15, and lacking a stem cell mobilizing agent and LMWH, to produce a third population of cells, wherein the third population of cells comprises natural killer cells that are CD56+, CD3-, and wherein at least 70%, for example 80%, of the natural killer cells are viable with certain embodiments, such natural killer cells comprise natural killer cells that are CD16–. In certain embodiments, such natural killer cells comprise natural killer cells that are CD94+. In certain embodiments, such natural killer cells comprise natural killer cells that are CD94+ or CD16+. In certain embodiments, such natural killer cells comprise natural killer cells that are CD94– or CD16−. In certain embodiments, such natural killer cells comprise natural killer cells that are CD94+ and CD16+. In certain embodiments, such natural killer cells comprise natural killer cells that are CD94− and CD16−.

4.2.1. Production of NK Cell Populations Using a Three-Stage Method

In one embodiment, provided herein is a three-stage method of producing NK cell populations. In certain embodiments, the method of expansion and differentiation of the hematopoietic cells, as described herein, to produce NK cell populations according to a three-stage method described herein comprises maintaining the cell population comprising said hematopoietic cells at between about $2\times10^4$ and about $6\times10^6$ cells per milliliter. In certain aspects, said hematopoietic stem or progenitor cells are initially inoculated into said first medium from $1\times10^4$ to $1\times10^5$ cells/mL. In a specific aspect, said hematopoietic stem or progenitor cells are initially inoculated into said first medium at about $3\times10^4$ cells/mL.

In certain aspects, said first population of cells are initially inoculated into said second medium from $5\times10^4$ to $5\times10^5$ cells/mL. In a specific aspect, said first population of cells is initially inoculated into said second medium at about $1\times10^5$ cells/mL.

In certain aspects said second population of cells is initially inoculated into said third medium from $1\times10^5$ to $5\times10^6$ cells/mL. In certain aspects, said second population of cells is initially inoculated into said third medium from $1\times10^5$ to $1\times10^6$ cells/mL. In a specific aspect, said second population of cells is initially inoculated into said third medium at about $5\times10^5$ cells/mL. In a more specific aspect, said second population of cells is initially inoculated into said third medium at about $5\times10^5$ cells/mL in a spinner flask. In a specific aspect, said second population of cells is initially inoculated into said third medium at about $3\times10^5$ cells/mL. In a more specific aspect, said second population of cells is initially inoculated into said third medium at about $3\times10^5$ cells/mL in a static culture.

In a certain embodiment, the three-stage method comprises a first stage ("stage 1") comprising culturing hematopoietic stem cells or progenitor cells, e.g., $CD34^+$ stem cells or progenitor cells, in a first medium for a specified time period, e.g., as described herein, to produce a first population of cells. In certain embodiments, the first medium comprises a stem cell mobilizing agent and thrombopoietin (Tpo). In certain embodiments, the first medium comprises in addition to a stem cell mobilizing agent and Tpo, one or more of LMWH, Flt-3L, SCF, IL-6, IL-7, G-CSF, and GM-CSF. In a specific embodiment, the first medium comprises each of the first medium comprises in addition to a stem cell mobilizing agent and Tpo, each of LMWH, Flt-3L, SCF, IL-6, IL-7, G-CSF, and GM-CSF. In a specific embodiment, the first medium lacks added LMWH. In a specific embodiment, the first medium lacks added desulphated glycosaminoglycans. In a specific embodiment, the first medium lacks LMWH. In a specific embodiment, the first medium lacks desulphated glycosaminoglycans. In a specific embodiment, the first medium comprises in addition to a stem cell mobilizing agent and Tpo, each of Flt-3L, SCF, IL-6, IL-7, G-CSF, and GM-CSF.

In certain embodiments, subsequently, in "stage 2" said cells are cultured in a second medium for a specified time period, e.g., as described herein, to produce a second population of cells. In certain embodiments, the second medium comprises a stem cell mobilizing agent and interleukin-15 (IL-15), and lacks Tpo. In certain embodiments, the second medium comprises, in addition to a stem cell mobilizing agent and IL-15, one or more of LMWH, Flt-3, SCF, IL-6, IL-7, G-CSF, and GM-CSF. In certain embodiments, the second medium comprises, in addition to a stem cell mobilizing agent and IL-15, each of LMWH, Flt-3, SCF, IL-6, IL-7, G-CSF, and GM-CSF. In a specific embodiment, the second medium lacks added LMWH. In a specific embodiment, the second medium lacks added desulphated glycosaminoglycans. In a specific embodiment, the second medium lacks LMWH. In a specific embodiment, the second medium lacks desulphated glycosaminoglycans. In certain embodiments, the second medium comprises, in addition to a stem cell mobilizing agent and IL-15, each of Flt-3, SCF, IL-6, IL-7, G-CSF, and GM-CSF.

In certain embodiments, subsequently, in "stage 3" said cells are cultured in a third medium for a specified time period, e.g., as described herein, to produce a third population of cell, e.g., natural killer cells. In certain embodiments, the third medium comprises IL-2 and IL-15, and lacks a stem cell mobilizing agent and LMWH. In certain embodiments, the third medium comprises in addition to IL-2 and IL-15, one or more of SCF, IL-6, IL-7, G-CSF, and GM-CSF. In certain embodiments, the third medium comprises in addition to IL-2 and IL-15, each of SCF, IL-6, IL-7, G-CSF, and GM-CSF. In specific embodiments, the third medium lacks desulphated glycosaminoglycans. In specific embodiments, the third medium lacks added desulphated glycosaminoglycans.

In a specific embodiment, the three-stage method is used to produce NK cell populations. In certain embodiments, the three-stage method is conducted in the absence of stromal feeder cell support. In certain embodiments, the three-stage method is conducted in the absence of exogenously added steroids (e.g., cortisone, hydrocortisone, or derivatives thereof).

In certain aspects, said first medium used in the three-stage method comprises a stem cell mobilizing agent and thrombopoietin (Tpo). In certain aspects, the first medium used in the three-stage method comprises, in addition to a stem cell mobilizing agent and Tpo, one or more of Low Molecular Weight Heparin (LMWH), Flt-3 Ligand (Flt-3L), stem cell factor (SCF), IL-6, IL-7, granulocyte colony-stimulating factor (G-CSF), or granulocyte-macrophage-stimulating factor (GM-CSF). In certain aspects, the first medium used in the three-stage method comprises, in addition to a stem cell mobilizing agent and Tpo, each of LMWH, Flt-3L, SCF, IL-6, IL-7, G-CSF, and GM-CSF. In certain aspects, the first medium used in the three-stage method comprises, in addition to a stem cell mobilizing agent and Tpo, each of Flt-3L, SCF, IL-6, IL-7, G-CSF, and GM-CSF. In a specific aspect, the first medium lacks added LMWH. In a specific aspect, the first medium lacks added desulphated glycosaminoglycans. In a specific aspect, the first medium lacks LMWH. In a specific aspect, the first medium lacks desulphated glycosaminoglycans. In certain aspects, said Tpo is present in the first medium at a concentration of from 1 ng/mL to 100 ng/mL, from 1 ng/mL to 50 ng/mL, from 20 ng/mL to 30 ng/mL, or about 25 ng/mL. In certain aspects, in the first medium, the LMWH is present at a concentration of from 1 U/mL to 10 U/mL; the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in the first medium, the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in the first medium, the LMWH is present at a concentration of from 4 U/mL to 5 U/mL; the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the first medium, the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the first medium, the LMWH is present at a concentration of about 4.5 U/mL; the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain aspects, in the first medium, the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain embodiments, said first medium additionally comprises one or more of the following: antibiotics such as gentamycin; antioxidants such as transferrin, insulin, and/or beta-mercaptoethanol; sodium selenite; ascorbic acid; ethanolamine; and glutathione. In certain embodiments, the medium that provides the base for the first medium is a cell/tissue culture medium known to those of skill in the art, e.g., a commercially available cell/tissue culture medium such as SCGM™, STEMMACS™, GBGM®, AIM-V®, X-VIVO™ 10, X-VIVO™ 15, OPTMIZER, STEMSPAN® H3000, CELLGRO COMPLETE™, DMEM:Ham's F12 ("F12") (e.g., 2:1 ratio, or high glucose or low glucose DMEM), Advanced DMEM (Gibco), EL08-1D2, Myelocult™ H5100, IMDM, and/or RPMI-1640; or is a medium that comprises components generally included in known cell/tissue culture media, such as the components included in GBGM®, AIM-V®, X-VIVO™ 10, X-VIVO™ 15, OPTMIZER, STEMSPAN® H3000, CELLGRO COMPLETE™, DMEM:Ham's F12 ("F12") (e.g., 2:1 ratio, or high glucose or low glucose DMEM), Advanced DMEM (Gibco), EL08-1D2, Myelocult™ H5100, IMDM, and/or RPMI-1640. In certain embodiments, said first medium is not GBGM®.

In certain aspects, said second medium used in the three-stage method comprises a stem cell mobilizing agent and interleukin-15 (IL-15), and lacks Tpo. In certain aspects, the second medium used in the three-stage method comprises, in addition to a stem cell mobilizing agent and IL-15, one or more of LMWH, Flt-3, SCF, IL-6, IL-7, G-CSF, and GM-CSF. In certain aspects, the second medium used in the three-stage method comprises, in addition to a stem cell mobilizing agent and IL-15, each of LMWH, Flt-3, SCF, IL-6, IL-7, G-CSF, and GM-CSF. In certain aspects, the second medium used in the three-stage method comprises, in addition to a stem cell mobilizing agent and IL-15, each of Flt-3, SCF, IL-6, IL-7, G-CSF, and GM-CSF. In a specific aspect, the second medium lacks added LMWH. In a specific aspect, the second medium lacks added desulphated glycosaminoglycans. In a specific aspect, the second medium lacks LMWH. In a specific aspect, the second medium lacks desulphated glycosaminoglycans. In certain aspects, said IL-15 is present in said second medium at a concentration of from 1 ng/mL to 50 ng/mL, from 10 ng/mL to 30 ng/mL, or about 20 ng/mL. In certain aspects, in said second medium, the LMWH is present at a concentration of from 1 U/mL to 10 U/mL; the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in said second medium, the Flt-3L is present at a concentration of from 1 ng/mL to 50 ng/mL; the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in the second medium, the LMWH is present in the second medium at a concentration of from 4 U/mL to 5 U/mL; the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the LMWH is present in the second medium at a concentration of from 4 U/mL to 5 U/mL; the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the Flt-3L is present at a concentration of from 20 ng/mL to 30 ng/mL; the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in the second medium, the LMWH is present in the second medium at a concentration of about 4.5 U/mL; the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain aspects, in the second medium, the Flt-3L is present at a concentration of about 25 ng/mL; the SCF is present at a concentration of about 27 ng/mL; the IL-6 is present at a concentration of about 0.05 ng/mL; the IL-7 is present at a concentration of about 25 ng/mL; the G-CSF is present at a concentration of about 0.25 ng/mL; and the GM-CSF is present at a concentration of about 0.01 ng/mL. In certain embodiments, said second medium additionally comprises one or more of the following: antibiotics such as gentamycin; antioxidants such as transferrin, insulin, and/or beta-mercaptoethanol; sodium selenite; ascorbic acid; ethanolamine; and glutathione. In certain embodiments, the medium that provides the base for the second medium is a cell/tissue culture medium known to those of skill in the art, e.g., a commercially available cell/tissue culture medium such as SCGM™, STEM-MACS™, GBGM®, AIM-V®, X-VIVO™ 10, X-VIVO™ 15, OPTMIZER, STEMSPAN® H3000, CELLGRO COMPLETE™, DMEM:Ham's F12 ("F12") (e.g., 2:1 ratio, or high glucose or low glucose DMEM), Advanced DMEM (Gibco), EL08-1D2, Myelocult™ H5100, IMDM, and/or RPMI-1640; or is a medium that comprises components generally included in known cell/tissue culture media, such as the components included in GBGM®, AIM-V®, X-VIVO™ 10, X-VIVO 15, OPTMIZER, STEMSPAN® H3000, CELLGRO COMPLETE™, DMEM:Ham's F12 ("F12") (e.g., 2:1 ratio, or high glucose or low glucose DMEM), Advanced DMEM (Gibco), EL08-1D2, Myelocult™ H5100, IMDM, and/or RPMI-1640. In certain embodiments, said second medium is not GBGM®.

In certain embodiments, the third medium used in the three-stage method comprises medium comprising In certain aspects, said third medium used in the three-stage method comprises IL-2 and IL-15, and lacks a stem cell mobilizing agent and LMWH. In certain aspects, the third medium used in the three-stage method comprises, in addition to IL-2 and IL-15, one or more of SCF, IL-6, IL-7, G-CSF, or GM-CSF. In certain aspects, the third medium used in the three-stage method comprises, in addition to IL-2 and IL-15, each of SCF, IL-6, IL-7, G-CSF, and GM-CSF. In certain aspects, said IL-2 is present in said third medium at a concentration of from 10 U/mL to 10,000 U/mL and said IL-15 is present in said third medium at a concentration of from 1 ng/mL to 50 ng/mL. In certain aspects, said IL-2 is present in said third medium at a concentration of from 100 U/mL to 10,000 U/mL and said IL-15 is present in said third medium at a concentration of from 1 ng/mL to 50 ng/mL. In certain aspects, said IL-2 is present in said third medium at a concentration of from 300 U/mL to 3,000 U/mL and said IL-15 is present in said third medium at a concentration of from 10 ng/mL to 30 ng/mL. In certain aspects, said IL-2 is present in said third medium at a concentration of about 1,000 U/mL and said IL-15 is present in said third medium at a concentration of about 20 ng/mL. In certain aspects, in said third medium, the SCF is present at a concentration of from 1 ng/mL to 50 ng/mL; the IL-6 is present at a concentration of from 0.01 ng/mL to 0.1 ng/mL; the IL-7 is present at a concentration of from 1 ng/mL to 50 ng/mL; the G-CSF is present at a concentration of from 0.01 ng/mL to 0.50 ng/mL; and the GM-CSF is present at a concentration of from 0.005 ng/mL to 0.1 ng/mL. In certain aspects, in said third medium, the SCF is present at a concentration of from 20 ng/mL to 30 ng/mL; the IL-6 is present at a concentration of from 0.04 ng/mL to 0.06 ng/mL; the IL-7 is present at a concentration of from 20 ng/mL to 30 ng/mL; the G-CSF is present at a concentration of from 0.20 ng/mL to 0.30 ng/mL; and the GM-CSF is present at a concentration of from 0.005 ng/mL to 0.5 ng/mL. In certain aspects, in said third medium, the SCF is present at a concentration of about 22 ng/mL; the IL-6 is present at a concentration of about 0.05 ng/mL; the IL-7 is present at a concentration of about 20 ng/mL; the G-CSF is present at a concentration of about 0.25 ng/mL; and the GM-CSF is present at a concentration of about 0.01 ng/mL. In certain embodiments, said third medium additionally comprises one or more of the following: antibiotics such as gentamycin; antioxidants such as transferrin, insulin, and/or beta-mercaptoethanol; sodium selenite; ascorbic acid; ethanolamine; and glutathione. In certain embodiments, the medium that provides the base for the third medium is a cell/tissue culture medium known to those of skill in the art, e.g., a commercially available cell/tissue culture medium such as SCGM™, STEM-MACS™, GBGM®, AIM-V®, X-VIVO™ 10, X-VIVO™ 15, OPTMIZER, STEMSPAN® H3000, CELLGRO COMPLETE™, DMEM:Ham's F12 ("F12") (e.g., 2:1 ratio, or high glucose or low glucose DMEM), Advanced DMEM (Gibco), EL08-1D2, Myelocult™ H5100, IMDM, and/or RPMI-1640; or is a medium that comprises components generally included in known cell/tissue culture media, such as the components included in GBGM®, AIM-V®, X-VIVO™ 10, X-VIVO™ 15, OPTMIZER, STEMSPAN® H3000, CELLGRO COMPLETE™, DMEM:Ham's F12 ("F12") (e.g., 2:1 ratio, or high glucose or low glucose DMEM), Advanced DMEM (Gibco), EL08-1D2, Myelocult™ H5100, IMDM, and/or RPMI-1640. In certain embodiments, said third medium is not GBGM®.

Generally, the particularly recited medium components do not refer to possible constituents in an undefined component of said medium. For example, said Tpo, IL-2, and IL-15 are not comprised within an undefined component of the first medium, second medium or third medium, e.g., said Tpo, IL-2, and IL-15 are not comprised within serum. Further, said LMWH, Flt-3, SCF, IL-6, IL-7, G-CSF, and/or GM-CSF are not comprised within an undefined component of the first medium, second medium or third medium, e.g., said LMWH, Flt-3, SCF, IL-6, IL-7, G-CSF, and/or GM-CSF are not comprised within serum.

In certain aspects, said first medium, second medium or third medium comprises human serum-AB. In certain aspects, any of said first medium, second medium or third medium comprises 1% to 20% human serum-AB, 5% to 15% human serum-AB, or about 2, 5, or 10% human serum-AB.

In certain embodiments, in the three-stage methods described herein, said hematopoietic stem or progenitor cells are cultured in said first medium for 1, 2, 3, 4, 5, 6, 7, 8, 9, 10, 11, 12, 13, 14, 15, 16, 17, 18, 19, or 20 days. In certain embodiments, in the three-stage methods described herein, cells are cultured in said second medium for 1, 2, 3, 4, 5, 6, 7, 8, 9, 10, 11, 12, 13, 14, 15, 16, 17, 18, 19, or 20 days. In certain embodiments, in the three-stage methods described herein, cells are cultured in said third medium for 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, or for more than 30 days.

In a specific embodiment, in the three-stage methods described herein, said hematopoietic stem or progenitor cells are cultured in said first medium for 7-13 days to produce a first population of cells, before said culturing in said second medium; said first population of cells are cultured in said second medium for 2-6 days to produce a second population of cells before said culturing in said third medium; and said second population of cells are cultured in said third medium for 10-30 days, i.e., the cells are cultured a total of 19-49 days.

In a specific embodiment, in the three-stage methods described herein, in the three-stage methods described herein, said hematopoietic stem or progenitor cells are cultured in said first medium for 8-12 days to produce a first population of cells, before said culturing in said second medium; said first population of cells are cultured in said second medium for 3-5 days to produce a second population of cells before said culturing in said third medium; and said second population of cells are cultured in said third medium for 15-25 days, i.e., the cells are cultured a total of 26-42 days.

In a specific embodiment, in the three-stage methods described herein, said hematopoietic stem or progenitor cells are cultured in said first medium for about 10 days to produce a first population of cells, before said culturing in said second medium; said first population of cells are cultured in said second medium for about 4 days to produce a second population of cells before said culturing in said third medium; and said second population of cells are cultured in said third medium for about 21 days, i.e., the cells are cultured a total of about 35 days.

In certain aspects, the three-stage method disclosed herein produces at least 5000-fold more natural killer cells as compared to the number of hematopoietic stem cells initially inoculated into said first medium. In certain aspects, said three-stage method produces at least 10,000-fold more natural killer cells as compared to the number of hematopoietic stem cells initially inoculated into said first medium. In certain aspects, said three-stage method produces at least 50,000-fold more natural killer cells as compared to the number of hematopoietic stem cells initially inoculated into said first medium. In certain aspects, said three-stage method produces at least 75,000-fold more natural killer cells as compared to the number of hematopoietic stem cells initially inoculated into said first medium. In certain aspects, the viability of said natural killer cells is determined by 7-aminoactinomycin D (7AAD) staining. In certain aspects, the viability of said natural killer cells is determined by annexin-V staining. In specific aspects, the viability of said natural killer cells is determined by both 7-AAD staining and annexin-V staining. In certain aspects, the viability of said natural killer cells is determined by trypan blue staining.

In certain aspects, the three-stage method produces natural killer cells that comprise at least 20% CD56+CD3− natural killer cells. In certain aspects, the three-stage method produces natural killer cells that comprise at least 40% CD56+CD3− natural killer cells. In certain aspects, the three-stage method produces natural killer cells that comprise at least 60% CD56+CD3− natural killer cells. In certain aspects, the three-stage method produces natural killer cells that comprise at least 70% CD56+CD3− natural killer cells. In certain aspects, the three-stage method produces natural killer cells that comprise at least 80% CD56+CD3− natural killer cells.

In certain aspects, the three-stage method produces natural killer cells that exhibit at least 20% cytotoxicity against K562 cells when said natural killer cells and said K562 cells are co-cultured in vitro at a ratio of 10:1. In certain aspects, the three-stage method produces natural killer cells that exhibit at least 35% cytotoxicity against the K562 cells when said natural killer cells and said K562 cells are co-cultured in vitro at a ratio of 10:1. In certain aspects, the three-stage method produces natural killer cells that exhibit at least 45% cytotoxicity against the K562 cells when said natural killer cells and said K562 cells are co-cultured in vitro at a ratio of 10:1. In certain aspects, the three-stage method produces natural killer cells that exhibit at least 60% cytotoxicity against the K562 cells when said natural killer cells and said K562 cells are co-cultured in vitro at a ratio of 10:1. In certain aspects, the three-stage method produces natural killer cells that exhibit at least 75% cytotoxicity against the K562 cells when said natural killer cells and said K562 cells are co-cultured in vitro at a ratio of 10:1.

In certain aspects, after said third culturing step, said third population of cells, e.g., said population of natural killer cells, is cryopreserved.

In certain aspects, provided herein are populations of cells comprising natural killer cells, i.e., natural killers cells produced by a three-stage method described herein. Accordingly, provided herein is an isolated natural killer cell population produced by a three-stage method described herein. In a specific embodiment, said natural killer cell population comprises at least 20% CD56+CD3− natural killer cells. In a specific embodiment, said natural killer cell population comprises at least 40% CD56+CD3− natural killer cells. In a specific embodiment, said natural killer cell population comprises at least 60% CD56+CD3− natural killer cells. In a specific embodiment, said natural killer cell population comprises at least 80% CD56+CD3− natural killer cells. In a specific embodiment, said natural killer cell population comprises at least 60% CD16− cells. In a specific embodiment, said natural killer cell population comprises at least 80% CD16− cells. In a specific embodiment, said natural killer cell population comprises at least 20% CD94+ cells. In a specific embodiment, said natural killer cell population comprises at least 40% CD94+ cells.

4.3. Stem Cell Mobilizing Factors 4.3.1. Chemistry Definitions

To facilitate understanding of the disclosure of stem cell mobilizing factors set forth herein, a number of terms are defined below.

Generally, the nomenclature used herein and the laboratory procedures in biology, cellular biology, biochemistry, organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "aryl hydrocarbon receptor" or "AHR" refers to a protein encoded by the AHR gene in humans, or a variant thereof (for example, see GenBank Accession Nos. P35869.2 and AAH70080.1).

The term "aryl hydrocarbon receptor antagonist," "AHR antagonist," "aryl hydrocarbon receptor inhibitor," or "AHR inhibitor" refers to a compound that downregulates or reduces the activity of an aryl hydrocarbon receptor.

The term "alkyl" refers to a linear or branched saturated monovalent hydrocarbon radical, wherein the alkyl is optionally substituted with one or more substituents Q as described herein. The term "alkyl" also encompasses both linear and branched alkyl, unless otherwise specified. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkylene" refers to a linear or branched saturated divalent hydrocarbon radical, wherein the alkylene is optionally substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms).

The term "alkenyl" refers to a linear or branched monovalent hydrocarbon radical, which contains one or more, in one embodiment, one, two, three, four, or five, in another embodiment, one, carbon-carbon double bond(s). The alkenyl is optionally substituted with one or more substituents Q as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkenylene" refers to a linear or branched divalent hydrocarbon radical, which contains one or more, in one embodiment, one to five, in another embodiment, one, carbon-carbon double bond(s). The alkenylene is optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene.

The term "alkynyl" refers to a linear or branched monovalent hydrocarbon radical, which contains one or more, in one embodiment, one, two, three, four, or five, in another embodiment, one, carbon-carbon triple bond(s). The alkynyl is optionally substituted with one or more substituents Q as described herein. The term "alkynyl" also encompasses both linear and branched alkynyl, unless otherwise specified. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl(CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "alkynylene" refers to a linear or branched divalent hydrocarbon radical, which contains one or more, in one embodiment, one to five, in another embodiment, one, carbon-carbon triple bond(s). The alkynylene is optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene, propynylene (including all isomeric forms, e.g., 1-propynylene and propargylene), butynylene (including all isomeric forms, e.g., 1-butyn-1-ylene and 2-butyn-1-ylene), pentenylene (including all isomeric forms, e.g., 1-pentyn-1-ylene and 1-methyl-2-butyn-1-ylene), and hexynylene (including all isomeric forms, e.g., 1-hexyn-1-ylene).

The term "cycloalkyl" refers to a cyclic saturated or non-aromatic unsaturated, bridged or non-bridged monovalent hydrocarbon radical, which is optionally substituted with one or more substituents Q as described herein. In certain embodiments, the cycloalkyl is a cyclic saturated bridged or non-bridged monovalent hydrocarbon radical. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "cycloalkylene" refers to a cyclic divalent hydrocarbon radical, which is optionally substituted with one or more substituents Q as described herein. In one embodiment, cycloalkyl groups is saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene.

The term "aryl" refers to a monocyclic aromatic carbocyclic group and/or multicyclic monovalent aromatic carbocyclic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. In certain embodiments, the term "aryl" refers to a bicyclic or tricyclic carbon ring, where one of the rings is aromatic and the others of which can be saturated, partially unsaturated, or aromatic, for example, dihydronaphthyl, indenyl, indanyl, or tetrahydronaphthyl(tetralinyl). The aryl is optionally substituted with one or more substituents Q as described herein.

The term "arylene" refers to a divalent monocyclic aromatic group and/or divalent polycyclic aromatic group that contain at least one aromatic carbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which can be saturated, partially unsaturated, or aromatic, for example, dihydronaphthylene, indenylene, indanylene, or tetrahydronaphthylene (tetralinylene). The arylene is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 1-phenylethyl, 2-phenylethyl, and 3-phenylpropyl. The aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each of which is independently selected from O, S, N, and P, in the ring. For clarity, the terms "aryl" and "heteroaryl" as used herein are mutually exclusive, i.e., "aryl" groups do not include "heteroaryl" groups, and vice versa. A heteroaryl group is bonded to the rest of a molecule through its aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. The heteroaryl is optionally substituted with one or more substituents Q as described herein.

The term "heteroarylene" refers to a divalent monocyclic aromatic group or divalent polycyclic aromatic group that contain at least one aromatic ring, wherein at least one aromatic ring contains one or more heteroatoms independently selected from O, S, and N in the ring. For clarity, the terms "arylene" and "heteroarylene" as used herein are mutually exclusive, i.e., "arylene" groups do not include "heteroarylene" groups, and vice versa. A heteroarylene group is bonded to the rest of a molecule through its aromatic ring. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothienylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. The heteroarylene is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each of which is independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which can be spiro, fused, or bridged, and in which nitrogen or sulfur atoms can be optionally oxidized, nitrogen atoms can be optionally quaternized, and some rings can be partially or fully saturated, or aromatic. The heterocyclyl can be attached to the main structure at any heteroatom or carbon atom which results in the creation of a stable compound. Examples of heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. The heterocyclyl is optionally substituted with one or more substituents Q as described herein.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which can be fused or bridged, and in which nitrogen or sulfur atoms can be optionally oxidized, nitrogen atoms can be optionally quaternized, and some rings can be partially or fully saturated, or aromatic. The heterocyclylene can be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothienylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. The heterocyclylene is optionally substituted with one or more substituents Q as described herein.

The term "halogen", "halide" or "halo" refers to fluorine, chlorine, bromine, and/or iodine.

The term "haloalkyl" refers to an alkyl group substituted with one or more, in one embodiment, one, two, or three, halo groups, where the alkyl is as defined herein. The haloalkyl is optionally substituted with one or more substituents Q as described herein.

The term "alkoxy" refers to —O-alkyl, where the alkyl is as defined herein.

The term "haloalkoxy" refers to —O-haloalkyl, where the haloalkyl is as defined herein.

The term "optionally substituted" is intended to mean that a group or substituent, such as an alkyl, alkylene, alkenyl, alkenylene, alkynyl, alkynylene, cycloalkyl, cycloalkylene, aryl, arylene, aralkyl (e.g., benzyl), heteroaryl, heteroarylene, heterocyclyl, and heterocyclylene group, may be substituted with one or more substituents Q, each of which is independently selected from, e.g., (a) oxo (=O), cyano (—CN), halo, and nitro (—NO$_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, four, or five, substituents $Q^a$; and (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$)N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O)$R^d$, —N$R^a$S(O)$_2 R^d$, —N$R^a$S(O)N$R^b R^c$, —N$R^a$S(O)$_2$N$R^b R^c$, —P(O)$R^a R^d$, —P(O)(O$R^a$)$R^d$, —P(O)(O$R^a$)(O$R^d$), —S$R^a$, —S(O)$R^a$, —S(O)$_2 R^a$, —S(O)N$R^b R^c$, and —S(O)$_2$N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-4}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heteroaryl or heterocyclyl, each of which is optionally substituted with one or more, in one embodiment, one, two, three, or four, substituents $Q^a$. As used herein, all groups described herein that can be substituted are "optionally substituted," unless otherwise specified.

In one embodiment, each substituent $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)

$R^h$, —$NR^eC(O)OR^h$, —$NR^eC(O)NR^fR^g$, —$NR^eC(=NR^h)$ $NR^fR^g$, —$NR^eS(O)R^h$, —$NR^eS(O)_2R^h$, —$NR^eS(O)NR^fR^g$, —$NR^eS(O)_2NR^fR^g$, —$P(O)R^eR^h$, —$P(O)(OR^e)R^h$, —$P(O)(OR^e)(OR^h)$, —$S(O)R^e$, —$S(O)_2R^e$, —$S(O)NR^fR^g$, and —$S(O)_2NR^fR^g$; wherein each $R^e$, $R^f$, $R^g$, and $R^h$ is independently (i) hydrogen, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (ii) $R^f$ and $R^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of the desired enantiomer and about 5% or less of the less preferred enantiomer based on the total weight of the two enantiomers in question.

In describing an optically active compound, the prefixes R and S are used to denote the absolute configuration of the optically active compound about its chiral center(s). The (+) and (−) are used to denote the optical rotation of an optically active compound, that is, the direction in which a plane of polarized light is rotated by the optically active compound. The (−) prefix indicates that an optically active compound is levorotatory, that is, the compound rotates the plane of polarized light to the left or counterclockwise. The (+) prefix indicates that an optically active compound is dextrorotatory, that is, the compound rotates the plane of polarized light to the right or clockwise. However, the sign of optical rotation, (+) and (−), is not related to the absolute configuration of a compound, R and S.

The term "isotopic variant" refers to a compound that contains an unnatural proportion of an isotope at one or more of the atoms that constitute such a compound. In certain embodiments, an "isotopic variant" of a compound contains unnatural proportions of one or more isotopes, including, but not limited to, hydrogen ($^1H$), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1H$), deuterium ($^2H$), carbon-12 ($^{12}C$), carbon-13 ($^{13}C$), nitrogen-14 ($^{14}N$), nitrogen-15 ($^{15}N$), oxygen-16 ($^{16}O$), oxygen-17 ($^{17}O$), oxygen-18 fluorine-17 ($^{17}F$), phosphorus-31 ($^{31}P$), sulfur-32 ($^{32}S$), sulfur-33 ($^{33}S$), sulfur-34 ($^{34}S$), sulfur-36 ($^{36}S$), chlorine-35 ($^{35}Cl$), chlorine-37 ($^{37}Cl$), bromine-79 ($^{79}Br$), bromine-81 ($^{81}Br$), and iodine-127 ($^{127}I$). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3H$), carbon-11 ($^{11}C$), carbon-14 ($^{14}C$), nitrogen-13 ($^{13}N$), oxygen-14 ($^{14}O$), oxygen-15 ($^{15}O$), fluorine-18 ($^{18}F$), phosphorus-32 ($^{32}P$), phosphorus-33 ($^{33}P$), sulfur-35 ($^{35}S$), chlorine-36 ($^{36}Cl$), iodine-123 ($^{123}I$), iodine-125 ($^{125}I$), iodine-129 ($^{129}I$), and iodine-131 ($^{131}I$). It will be understood that, in a compound as provided herein, any hydrogen can be $^2H$, for example, or any carbon can be $^{13}C$, for example, or any nitrogen can be $^{15}N$, for example, or any oxygen can be $^{18}O$, for example, where feasible according to the judgment of one of skill. In certain embodiments, an "isotopic variant" of a compound contains unnatural proportions of deuterium (D).

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "an enantiomer, a mixture of enantiomers, a mixture of two or more diastereomers, or an isotopic variant thereof; or a pharmaceutically acceptable salt, solvate, hydrate, or prodrug thereof" has the same meaning as the phrase "(i) an enantiomer, a mixture of enantiomers, a mixture of two or more diastereomers, or an isotopic variant of the compound referenced therein; (ii) a pharmaceutically acceptable salt, solvate, hydrate, or prodrug of the compound referenced therein; or (iii) a pharmaceutically acceptable salt, solvate, hydrate, or prodrug of an enantiomer, a mixture of enantiomers, a mixture of two or more diastereomers, or an isotopic variant of the compound referenced therein."

4.3.2. Stem Cell Mobilizing Compounds

In one embodiment, the stem cell mobilizing compound is an aryl hydrocarbon receptor inhibitor, e.g., an aryl hydrocarbon receptor antagonist.

In another embodiment, the stem cell mobilizing compound is a 5,6-fused heteroaryl compound, including, but not limited to, those described in U.S. Pat. App. Pub. Nos. 2010/0183564, 2014/0023626, and 2014/0114070, the disclosure of each of which is incorporated herein by reference in its entirety.

In yet another embodiment, the stem cell mobilizing compound is a compound of Formula I:

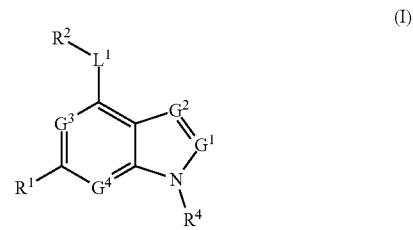

(I)

or an enantiomer, a mixture of enantiomers, a mixture of two or more diastereomers, or an isotopic variant thereof; or a pharmaceutically acceptable salt, solvate, hydrate, or prodrug thereof; wherein:

$G^1$ is N and $CR^3$;

$G^2$, $G^3$, and $G^4$ are each independently CH and N; with the proviso that at least one of $G^3$ and $G^4$ is N, and at least one of $G^1$ and $G^2$ is not N;

$L^1$ is $-NR^{1a}-$, $-NR^{1a}(CH_2)_{1-3}-$, $-NR^{1a}CH(C(O)OCH_3)CH_2-$, $-NR^{1a}(CH_2)_2NR^{1c}-$, $-NR^{1a}(CH_2)_2S-$, $-NR^{1a}CH_2CH(CH_3)CH_2-$, $-NR^{1a}CH_2CH(OH)-$, or $-NR^{1a}CH(CH_3)CH_2-$;

$R^1$ is (i) hydrogen; or (ii) phenyl, furanyl, pyrrolyl, imidazolyl, pyrazolyl, thienyl, thiazolyl, pyridinyl, pyrimidinyl, pyrrolidinyl, pyrazinyl, pyridazinyl, benzoimidazolyl, isoquinolinyl, imidazopyridinyl, or benzothienyl, each of which is optionally substituted by one, two, or three substituents, where each substituent is independently cyano, halo, $C_{1-4}$ alkyl, $C_{1-4}$ alkoxy, $C_{1-4}$ haloalkyl, $C_{1-4}$ haloalkoxy, hydroxyl, amino, $-C(O)R^{1a}$, $-C(O)OR^{1a}$, $-C(O)NR^{1a}R^{1b}$, $-SR^{1a}$, $-S(O)R^{1a}$, or $-S(O)_2R^{1a}$;

$R^2$ is (i) $-NR^{1a}C(O)R^{1c}$, $-NR^{1c}C(O)NR^{1a}R^{1b}$, or $-S(O)_2NR^{1a}R^{1b}$; or (ii) phenyl, pyrrolopyridin-3-yl, indolyl, thienyl, pyridinyl, 1,2,4-triazolyl, 2-oxoimidazolidinyl, pyrazolyl, 2-oxo-2,3-dihydro-1H-benzoimidazolyl, or indazolyl, each of which is optionally substituted with one, two, or three substituents, where each substituent is independently hydroxyl, halo, methyl, methoxy, amino, $-O(CH_2)_{1-3}NR^{1a}R^{1b}$, $-OS(O)_2NR^{1a}R^{1b}$, $-NR^{1a}S(O)_2R^{1b}$, or $-S(O)_2NR^{1a}R^{1b}$;

$R^3$ is hydrogen, $C_{1-4}$ alkyl, or biphenyl; with the proviso that at least one of $R^1$ and $R^3$ is not hydrogen;

$R^4$ is $C_{1-10}$ alkyl, prop-1-en-2-yl, cyclohexyl, cyclopropyl, 2-(2-oxopyrrolidin-1-yl)ethyl, oxetan-3-yl, benzhydryl, tetrahydro-2H-pyran-3-yl, tetrahydro-2H-pyran-4-yl, phenyl, tetrahydrofuran-3-yl, benzyl, (4-pentylphenyl)(phenyl)methyl, or 1-(1-(2-oxo-6,9,12-trioxa-3-azatetradecan-14-yl)-1H-1,2,3-triazol-4-yl)ethyl, each of which is optionally substituted with one, two, or three substituents, where each substituent is independently hydroxyl, $C_{1-4}$ alkyl, or $C_{1-4}$ haloalkyl; and each $R^{1a}$, $R^{1b}$, and $R^{1c}$ is independently hydrogen or $C_{1-4}$ alkyl; or $R^{1a}$ and $R^{1b}$ together with the N atom to which they are attached form heterocyclyl.

In one embodiment, in Formula I, $G^1$ is $CR^3$, in one embodiment, CH; $G^2$, $G^3$, and $G^4$ are each N; and $R^1$, $R^2$, $R^3$, $R^4$, and $L^1$ are each as defined herein.

In another embodiment, in Formula I, $G^1$, $G^3$, and $G^4$ are each N; $G^2$ is CH; and $R^1$, $R^2$, $R^4$, and $L^1$ are each as defined herein.

In yet another embodiment, in Formula I, $G^1$ is $CR^3$, in one embodiment, CH; $G^2$ and $G^3$ are each N; $G^4$ is CH; and $R^1$, $R^2$, $R^3$, $R^4$, and $L^1$ are each as defined herein.

In yet another embodiment, in Formula I, $G^1$ is $CR^3$, in one embodiment, CH; $G^2$ and $G^4$ are each N; $G^3$ is CH; and $R^1$, $R^2$, $R^3$, $R^4$, and $L^1$ are each as defined herein.

In yet another embodiment, in Formula I, $G^1$ is $CR^3$, in one embodiment, CH; $G^2$ is CH; $G^3$ and $G^4$ are each N; and $R^1$, $R^2$, $R^3$, $R^4$, and $L^1$ are each as defined herein.

In still embodiment, in Formula I, $G^1$ is CH;

$G^2$, $G^3$, and $G^4$ are each N;

$R^1$ is benzothienyl, optionally substituted by one, two, or three substituents, each of which is independently cyano, halo, $C_{1-4}$ alkyl, $C_{1-4}$ alkoxy, $C_{1-4}$ haloalkyl, $C_{1-4}$ haloalkoxy, hydroxyl, amino, $-C(O)R^{1a}$, $-C(O)OR^{1a}$, $-C(O)NR^{1a}R^{1b}$, $-SR^{1a}$, $-S(O)R^{1a}$, or $-S(O)_2R^{1a}$;

$R^2$ is phenyl, optionally substituted with one, two, or three substituents, each of which is independently hydroxyl, halo, methyl, methoxy, amino, $-O(CH_2)_{1-3}NR^{1a}R^{1b}$, $-OS(O)_2NR^{1a}R^{1b}$, $-NR^{1a}S(O)_2R^{1b}$, or $-S(O)_2NR^{1a}R^{1b}$;

$R^4$ is $C_{1-10}$ alkyl, optionally substituted with one, two, or three substituents, each of which is independently hydroxyl, $C_{1-4}$ alkyl, or $C_{1-4}$ haloalkyl;

$L^1$ is $-NR^{1a}(CH_2)_2-$; and $R^{1a}$ and $R^{1b}$ are each as defined herein.

In yet another embodiment, the stem cell mobilizing compound is a compound of Formula II:

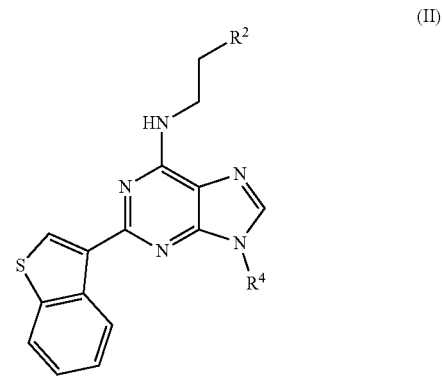

(II)

or an enantiomer, a mixture of enantiomers, a mixture of two or more diastereomers, or an isotopic variant thereof; or a pharmaceutically acceptable salt, solvate, hydrate, or prodrug thereof; wherein $R^2$ and $R^4$ are each as defined herein.

In yet another embodiment, the stem cell mobilizing compound is a compound of Formula III:

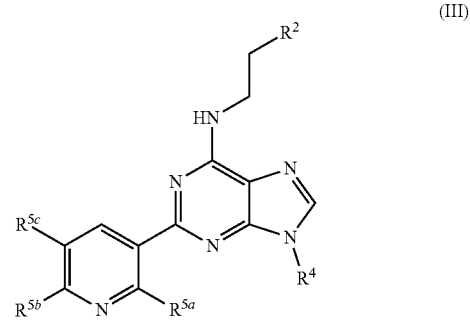

(III)

or an enantiomer, a mixture of enantiomers, a mixture of two or more diastereomers, or an isotopic variant thereof; or a pharmaceutically acceptable salt, solvate, hydrate, or prodrug thereof; wherein $R^2$ and $R^4$ are each as defined herein; and $R^{5a}$, $R^{5b}$, and $R^{5c}$ are each independently hydrogen, cyano, methyl, halo, trifluoromethyl, or $-SO_2CH_3$.

In yet another embodiment, the stem cell mobilizing compound is 4-(2-(2-(benzo[b]thien-3-yl)-9-isopropyl-9H-purin-6-ylamino)ethyl)phenol. In certain embodiments, the stem cell mobilizing compound is StemRegenin-1 (SR-1), having the structure of:

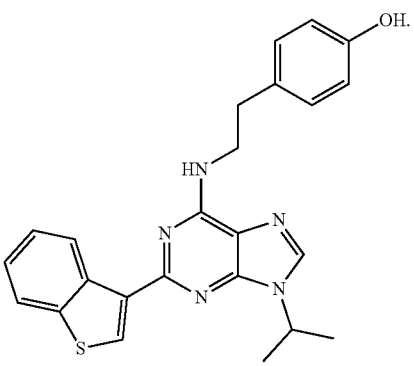 [SMILES: CC(C)n1cnc2c(NCCc3ccc(O)cc3)nc(-c3csc4ccccc34)nc21]

In yet another embodiment, the stem cell mobilizing compound is 1-methyl-N-(2-methyl-4-(2-(2-methylphenyl)diazenyl)phenyl)-1H-pyrazole-5-carboxamide. In certain embodiments, the stem cell mobilizing compound is CH223191, which has the structure of:

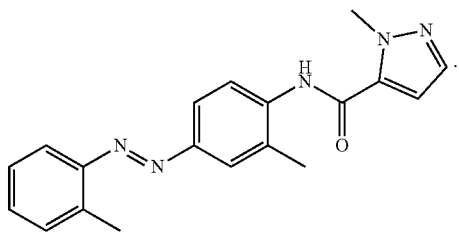 [SMILES: Cc1ccccc1/N=N/c1ccc(NC(=O)c2ccnn2C)c(C)c1]

In yet another embodiment, the stem cell mobilizing compound is a pyrimido(4,5-b)indole.

In yet another embodiment, the stem cell mobilizing compound is a compound of Formula IV:

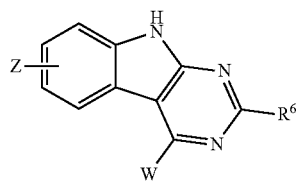

(IV)

or an enantiomer, a mixture of enantiomers, a mixture of two or more diastereomers, or an isotopic variant thereof; or a pharmaceutically acceptable salt, solvate, hydrate, or prodrug thereof; wherein:

Z is cyano, $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, benzyl, heteroaryl, heterocyclyl, -L-$C_{6-14}$ aryl, -L-heteroaryl, -L-heterocyclyl, —C(O)$R^{1a}$, —C(O)O$R^{1a}$, —C(O)NH$R^{1a}$, —C(O)N($R^{1a}$)$R^{1b}$, —P(O)(O$R^{1a}$)(O$R^{1c}$), —S$R^{1a}$, —S(O)$R^{1a}$, —S(O)$_2$$R^{1a}$, —S(O)$_2$NH$_2$, —S(O)$_2$NH$R^{1a}$, or —S(O)$_2$N($R^{1a}$)$R^{1b}$;

W is hydrogen, halo, cyano, $C_{6-14}$ aryl, benzyl, heteroaryl, heterocyclyl, -L-$C_{6-14}$ aryl, -L-heteroaryl, -L-heterocyclyl, -L-OH, -L-O$R^{1a}$, -L-NH$_2$, -L-NH$R^{1a}$, -L-N($R^{1a}$)$R^{1b}$, -L-S$R^{1a}$, -L-S(O)$R^{1a}$, -L-S(O)$_2$$R^{1a}$, -L-P(O)(O$R^{1a}$)(O$R^{1c}$), -L-(N($R^{1c}$)-L)$_n$-N($R^{1a}$)$R^{1b}$, -L-(N($R^{1c}$)-L)$_n$-$C_{6-14}$ aryl, -L(N($R^{1c}$)-L)$_n$-heteroaryl, -L-(N($R^{1c}$)-L)$_n$-heterocyclyl, —O-L-$C_{6-14}$ aryl, —O-L-heteroaryl, —O-L-N($R^{1a}$)$R^{1b}$, —O-L-(N(R)-L)$_n$-N($R^{1a}$)$R^{1b}$, —O-L-(N($R^{1c}$)-L)$_n$-$C_{6-14}$ aryl, —O-L-(N($R^{1c}$)-L)$_n$-heteroaryl, —O-L-(N($R^{1c}$)-L)$_n$-heterocyclyl, —S-L-N($R^{1a}$)$R^{1b}$, —S-L-$C_{6-14}$ aryl, —S-L-heteroaryl, —S-L-heterocyclyl, —S-L-(N($R^{1c}$-L)$_n$-N($R^{1a}$)$R^{1b}$, —S-L-(N($R^{1c}$)-L)-$C_{6-14}$ aryl, —S-L-(N($R^{1c}$)-L)-heteroaryl, —S-L-(N($R^{1c}$)-L)$_n$-heterocyclyl, N($R^{1c}$)-L)$_n$-N($R^{1a}$)$R^{1b}$, —(N($R^{1c}$)-L)$_n$-$C_{6-14}$ aryl, —(N($R^{1c}$)-L)$_n$-heteroaryl, —(N($R^{1c}$)-L)$_n$-heterocyclyl, —C(O)$R^{1a}$, —C(O)O$R^{1a}$, —C(O)NH$_2$, —C(O)NH$R^{1a}$, —C(O)N($R^{1a}$)$R^{1b}$, —NH$R^{1a}$, —N($R^{1a}$)$R^{1b}$, —NHC(O)$R^{1a}$, —N$R^{1a}$C(O)$R^{1c}$, —NHC(O)O$R^{1a}$, —N$R^{1a}$C(O)O$R^{1c}$, —NHC(O)NH$_2$, —NHC(O)NH$R^{1a}$, —NHC(O)N($R^{1a}$)$R^{1b}$, —N$R^{1a}$C(O)NH$_2$, —N$R^{1c}$C(O)NH$R^{1a}$, —N$R^{1c}$C(O)N($R^{1a}$)$R^{1b}$, —NHS(O)$_2$$R^{1a}$, —N$R^{1c}$S(O)$_2$$R^{1a}$, —O$R^{1a}$, —OC(O)$R^{1a}$, —OC(O)O$R^{1a}$, —OC(O)NH$_2$, —OC(O)NH$R^{1a}$, —OC(O)N($R^{1a}$)$R^{1b}$, —OS(O)$_2$$R^{1a}$, —P(O)(O$R^{1a}$)(O$R^{1c}$), —S$R^{1a}$, —S(O)$R^{1a}$, —S(O)$_2$$R^{1a}$, —S(O)$_2$NH$_2$, —S(O)$_2$NH$R^{1a}$, —S(O)$_2$N($R^{1a}$)$R^{1b}$, or —S(O)$_2$O$R^{1a}$;

each L is independently $C_{1-6}$ alkylene, $C_{2-6}$ alkenylene, $C_{2-6}$ alkynylene, $C_{3-7}$ cycloalkylene, $C_{6-14}$ arylene, heteroarylene, heterocyclylene, $C_{1-6}$ alkylene-$C_{3-7}$ cycloalkylene, or $C_{1-6}$ alkylene-heterocyclylene;

$R^6$ is hydrogen, $C_{1-6}$ alkyl, $C_{6-14}$ aryl, benzyl, heteroaryl, —C(O)$R^{1a}$, —S$R^{1a}$, —S(O)$R^{1a}$, —S(O)$_2$$R^{1a}$, -L-$C_{6-14}$ aryl, -L-heteroaryl, or -L-heterocyclyl;

each n is independently an integer of 1, 2, 3, 4, or 5; and each $R^{1a}$, $R^{1b}$, and $R^{1c}$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl; or (iii) $R^{1a}$ and $R^{1b}$ together with the N atom to which they are attached form heterocyclyl;

wherein each alkyl, alkylene, alkenyl, alkenylene, alkynyl, alkynylene, cycloalkyl, cycloalkylene, aryl, benzyl, arylene, heteroaryl, heteroarylene, heterocyclyl, and heterocyclylene is optionally substituted with one or more, in one embodiment, one, two, three, or four, substituents Q, wherein each substituent Q is independently selected from (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b$$R^c$, —C(N$R^a$)N$R^b$$R^c$, —O$R^a$, —OC(O)$R^a$, —OC(O)O$R^a$, —OC(O)N$R^b$$R^c$, —OC(=NR)N$R^b$$R^c$, —OS(O)$R^a$, —OS(O)$_2$$R^a$, —OS(O)N$R^b$$R^c$, —OS(O)$_2$N$R^b$$R^c$, —N$R^b$$R^c$, —N$R^a$C(O)$R^d$, —N$R^a$C(O)O$R^d$, —N$R^a$C(O)N$R^b$$R^c$, —N$R^a$C(=N$R^d$)N$R^b$$R^c$, —N$R^a$S(O)$R^d$, —N$R^a$S(O)$_2$$R^d$, —N$R^a$S(O)N$R^b$$R^c$, —N$R^a$S(O)$_2$N$R^b$$R^c$, —S$R^a$, —S(O)$R^a$, —S(O)$_2$$R^a$, —S(O)N$R^b$$R^c$, and —S(O)$_2$N$R^b$$R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is further optionally substituted with one or more, in one embodiment, one, two, three, or four, substituents $Q^a$; or (iii) $R^b$ and $R^c$ together with the N atom to which they are attached form heterocyclyl, which is further optionally substituted with one or more, in one embodiment, one, two, three, or four, substituents $Q^a$;

wherein each $Q^a$ is independently selected from the group consisting of (a) oxo, cyano, halo, and nitro; (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f$$R^g$, —C(N$R^e$)N$R^f$$R^g$, —O$R^e$, —OC(O)$R^e$, —OC(O)O$R^e$, —OC(O)N$R^f$$R^g$, —OC(=N$R^e$)N$R^f$$R^g$, —OS(O)$R^e$, —OS(O)$_2$$R^e$, —OS(O)N$R^f$$R^g$, —OS(O)$_2$N$R^f$$R^g$, —N$R^f$$R^g$, —N$R^e$C(O)$R^h$, —N$R^e$C(O)O$R^h$, —N$R^e$C(O)N$R^f$$R^g$, —N$R^e$C(=N$R^h$)N$R^f$$R^g$, —N$R^e$S(O)$R^h$, —N$R^e$S(O)$_2$$R^h$, —N$R^e$S(O)N$R^f$$R^g$, —N$R^e$S(O)$_2$N$R^f$$R^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (iii) R$^f$ and R$^g$ together with the N atom to which they are attached form heterocyclyl.

In yet another embodiment, the stem cell mobilizing compound is a compound of Formula V:

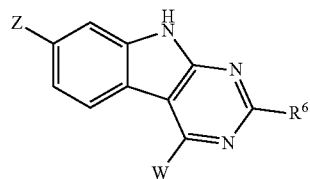

(V)

or an enantiomer, a mixture of enantiomers, a mixture of two or more diastereomers, or an isotopic variant thereof; or a pharmaceutically acceptable salt, solvate, hydrate, or prodrug thereof; wherein R$^6$, W, and Z are each as defined herein.

In one embodiment, in Formula IV or V,

Z is cyano, heteroaryl, or —C(O)OR$^{1a}$;

W is heterocyclyl, -L-heterocyclyl, —O-L-heterocyclyl, —(N(R$^{1c}$)-L)$_n$-N(R$^{1a}$)R$^{1b}$, —(N(R$^{1c}$)-L)$_n$-heterocyclyl, —NHR$^{1a}$, or —N(R$^{1a}$)R$^{1b}$;

each L is independently C$_{1-6}$ alkylene or C$_{3-7}$ cycloalkylene;

R$^6$ is hydrogen, C$_{1-6}$ alkyl, benzyl, —C(O)R$^{1a}$, -L-C$_{6-14}$ aryl, or -L-heteroaryl;

each n is independently an integer of 1; and

R$^{1a}$, R$^{1b}$, and R$^{1c}$ are each as defined herein;

wherein each alkyl, alkylene, cycloalkylene, aryl, benzyl, heteroaryl, and heterocyclyl is optionally substituted with one or more substituents Q as defined herein.

In another embodiment, in Formula IV or V,

Z is cyano, 5-membered heteroaryl, or —C(O)O—C$_{1-6}$ alkyl;

W is heterocyclyl, -L-heterocyclyl, —O-L-heterocyclyl, —(N(R$^{1c}$)-L)$_n$-N(R$^{1a}$)R$^{1b}$, —(N(R$^{1c}$)-L)$_n$-heterocyclyl, —NHR$^{1a}$, or —N(R$^{1a}$)R$^{1b}$;

each L is independently C$_{1-6}$ alkylene or C$_{3-7}$ cycloalkylene;

R$^6$ is hydrogen, methyl, benzyl, -L-C$_{6-14}$ aryl, or -L-heteroaryl;

each n is independently an integer of 1; and

R$^{1a}$, R$^{1b}$, and R$^{1c}$ are each as defined herein;

wherein each alkylene, cycloalkylene, aryl, benzyl, heteroaryl, and heterocyclyl is optionally substituted with one or more substituents Q as defined herein.

In one embodiment, in Formula IV or V, W is -L-N(R$^{1a}$)R$^{1b}$, -L-(N(R$^{1c}$)-L)$^n$-N(R$^{1a}$)R$^{1b}$, —O-L-N(R$^{1a}$)R$^{1b}$, —O-L-(N(R$^{1c}$)-L)$_n$-N(R$^{1a}$)R$^{1b}$, —S-L-N(R$^{1a}$)R$^{1b}$, —S-L-(N(R$^{1c}$)-L)$_n$-N(R$^{1a}$)R$^{1b}$, or —(N(R$^{1c}$)-L)$_n$-N(R$^{1a}$)R$^{1b}$; and R$^6$, R$^{1a}$, R$^{1b}$, R$^{1c}$, L, and Z are each as defined herein.

In yet another embodiment, the stem cell mobilizing compound is a compound of Formula VI:

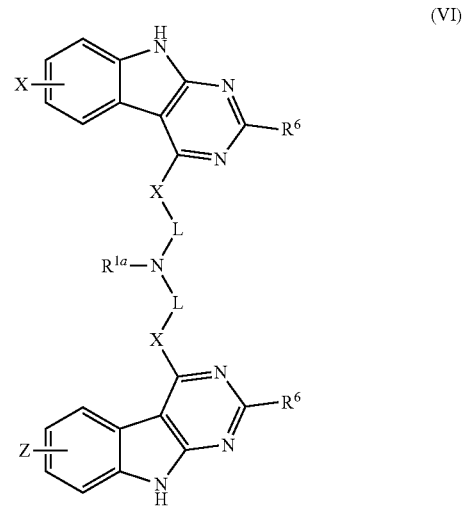

(VI)

or an enantiomer, a mixture of enantiomers, a mixture of two or more diastereomers, or an isotopic variant thereof, or a pharmaceutically acceptable salt, solvate, hydrate, or prodrug thereof, wherein X is a bond, O, S, or NR$^{1c}$; and R$^{1a}$, R$^{1c}$, R$^6$, L, and Z are each as defined herein.

In still another embodiment, the stem cell mobilizing compound is a compound of Formula VII:

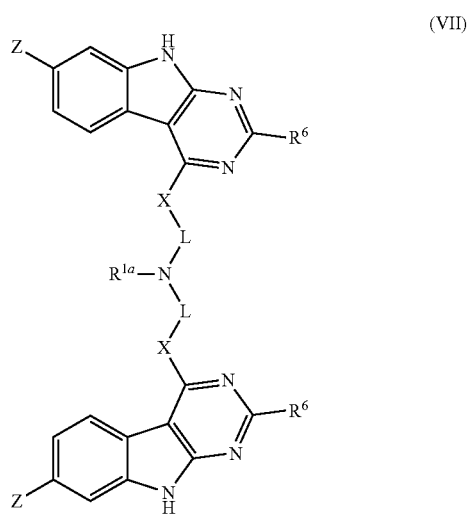

(VII)

or an enantiomer, a mixture of enantiomers, a mixture of two or more diastereomers, or an isotopic variant thereof; or a pharmaceutically acceptable salt, solvate, hydrate, or prodrug thereof; wherein R$^{1a}$, R$^6$, L, X, and Z are each as defined herein.

In yet another embodiment, the stem cell mobilizing compound is a compound having the structure of:

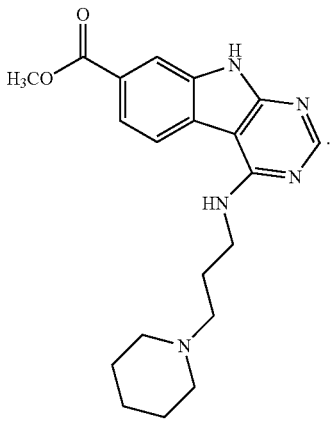

(UM729)

In yet another embodiment, the stem cell mobilizing compound is a compound having the structure of:

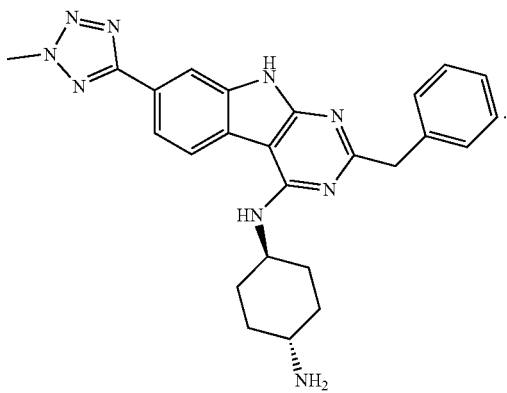

(UM171)

In yet another embodiment, the stem cell mobilizing compound is resveratrol, tetraethylenepentamine (TEPA), alpha naphthoflavone, 3'-methoxy-4'-nitroflavone, 3,4-dimethoxyflavone, 4',5,7-trihydroxyflavone (apigenin), 6-methyl-1,3,8-trichlorodibenzofuran, epigallocatechin, or epigallocatechingallate.

In yet another embodiment, the stem cell mobilizing compound is resveratrol. In certain embodiments, the stem cell mobilizing compound is (Z)-resveratrol. In certain embodiments, the stem cell mobilizing compound is (E)-resveratrol.

In still another embodiment, the stem cell mobilizing compound is tetraethylenepentamine (TEPA).

All of the compounds described herein are either commercially available or can be prepared according to the methods described in the patents or patent publications disclosed herein. Further, optically pure compounds can be asymmetrically synthesized or resolved using known resolving agents or chiral columns as well as other standard synthetic organic chemistry techniques. Additional information on stem cell mobilizing compounds, their preparation, and use can be found, for example, in U.S. Pat. App. Pub. Nos. 2010/0183564, 2014/0023626, and 2014/0114070; and Kim et al., *Mol. Pharmacol.*, 2006, 69, 1871-1878; the disclosure of each of which is incorporated by reference herein in its entirety.

The groups or variables, $G^1$, $G^2$, $G^3$, $G^4$, $R^1$, $R^2$, $R^3$, $R^4$, $R^{5a}$, $R^{5b}$, $R^{5c}$, $R^6$, X, L, $L^1$, X, W, Z, and n, in Formulae provided herein, e.g., Formulae I to VII, are further defined in the embodiments described herein. All combinations of the embodiments provided herein for such groups and/or variables are within the scope of this disclosure.

In certain embodiments, $G^1$ is N. In certain embodiments, $G^1$ is $CR^3$, wherein $R^3$ is as defined herein. In certain embodiments, $G^1$ is CH.

In certain embodiments, $G^2$ is N. In certain embodiments, $G^2$ is CH.

In certain embodiments, $G^3$ is N. In certain embodiments, $G^3$ is CH.

In certain embodiments, $G^4$ is N. In certain embodiments, $G^4$ is CH.

In certain embodiments, $R^1$ is hydrogen. In certain embodiments, $R^1$ is phenyl optionally substituted as described herein. In certain embodiments, $R^1$ is furanyl optionally substituted as described herein. In certain embodiments, $R^1$ is pyrrolyl optionally substituted as described herein. In certain embodiments, $R^1$ is imidazolyl optionally substituted as described herein. In certain embodiments, $R^1$ is pyrazolyl optionally substituted as described herein. In certain embodiments, $R^1$ is thienyl optionally substituted as described herein. In certain embodiments, $R^1$ is thiazolyl optionally substituted as described herein. In certain embodiments, $R^1$ is pyridinyl optionally substituted as described herein. In certain embodiments, $R^1$ is pyrimidinyl optionally substituted as described herein. In certain embodiments, $R^1$ is pyrrolidinyl optionally substituted as described herein. In certain embodiments, $R^1$ is pyrazinyl optionally substituted as described herein. In certain embodiments, $R^1$ is pyridazinyl optionally substituted as described herein. In certain embodiments, $R^1$ is benzoimidazolyl optionally substituted as described herein. In certain embodiments, $R^1$ is isoquinolinyl optionally substituted as described herein. In certain embodiments, $R^1$ is imidazopyridinyl optionally substituted as described herein. In certain embodiments, $R^1$ is benzothienyl optionally substituted as described herein.

In certain embodiments, $R^2$ is $-NR^{1a}C(O)R^{1c}$, wherein $R^{1a}$ and $R^{1c}$ are each as defined herein. In certain embodiments, $R^2$ is $-NR^{1c}C(O)NR^{1a}R^{1b}$, wherein $R^{1a}$, $R^{1b}$, and $R^{1c}$ are each as defined herein. In certain embodiments, $R^2$ is $-S(O)_2NR^{1a}R^{1b}$, wherein $R^{1a}$ and $R^{1b}$ are each as defined herein. In certain embodiments, $R^2$ is phenyl optionally substituted as described herein. In certain embodiments, $R^2$ is pyrrolopyridin-3-yl optionally substituted as described herein. In certain embodiments, $R^2$ is indolyl optionally substituted as described herein. In certain embodiments, $R^2$ is thienyl optionally substituted as described herein. In certain embodiments, $R^2$ is pyridinyl optionally substituted as described herein. In certain embodiments, $R^2$ is 1,2,4-triazolyl optionally substituted as described herein. In certain embodiments, $R^2$ is 2-oxoimidazolidinyl optionally substituted as described herein. In certain embodiments, $R^2$ is pyrazolyl optionally substituted as described herein. In certain embodiments, $R^2$ is 2-oxo-2,3-dihydro-1H-benzoimidazolyl optionally substituted as described herein. In certain embodiments, $R^2$ is indazolyl optionally substituted as described herein.

In certain embodiments, $R^3$ is hydrogen. In certain embodiments, $R^3$ is $C_{1-4}$ alkyl, optionally substituted with one or more substituents Q as described herein. In certain embodiments, $R^3$ is biphenyl, optionally substituted with one or more substituents Q as described herein.

In certain embodiments, $R^4$ is $C_{1-10}$ alkyl optionally substituted as described herein. In certain embodiments, $R^4$ is prop-1-en-2-yl optionally substituted as described herein. In certain embodiments, $R^4$ is cyclohexyl optionally substituted as described herein. In certain embodiments, $R^4$ is cyclopropyl optionally substituted as described herein. In certain embodiments, $R^4$ is 2-(2-oxopyrrolidin-1-yl)ethyl optionally substituted as described herein. In certain embodiments, $R^4$ is oxetan-3-yl optionally substituted as described herein. In certain embodiments, $R^4$ is benzhydryl optionally substituted as described herein. In certain embodiments, $R^4$ is tetrahydro-2H-pyran-3-yl optionally substituted as described herein. In certain embodiments, $R^4$ is tetrahydro-2H-pyran-4-yl optionally substituted as described herein. In certain embodiments, $R^4$ is phenyl optionally substituted as described herein. In certain embodiments, $R^4$ is tetrahydrofuran-3-yl optionally substituted as described herein. In certain embodiments, $R^4$ is benzyl optionally substituted as described herein. In certain embodiments, $R^4$ is (4-pentylphenyl)(phenyl)methyl optionally substituted as described herein. In certain embodiments, $R^4$ is 1-(1-(2-oxo-6,9,12-trioxa-3-azatetradecan-14-yl)-1H-1,2,3-triazol-4-yl)ethyl optionally substituted as described herein.

In certain embodiments, $L^1$ is $-NR^{1a}-$, wherein $R^{1a}$ is as defined herein. In certain embodiments, $L^1$ is $-NR^{1a}(CH_2)_{1-3}-$, wherein $R^{1a}$ is as defined herein. In certain embodiments, L is $-NR^{1a}CH(C(O)OCH_3)CH_2-$, wherein $R^{1a}$ is as defined herein. In certain embodiments, $L^1$ is $-NR^{1a}(CH_2)_2NR^{1c}-$, wherein $R^{1a}$ and $R^{1c}$ are each as defined herein. In certain embodiments, L is $-NR^{1a}(CH_2)_2S-$, wherein $R^{1a}$ is as defined herein. In certain embodiments, $L^1$ is $-NR^{1a}CH_2CH(CH_3)CH_2-$, wherein $R^{1a}$ is as defined herein. In certain embodiments, $L^1$ is $-NR^{1a}CH_2CH(OH)-$, wherein $R^{1a}$ is as defined herein. In certain embodiments, $L^1$ is $-NR^{1a}CH(CH_3)CH_2-$, wherein $R^{1a}$ is as defined herein.

In certain embodiments, $R^{5a}$ is hydrogen. In certain embodiments, $R^{5a}$ is cyano. In certain embodiments, $R^{5a}$ is methyl. In certain embodiments, $R^{5a}$ is halo. In certain embodiments, $R^{5a}$ is fluoro, chloro, or bromo. In certain embodiments, $R^{5a}$ is trifluoromethyl. In certain embodiments, $R^{5a}$ is $-SO_2CH_3$.

In certain embodiments, $R^{5b}$ is hydrogen. In certain embodiments, $R^{5b}$ is cyano. In certain embodiments, $R^{5b}$ is methyl. In certain embodiments, $R^{5b}$ is halo. In certain embodiments, $R^{5b}$ is fluoro, chloro, or bromo. In certain embodiments, $R^{5b}$ is trifluoromethyl. In certain embodiments, $R^{5b}$ is $-SO_2CH_3$.

In certain embodiments, $R^{5c}$ is hydrogen. In certain embodiments, $R^{5c}$ is cyano. In certain embodiments, $R^{5c}$ is methyl. In certain embodiments, $R^{5c}$ is halo. In certain embodiments, $R^{5c}$ is fluoro, chloro, or bromo. In certain embodiments, $R^{5c}$ is trifluoromethyl. In certain embodiments, $R^{5c}$ is $-SO_2CH_3$.

In certain embodiments, L is $C_{1-6}$ alkylene, optionally substituted with one or more substituents Q as described herein. In certain embodiments, L is ethylene, propylene, or butylenes, each optionally substituted with one or more substituents Q as described herein. In certain embodiments, L is $C_{2-6}$ alkenylene, optionally substituted with one or more substituents Q as described herein. In certain embodiments, L is $C_{2-6}$ alkynylene, optionally substituted with one or more substituents Q as described herein. In certain embodiments, L is $C_{3-7}$ cycloalkylene, optionally substituted with one or more substituents Q as described herein. In certain embodiments, L is cyclohexylene, optionally substituted with one or more substituents Q as described herein. In certain embodiments, L is $C_{6-14}$ arylene, optionally substituted with one or more substituents Q as described herein. In certain embodiments, L is heteroarylene, optionally substituted with one or more substituents Q as described herein. In certain embodiments, L is heterocyclylene, optionally substituted with one or more substituents Q as described herein. In certain embodiments, L is $C_{1-6}$ alkylene-$C_{3-7}$ cycloalkylene, optionally substituted with one or more substituents Q as described herein. In certain embodiments, L is $C_{1-6}$ alkylene-heterocyclylene, optionally substituted with one or more substituents Q as described herein.

In certain embodiments, $R^6$ is hydrogen. In certain embodiments, $R^6$ is $C_{1-6}$ alkyl, optionally substituted with one or more substituents Q as described herein. In certain embodiments, $R^6$ is methyl, optionally substituted with one or more substituents Q as described herein. In certain embodiments, $R^6$ is $C_{6-14}$ aryl, optionally substituted with one or more substituents Q as described herein. In certain embodiments, $R^6$ is benzyl, optionally substituted with one or more substituents Q as described herein. In certain embodiments, $R^6$ is heteroaryl, optionally substituted with one or more substituents Q as described herein. In certain embodiments, $R^6$ is $-C(O)R^{1a}$, where $R^{1a}$ is as defined herein. In certain embodiments, $R^6$ is $-SR^{1a}$, where $R^{1a}$ is as defined herein. In certain embodiments, $R^6$ is $-S(O)R^{1a}$, where $R^{1a}$ is as defined herein. In certain embodiments, $R^6$ is $-S(O)_2R^{1a}$, where $R^{1a}$ is as defined herein. In certain embodiments, $R^6$ is -L-$C_{6-14}$ aryl, where L is as defined herein. In certain embodiments, $R^6$ is -L-heteroaryl, where L is as defined herein. In certain embodiments, $R^6$ is or -L-heterocyclyl, where L is as defined herein.

In certain embodiments, W is hydrogen. In certain embodiments, W is halo. In certain embodiments, W is cyano. In certain embodiments, W is $C_{6-14}$ aryl, optionally substituted with one or more substituents Q as described herein. In certain embodiments, W is benzyl, optionally substituted with one or more substituents Q as described herein. In certain embodiments, W is heteroaryl, optionally substituted with one or more substituents Q as described herein. In certain embodiments, W is heterocyclyl, optionally substituted with one or more substituents Q as described herein.

In certain embodiments, W is -L-$C_{6-14}$ aryl, optionally substituted with one or more substituents Q as described herein, where L is as defined herein. In certain embodiments, W is -L-heteroaryl, optionally substituted with one or more substituents Q as described herein, where L is as defined herein. In certain embodiments, W is -L-heterocyclyl, optionally substituted with one or more substituents Q as described herein, where L is as defined herein. In certain embodiments, W is -L-OH, where L is as defined herein. In certain embodiments, W is -L-$OR^{1a}$, where $R^{1a}$ and L are each as defined herein. In certain embodiments, W is -L-$NH_2$, where L is as defined herein. In certain embodiments, W is -L-$NHR^{1a}$, where $R^{1a}$ and L are each as defined herein. In certain embodiments, W is -L-$N(R^{1a})R^{1b}$, where $R^{1a}$, $R^{1b}$, and L are each as defined herein. In certain embodiments, W is -L-$SR^{1a}$, where $R^{1a}$ and L are each as defined herein. In certain embodiments, W is -L-$S(O)R^{1a}$, where $R^{1a}$ and L are each as defined herein. In certain embodiments, W is -L-$S(O)_2R^{1a}$, where $R^{1a}$ and L are each as defined herein. In certain embodiments, W is -L-$P(O)(OR^{1a})(OR^{1c})$, where $R^{1a}$, $R^{1c}$, and L are each as defined herein.

In certain embodiments, W is -L-(N($R^{1c}$)-L)$_n$-N($R^{1a}$)$R^{1b}$, where $R^{1a}$, $R^{1b}$, $R^{1c}$, L and n are each as defined herein. In certain embodiments, W is -L-(N($R^{1c}$)-L)$_n$-$C_{6-14}$ aryl, optionally substituted with one or more substituents Q as described herein, where $R^{1c}$, L, and n are each as defined herein. In certain embodiments, W is -L-(N($R^{1c}$)-L)$_n$-heteroaryl, optionally substituted with one or more substituents Q as described herein, where $R^{1c}$, L, and n are each as defined herein. In certain embodiments, W is -L-(N($R^{1c}$)-L)$_n$-heterocyclyl, optionally substituted with one or more substituents Q as described herein, where $R^{1c}$, L, and n are each as defined herein.

In certain embodiments, W is —O-L-N($R^{1a}$)$R^{1b}$, where $R^{1a}$, $R^{1b}$, and L are each as defined herein. In certain embodiments, W is —O-L-$C_{6-14}$ aryl, optionally substituted with one or more substituents Q as described herein, where L is as defined herein. In certain embodiments, W is —O-L-heteroaryl, optionally substituted with one or more substituents Q as described herein, where L is as defined herein. In certain embodiments, W is —O-L-heterocyclyl, optionally substituted with one or more substituents Q as described herein, where L is as defined herein.

In certain embodiments, W is —O-L-(N($R^{1c}$)-L)$_n$-N($R^{1a}$)$R^{1b}$, where $R^{1a}$, $R^{1b}$, $R^{1c}$, L, and n are each as defined herein. In certain embodiments, W is —O-L-(N($R^{1c}$)-L)$_n$-$C_{6-14}$ aryl, optionally substituted with one or more substituents Q as described herein, where $R^{1c}$, L, and n are each as defined herein. In certain embodiments, W is —O-L-(N($R^{1c}$)-L)$_n$-heteroaryl, optionally substituted with one or more substituents Q as described herein, where $R^{1c}$, L, and n are each as defined herein. In certain embodiments, W is —O-L-(N($R^{1c}$)-L)-heterocyclyl, optionally substituted with one or more substituents Q as described herein, where $R^{1c}$, L, and n are each as defined herein.

In certain embodiments, W is —S-L-N($R^{1a}$)$R^{1b}$, where $R^{1a}$, $R^{1b}$, and L are each as defined herein. In certain embodiments, W is —S-L-$C_{6-14}$ aryl, optionally substituted with one or more substituents Q as described herein, where L is as defined herein. In certain embodiments, W is —S-L-heteroaryl, optionally substituted with one or more substituents Q as described herein, where L is as defined herein. In certain embodiments, W is —S-L-heterocyclyl, optionally substituted with one or more substituents Q as described herein, where L is as defined herein.

In certain embodiments, W is —S-L-(N($R^{1c}$)-L)$_n$-N($R^{1a}$)$R^{1b}$, where $R^{1a}$, $R^{1b}$, $R^{1c}$, L, and n are each as defined herein. In certain embodiments, W is —S-L-(N($R^{1c}$)-L)$_n$-$C_{6-14}$ aryl, optionally substituted with one or more substituents Q as described herein, where $R^{1c}$, L, and n are each as defined herein. In certain embodiments, W is —S-L-(N($R^{1c}$)-L)-heteroaryl, optionally substituted with one or more substituents Q as described herein, where $R^{1c}$, L, and n are each as defined herein. In certain embodiments, W is —S-L-(N($R^{1c}$)-L)-heterocyclyl, optionally substituted with one or more substituents Q as described herein, where $R^{1c}$, L, and n are each as defined herein.

In certain embodiments, W is —(N($R^{1c}$)-L)$_n$-N($R^{1a}$)$R^{1b}$, where $R^{1a}$, $R^{1b}$, $R^{1c}$, L, and n are each as defined herein. In certain embodiments, W is —(N($R^{1c}$)-L)$_n$-$C_{6-14}$ aryl, optionally substituted with one or more substituents Q as described herein, where $R^{1c}$, L, and n are each as defined herein. In certain embodiments, W is —(N($R^{1c}$)-L)$_n$-heteroaryl, optionally substituted with one or more substituents Q as described herein, where $R^{1c}$, L, and n are each as defined herein. In certain embodiments, W is —(N($R^{1c}$)-L)$_n$-heterocyclyl, optionally substituted with one or more substituents Q as described herein, where $R^{1c}$, L, and n are each as defined herein.

In certain embodiments, W is —C(O)$R^{1a}$, where $R^{1a}$ is as defined herein. In certain embodiments, W is —C(O)O$R^{1a}$, where $R^{1a}$ is as defined herein. In certain embodiments, W is —C(O)NH$_2$. In certain embodiments, W is —C(O)NH$R^{1a}$, where $R^{1a}$ is as defined herein. In certain embodiments, W is —C(O)N($R^{1a}$)$R^{1b}$, where $R^{1a}$ and $R^{1b}$ are each as defined herein. In certain embodiments, W is —NH$R^{1a}$, where $R^{1a}$ is as defined herein. In certain embodiments, W is —N($R^{1a}$)$R^{1b}$, where $R^{1a}$ and $R^{1b}$ are each as defined herein. In certain embodiments, W is —NHC(O)$R^{1a}$, where $R^{1a}$ is as defined herein. In certain embodiments, W is —N$R^{1a}$C(O)$R^{1c}$, where $R^{1a}$ and $R^{1c}$ are each as defined herein. In certain embodiments, W is —NHC(O)O$R^{1a}$, where $R^{1a}$ is as defined herein. In certain embodiments, W is —N$R^{1a}$C(O)O$R^{1c}$, where $R^{1a}$ and $R^{1c}$ are each as defined herein. In certain embodiments, W is —NHC(O)NH$_2$. In certain embodiments, W is —NHC(O)NH$R^{1a}$, where $R^{1a}$ is as defined herein. In certain embodiments, W is —NHC(O)N($R^{1a}$)$R^{1b}$, where $R^{1a}$ and $R^{1b}$ are each as defined herein. In certain embodiments, W is —N$R^{1a}$C(O)NH$_2$, where $R^{1a}$ is as defined herein. In certain embodiments, W is —N$R^{1c}$C(O)NH$R^{1a}$, where $R^{1a}$ and $R^{1c}$ are each as defined herein. In certain embodiments, W is —N$R^{1c}$C(O)N($R^{1a}$)$R^{1b}$, where $R^{1a}$, $R^{1b}$, and $R^{1c}$ are each as defined herein. In certain embodiments, W is —NHS(O)$_2$$R^{1a}$, where $R^{1a}$ is as defined herein. In certain embodiments, W is —N$R^{1c}$S(O)$_2$$R^{1a}$, where $R^{1a}$ and $R^{1c}$ are each as defined herein. In certain embodiments, W is —O$R^{1a}$, where $R^{1a}$ is as defined herein. In certain embodiments, W is —OC(O)$R^{1a}$, where $R^{1a}$ is as defined herein. In certain embodiments, W is —OC(O)O$R^{1a}$, where $R^{1a}$ is as defined herein. In certain embodiments, W is —OC(O)NH$_2$. In certain embodiments, W is —OC(O)NH$R^{1a}$, where $R^{1a}$ is as defined herein. In certain embodiments, W is —OC(O)N($R^{1a}$)$R^{1b}$, where $R^{1a}$ and $R^{1b}$ are each as defined herein. In certain embodiments, W is —OS(O)$_2$$R^{1a}$, where $R^{1a}$ is as defined herein. In certain embodiments, W is —P(O)(O$R^{1a}$)(O$R^{1c}$), where $R^{1a}$ and $R^{1c}$ are each as defined herein. In certain embodiments, W is —S$R^{1a}$, where $R^{1a}$ is as defined herein. In certain embodiments, W is —S(O)$R^{1a}$, where $R^{1a}$ is as defined herein. In certain embodiments, W is —S(O)$_2$$R^{1a}$, where $R^{1a}$ is as defined herein. In certain embodiments, W is —S(O)$_2$NH$_2$. In certain embodiments, W is —S(O)$_2$NH$R^{1a}$, where $R^{1a}$ is as defined herein. In certain embodiments, W is —S(O)$_2$N($R^{1a}$)$R^{1b}$, where $R^{1a}$ and $R^{1b}$ are each as defined herein. In certain embodiments, W is —S(O)$_2$O$R^a$, where $R^{1a}$ is as defined herein.

In certain embodiments, Z is cyano. In certain embodiments, Z is $C_{1-6}$ alkyl, optionally substituted with one or more substituents Q as described herein. In certain embodiments, Z is $C_{2-6}$ alkenyl, optionally substituted with one or more substituents Q as described herein. In certain embodiments, Z is $C_{2-6}$ alkynyl, optionally substituted with one or more substituents Q as described herein. In certain embodiments, Z is $C_{3-10}$ cycloalkyl, optionally substituted with one or more substituents Q as described herein. In certain embodiments, Z is $C_{6-14}$ aryl, optionally substituted with one or more substituents Q as described herein. In certain embodiments, Z is $C_{7-15}$ aralkyl, optionally substituted with one or more substituents Q as described herein. In certain embodiments, Z is benzyl, optionally substituted with one or more substituents Q as described herein. In certain embodiments, Z is heteroaryl, optionally substituted with one or more substituents Q as described herein. In certain embodiments, Z is 5-membered heteroaryl, optionally substituted with one or more substituents Q as described herein. In certain embodiments, Z is tetrazolyl, optionally substituted with one or more substituents Q as described herein. In certain embodiments, Z is 1,2,4-oxadiazolyl, optionally substituted with one or more substituents Q as described herein. In certain embodiments, Z is heterocyclyl, optionally substituted with one or more substituents Q as described herein. In certain embodiments, Z is -L-$C_{6-14}$ aryl, optionally substituted with one or more substituents Q as described herein, where L is as defined herein. In certain embodiments, Z is -L-heteroaryl, optionally substituted with one or more substituents Q as described herein, where L is as defined herein. In certain embodiments, Z is -L-heterocyclyl, optionally substituted with one or more substituents Q as described herein, where L is as defined herein.

In certain embodiments, Z is —C(O)$R^{1a}$, wherein $R^{1a}$ is as defined herein. In certain embodiments, Z is —C(O)O$R^{1a}$, wherein $R^{1a}$ is as defined herein. In certain embodiments, Z is —C(O)O$C_{1-6}$ alkyl, wherein the alkyl is optionally substituted with one or more substituents Q as defined herein. In certain embodiments, Z is —C(O)O$CH_3$. In certain embodiments, Z is —C(O)NH$R^{1a}$, wherein $R^{1a}$ is as defined herein. In certain embodiments, Z is —C(O)N($R^{1a}$)$R^{1b}$, wherein $R^{1a}$ and $R^{1b}$ are each as defined herein. In certain embodiments, Z is —P(O)(O$R^{1a}$)(O$R^{1c}$), wherein $R^{1a}$ and $R^{1c}$ are each as defined herein. In certain embodiments, Z is —S$R^{1a}$, wherein $R^{1a}$ is as defined herein. In certain embodiments, Z is —S(O)$R^{1a}$, wherein $R^{1a}$ is as defined herein. In certain embodiments, Z is —S(O)$_2R^{1a}$, wherein $R^{1a}$ is as defined herein. In certain embodiments, Z is —S(O)$_2NH_2$. In certain embodiments, Z is —S(O)$_2$NH$R^{1a}$, wherein $R^{1a}$ is as defined herein. In certain embodiments, Z is —S(O)$_2$N($R^{1a}$)$R^{1b}$, wherein $R^{1a}$ and $R^{1b}$ are each as defined herein.

In certain embodiments, X is a bond. In certain embodiments, X is O. In certain embodiments, X is S. In certain embodiments, X is N$R^{1c}$, where $R^{1c}$ is as defined herein.

In certain embodiments, n is 1. In certain embodiments, n is 2. In certain embodiments, n is 3. In certain embodiments, n is 4. In certain embodiments, n is 5.

In certain embodiments, the compounds provided herein show activity as antagonists of an AHR.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

4.4. Isolation of NK Cells

Methods of isolating natural killer cells are known in the art and can be used to isolate the natural killer cells, e.g., NK cells produced using the three-stage method, described herein. For example, NK cells can be isolated or enriched by staining cells, in one embodiment, with antibodies to CD56 and CD3, and selecting for CD56+CD3$^-$ cells. NK cells, e.g., cells produced using the three-stage method, described herein, can be isolated using a commercially available kit, for example, the NK Cell Isolation Kit (Miltenyi Biotec). NK cells, e.g., cells produced using the three-stage method, described herein, can also be isolated or enriched by removal of cells other than NK cells in a population of cells that comprise the NK cells, e.g., cells produced using the three-stage method, described herein. For example, NK cells, e.g., cells produced using the three-stage method, described herein, may be isolated or enriched by depletion of cells displaying non-NK cell markers using, e.g., antibodies to one or more of CD3, CD4, CD14, CD19, CD20, CD36, CD66b, CD123, HLA DR and/or CD235a (glycophorin A). Negative isolation can be carried out using a commercially available kit, e.g., the NK Cell Negative Isolation Kit (Dynal Biotech). Cells isolated by these methods may be additionally sorted, e.g., to separate CD16$^+$ and CD16$^-$ cells, and/or CD94$^+$ and CD94$^-$.

Cell separation can be accomplished by, e.g., flow cytometry, fluorescence-activated cell sorting (FACS), or, in one embodiment, magnetic cell sorting using microbeads conjugated with specific antibodies. The cells may be isolated, e.g., using a magnetic activated cell sorting (MACS) technique, a method for separating particles based on their ability to bind magnetic beads (e.g., about 0.5-100 μm diameter) that comprise one or more specific antibodies, e.g., anti-CD56 antibodies. Magnetic cell separation can be performed and automated using, e.g., an AUTOMACS™ Separator (Miltenyi). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

4.5. Placental Perfusate

NK cells, e.g., NK cell populations produced according to the three-stage method described herein may be produced from hematopoietic cells, e.g., hematopoietic stem or progenitors from any source, e.g., placental tissue, placental perfusate, umbilical cord blood, placental blood, peripheral blood, spleen, liver, or the like. In certain embodiments, the hematopoietic stem cells are combined hematopoietic stem cells from placental perfusate and from cord blood from the same placenta used to generate the placental perfusate. Placental perfusate comprising placental perfusate cells that can be obtained, for example, by the methods disclosed in U.S. Pat. Nos. 7,045,148 and 7,468,276 and U.S. Patent Application Publication No. 2009/0104164, the disclosures of which are hereby incorporated in their entireties.

4.5.1. Cell Collection Composition

The placental perfusate and perfusate cells, from which hematopoietic stem or progenitors may be isolated, or useful in tumor suppression or the treatment of an individual having tumor cells, cancer or a viral infection, e.g., in combination with the NK cells, e.g., NK cell populations produced according to the three-stage method provided herein, can be collected by perfusion of a mammalian, e.g., human post-partum placenta using a placental cell collection composition. Perfusate can be collected from the placenta by perfusion of the placenta with any physiologically-acceptable solution, e.g., a saline solution, culture medium, or a more complex cell collection composition. A cell collection composition suitable for perfusing a placenta, and for the collection and preservation of perfusate cells is described in detail in related U.S. Application Publication No. 2007/0190042, which is incorporated herein by reference in its entirety.

The cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The cell collection composition can comprise one or more components that tend to preserve placental cells, that is, prevent the placental cells from dying, or delay the death of the placental cells, reduce the number of placental cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-Indol-3-yl)-3-pentylamino-maleimide, pyrrolidine dithiocarbamate, or clonazepam); a TNF-α inhibitor; and/or an oxygen-carrying perfluorocarbon (e.g., perfluorooctyl bromide, perfluorodecyl bromide, etc.).

The cell collection composition can comprise one or more tissue-degrading enzymes, e.g., a metalloprotease, a serine protease, a neutral protease, a hyaluronidase, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefaclor, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/l to about 100,000 units/l); or an amiloride containing compound (e.g., amiloride, ethyl isopropyl amiloride, hexamethylene amiloride, dimethyl amiloride or isobutyl amiloride present at about 1.0 µM to about 5 µM).

4.5.2. Collection and Handling of Placenta

Generally, a human placenta is recovered shortly after its expulsion after birth. In one embodiment, the placenta is recovered from a patient after informed consent and after a complete medical history of the patient is taken and is associated with the placenta. In one embodiment, the medical history continues after delivery.

Prior to recovery of perfusate, the umbilical cord blood and placental blood are removed. In certain embodiments, after delivery, the cord blood in the placenta is recovered. The placenta can be subjected to a conventional cord blood recovery process. Typically a needle or cannula is used, with the aid of gravity, to exsanguinate the placenta (see, e.g., Anderson, U.S. Pat. No. 5,372,581; Hessel et al., U.S. Pat. No. 5,415,665). The needle or cannula is usually placed in the umbilical vein and the placenta can be gently massaged to aid in draining cord blood from the placenta. Such cord blood recovery may be performed commercially, e.g., LifeBank Inc., Cedar Knolls, N.J., ViaCord, Cord Blood Registry and CryoCell. In one embodiment, the placenta is gravity drained without further manipulation so as to minimize tissue disruption during cord blood recovery.

Typically, a placenta is transported from the delivery or birthing room to another location, e.g., a laboratory, for recovery of cord blood and collection of perfusate. The placenta can be transported in a sterile, thermally insulated transport device (maintaining the temperature of the placenta between 20-28° C.), for example, by placing the placenta, with clamped proximal umbilical cord, in a sterile zip-lock plastic bag, which is then placed in an insulated container. In another embodiment, the placenta is transported in a cord blood collection kit substantially as described in U.S. Pat. No. 7,147,626. In one embodiment, the placenta is delivered to the laboratory four to twenty-four hours following delivery. In certain embodiments, the proximal umbilical cord is clamped, for example within 4-5 cm (centimeter) of the insertion into the placental disc prior to cord blood recovery. In other embodiments, the proximal umbilical cord is clamped after cord blood recovery but prior to further processing of the placenta.

The placenta, prior to collection of the perfusate, can be stored under sterile conditions and at either room temperature or at a temperature of 5 to 25° C. (centigrade). The placenta may be stored for a period of longer than forty eight hours, or for a period of four to twenty-four hours prior to perfusing the placenta to remove any residual cord blood. The placenta can be stored in an anticoagulant solution at a temperature of 5° C. to 25° C. (centigrade). Suitable anticoagulant solutions are well known in the art. For example, a solution of heparin or warfarin sodium can be used. In one embodiment, the anticoagulant solution comprises a solution of heparin (e.g., 1% w/w in 1:1000 solution). In some embodiments, the exsanguinated placenta is stored for no more than 36 hours before placental perfusate is collected.

4.5.3. Placental Perfusion

Methods of perfusing mammalian placentae and obtaining placental perfusate are disclosed, e.g., in Hariri, U.S. Pat. Nos. 7,045,148 and 7,255,879, and in U.S. Application Publication Nos. 2009/0104164, 2007/0190042 and 20070275362, issued as U.S. Pat. No. 8,057,788, the disclosures of which are hereby incorporated by reference herein in their entireties.

Perfusate can be obtained by passage of perfusion solution, e.g., saline solution, culture medium or cell collection compositions described above, through the placental vasculature. In one embodiment, a mammalian placenta is perfused by passage of perfusion solution through either or both of the umbilical artery and umbilical vein. The flow of perfusion solution through the placenta may be accomplished using, e.g., gravity flow into the placenta. For example, the perfusion solution is forced through the placenta using a pump, e.g., a peristaltic pump. The umbilical vein can be, e.g., cannulated with a cannula, e.g., a TEFLON® or plastic cannula, that is connected to a sterile connection apparatus, such as sterile tubing. The sterile connection apparatus is connected to a perfusion manifold.

In preparation for perfusion, the placenta can be oriented in such a manner that the umbilical artery and umbilical vein are located at the highest point of the placenta. The placenta can be perfused by passage of a perfusion solution through the placental vasculature, or through the placental vasculature and surrounding tissue. In one embodiment, the umbilical artery and the umbilical vein are connected simultaneously to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. In another embodiment, the perfusion solution is passed through the umbilical veins and collected from the umbilical artery, or is passed through the umbilical artery and collected from the umbilical veins, that is, is passed through only the placental vasculature (fetal tissue).

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, e.g., an amniotic membrane biomaterial, e.g., the biomaterial described in U.S. Application Publication No. 2004/0048796. After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and, more specifically, can be clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 mL of perfusion fluid is adequate to initially flush blood from the placenta, but more or less perfusion fluid may be used depending on the observed results.

In certain embodiments, cord blood is removed from the placenta prior to perfusion (e.g., by gravity drainage), but the placenta is not flushed (e.g., perfused) with solution to remove residual blood. In certain embodiments, cord blood is removed from the placenta prior to perfusion (e.g., by gravity drainage), and the placenta is flushed (e.g., perfused) with solution to remove residual blood.

The volume of perfusion liquid used to perfuse the placenta may vary depending upon the number of placental cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days. Where the placenta is to be perfused a plurality of times, it may be maintained or cultured under aseptic conditions in a container or other suitable vessel, and perfused with a cell collection composition, or a standard perfusion solution (e.g., a normal saline solution such as phosphate buffered saline ("PBS") with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 µg/ml), penicillin (e.g., at 40 U/ml), amphotericin B (e.g., at 0.5 µg/ml).

In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In one embodiment, perfusion of the placenta and collection of perfusion solution, e.g., placental cell collection composition, is repeated until the number of recovered nucleated cells falls below 100 cells/ml. The perfusates at different time points can be further processed individually to recover time-dependent populations of cells, e.g., total nucleated cells. Perfusates from different time points can also be pooled.

4.5.4. Placental Perfusate and Placental Perfusate Cells

Typically, placental perfusate from a single placental perfusion comprises about 100 million to about 500 million nucleated cells, including hematopoietic cells from which NK cells, e.g., NK cells produced according to the three-stage method described herein, may be produced by the method disclosed herein. In certain embodiments, the placental perfusate or perfusate cells comprise $CD34^+$ cells, e.g., hematopoietic stem or progenitor cells. Such cells can, in a more specific embodiment, comprise $CD34^+CD45^-$ stem or progenitor cells, $CD34^+CD45^+$ stem or progenitor cells, or the like. In certain embodiments, the perfusate or perfusate cells are cryopreserved prior to isolation of hematopoietic cells therefrom. In certain other embodiments, the placental perfusate comprises, or the perfusate cells comprise, only fetal cells, or a combination of fetal cells and maternal cells.

4.6. NK Cells 4.6.1. NK Cells Produced by Three-Stage Method

In another embodiment, provided herein is an isolated NK cell population, wherein said NK cells are produced according to the three-stage method described above.

In one embodiment, provided herein is an isolated NK cell population produced by a three-stage method described herein, wherein said NK cell population comprises a greater percentage of CD3−CD56+ cells than an NK progenitor cell population produced by a three-stage method described herein, e.g., an NK progenitor cell population produced by the same three-stage method with the exception that the third culture step used to produce the NK progenitor cell population was of shorter duration than the third culture step used to produce the NK cell population. In a specific embodiment, said NK cell population comprises about 70% or more, in some embodiments, 75%, 80%, 85%, 90%, 95%, 98%, or 99% CD3−CD56+ cells. In another specific embodiment, said NK cell population comprises no less than 80%, 85%, 90%, 95%, 98%, or 99% CD3−CD56+ cells. In another specific embodiment, said NK cell population comprises between 70%-75%, 75%-80%, 80%-85%, 85%-90%, 90%-95%, or 95%-99% CD3−CD56+ cells.

In certain embodiments, said $CD3^-CD56^+$ cells in said NK cell population comprises $CD3^-CD56^+$ cells that are additionally $NKp46^+$. In certain embodiments, said $CD3^-CD56^+$ cells in said NK cell population comprises $CD3^-CD56^+$ cells that are additionally CD16−. In certain embodiments, said $CD3^-CD56^+$ cells in said NK cell population comprises $CD3^-CD56^+$ cells that are additionally CD16+. In certain embodiments, said $CD3^-CD56^+$ cells in said NK cell population comprises $CD3^-CD56^+$ cells that are additionally CD94−. In certain embodiments, said $CD3^-CD56^+$ cells in said NK cell population comprises $CD3^-CD56^+$ cells that are additionally CD94+.

In one embodiment, an NK cell population produced by a three-stage method described herein comprises cells which are CD117+. In one embodiment, an NK cell population produced by a three-stage method described herein comprises cells which are NKG2D+. In one embodiment, an NK cell population produced by a three-stage method described herein comprises cells which are NKp44+. In one embodiment, an NK cell population produced by a three-stage method described herein comprises cells which are CD244+.

4.7. Preservation of Cells

Cells, e.g., NK cells produced using the methods described herein, e.g., NK cell populations produced using the three-stage method described herein, or placental perfusate cells comprising hematopoietic stem cells or progenitor cells, can be preserved, that is, placed under conditions that allow for long-term storage, or under conditions that inhibit cell death by, e.g., apoptosis or necrosis.

Placental perfusate can be produced by passage of a cell collection composition through at least a part of the placenta, e.g., through the placental vasculature. The cell collection composition comprises one or more compounds that act to preserve cells contained within the perfusate. Such a placental cell collection composition can comprise an apoptosis inhibitor, necrosis inhibitor and/or an oxygen-carrying perfluorocarbon, as described in related U.S. Application Publication No. 20070190042, the disclosure of which is hereby incorporated by reference in its entirety.

In one embodiment, perfusate or a population of placental cells are collected from a mammalian, e.g., human, postpartum placenta by bringing the perfusate or population of cells into proximity with a cell collection composition comprising an inhibitor of apoptosis and an oxygen-carrying perfluorocarbon, wherein said inhibitor of apoptosis is present in an amount and for a time sufficient to reduce or prevent apoptosis in the population of placental cells, e.g., adherent placental cells, for example, placental stem cells or placental multipotent cells, as compared to a population of cells not contacted or brought into proximity with the inhibitor of apoptosis. For example, the placenta can be perfused with the cell collection composition, and placental cells, e.g., total nucleated placental cells, are isolated therefrom. In a specific embodiment, the inhibitor of apoptosis is a caspase inhibitor. In another specific embodiment, said inhibitor of apoptosis is a JNK inhibitor. In a more specific embodiment, said JNK inhibitor does not modulate differentiation or proliferation of adherent placental cells, e.g., adherent placental stem cells or adherent placental multipotent cells. In another embodiment, the cell collection composition comprises said inhibitor of apoptosis and said oxygen-carrying perfluorocarbon in separate phases. In another embodiment, the cell collection composition comprises said inhibitor of apoptosis and said oxygen-carrying perfluorocarbon in an emulsion. In another embodiment, the cell collection composition additionally comprises an emulsifier, e.g., lecithin. In another embodiment, said apoptosis inhibitor and said perfluorocarbon are between about 0° C. and about 25° C. at the time of bringing the placental cells into proximity with the cell collection composition. In another more specific embodiment, said apoptosis inhibitor and said perfluorocarbon are between about 2° C. and 10° C., or between about 2° C. and about 5° C., at the time of bringing the placental cells into proximity with the cell collection composition. In another more specific embodiment, said bringing into proximity is performed during transport of said population of cells. In another more specific embodiment, said bringing into proximity is performed during freezing and thawing of said population of cells.

In another embodiment, placental perfusate and/or placental cells can be collected and preserved by bringing the perfusate and/or cells into proximity with an inhibitor of apoptosis and an organ-preserving compound, wherein said inhibitor of apoptosis is present in an amount and for a time sufficient to reduce or prevent apoptosis of the cells, as compared to perfusate or placental cells not contacted or brought into proximity with the inhibitor of apoptosis. In a specific embodiment, the organ-preserving compound is UW solution (described in U.S. Pat. No. 4,798,824; also known as VIASPAN™; see also Southard et al., *Transplantation* 49(2):251-257 (1990) or a solution described in Stern et al., U.S. Pat. No. 5,552,267, the disclosures of which are hereby incorporated by reference in their entireties. In another embodiment, said organ-preserving composition is hydroxyethyl starch, lactobionic acid, raffinose, or a combination thereof. In another embodiment, the placental cell collection composition additionally comprises an oxygen-carrying perfluorocarbon, either in two phases or as an emulsion.

In another embodiment of the method, placental cells are brought into proximity with a cell collection composition comprising an apoptosis inhibitor and oxygen-carrying perfluorocarbon, organ-preserving compound, or combination thereof, during perfusion. In another embodiment, placental cells are brought into proximity with said cell collection compound after collection by perfusion.

Typically, during placental cell collection, enrichment and isolation, it is preferable to minimize or eliminate cell stress due to hypoxia and mechanical stress. In another embodiment of the method, therefore, placental perfusate or a population of placental cells is exposed to a hypoxic condition during collection, enrichment or isolation for less than six hours during said preservation, wherein a hypoxic condition is a concentration of oxygen that is less than normal blood oxygen concentration. In a more specific embodiment, said perfusate or population of placental cells is exposed to said hypoxic condition for less than two hours during said preservation. In another more specific embodiment, said population of placental cells is exposed to said hypoxic condition for less than one hour, or less than thirty minutes, or is not exposed to a hypoxic condition, during collection, enrichment or isolation. In another specific embodiment, said population of placental cells is not exposed to shear stress during collection, enrichment or isolation.

Cells, e.g., placental perfusate cells, hematopoietic cells, e.g., CD34$^+$ hematopoietic stem cells; NK cells produced using the methods described herein; isolated adherent placental cells provided herein can be cryopreserved, e.g., in cryopreservation medium in small containers, e.g., ampoules or septum vials. In certain embodiments, cells provided herein are cryopreserved at a concentration of about $1\times10^4$-$5\times10^8$ cells per mL. In specific embodiments, cells provided herein are cryopreserved at a concentration of about $1\times10^6$-$1.5\times10^7$ cells per mL. In more specific embodiments, cells provided herein are cryopreserved at a concentration of about $1\times10^4$, $5\times10^4$, $1\times10^5$, $5\times10^5$, $1\times10^6$, $5\times10^6$, $1\times10^7$, $1.5\times10^7$ cells per mL.

Suitable cryopreservation medium includes, but is not limited to, normal saline, culture medium including, e.g., growth medium, or cell freezing medium, for example commercially available cell freezing medium, e.g., C2695, C2639 or C6039 (Sigma); CryoStor® CS2, CryoStor® CS5 or CryoStor® CS10 (BioLife Solutions). In one embodiment, cryopreservation medium comprises DMSO (dimethylsulfoxide), at a concentration of, e.g., about 1, 2, 3, 4, 5, 6, 7, 8, 9 or 10% (v/v). Cryopreservation medium may comprise additional agents, for example, methylcellulose, dextran, albumin (e.g., human serum albumin), trehalose, and/or glycerol. In certain embodiments, the cryopreservation medium comprises about 1%-10% DMSO, about 25%-75% dextran and/or about 20-60% human serum albumin (HSA). In certain embodiments, the cryopreservation medium comprises about 1%-10% DMSO, about 25%-75% trehalose and/or about 20-60% human HSA. In a specific embodiment, the cryopreservation medium comprises 5% DMSO, 55% dextran and 40% HSA. In a more specific embodiment, the cryopreservation medium comprises 5% DMSO, 55% dextran (10% w/v in normal saline) and 40% HSA. In another specific embodiment, the cryopreservation medium comprises 5% DMSO, 55% trehalose and 40% HSA. In a more specific embodiment, the cryopreservation medium comprises 5% DMSO, 55% trehalose (10% w/v in normal saline) and 40% HSA. In another specific embodiment, the cryopreservation medium comprises CryoStor® CS5. In another specific embodiment, the cryopreservation medium comprises CryoStor® CS10.

Cells provided herein can be cryopreserved by any of a variety of methods, and at any stage of cell culturing, expansion or differentiation. For example, cells provided herein can be cryopreserved right after isolation from the origin tissues or organs, e.g., placental perfusate or umbilical cord blood, or during, or after either the first, second, or third step of the methods outlined above. In certain embodiments, the hematopoietic cells, e.g., hematopoietic stem or progenitor cells are cryopreserved within about 1, 5, 10, 15, 20, 30, 45 minutes or within about 1, 2, 4, 6, 10, 12, 18, 20 or 24 hours after isolation from the origin tissues or organs. In certain embodiments, said cells are cryopreserved within 1, 2 or 3 days after isolation from the origin tissues or organs. In certain embodiments, said cells are cryopreserved after being cultured in a first medium as described above, for about 1, 2, 3, 4, 5, 6, 7, 8, 9, 10, 11, 12, 13, 14, 15, 16, 17, 18, 19, 20, 21, 22, 23, 24, 25, 26, 27 or 28 days. In some embodiments, said cells are cryopreserved after being cultured in a first medium as described above, for about 1, 2, 3, 4, 5, 6, 7, 8, 9, 10, 11, 12, 13, 14, 15, 16, 17, 18, 19, 20, 21, 22, 23, 24, 25, 26, 27 or 28 days, and in a second medium for about 1, 2, 3, 4, 5, 6, 7, 8, 9, 10, 11, 12, 13, 14, 15, 16, 17, 18, 19, 20, 21, 22, 23, 24, 25, 26, 27 or 28 days as described above. In some embodiments, when NK cells are made using a three-stage method described herein, said cells are cryopreserved after being cultured in a first medium about 1, 2, 3, 4, 5, 6, 7, 8, 9, 10, 11, 12, 13, 14, 15, 16, 17, 18, 19, 20, 21, 22, 23, 24, or 25 days; and/or after being cultured in a second medium about 1, 2, 3, 4, 5, 6, 7, 8, 9, 10, 11, 12, 13, 14, 15, 16, 17, 18, 19, 20, 21, 22, 23, 24, or 25 days; and/or after being cultured in a third medium about 1, 2, 3, 4, 5, 6, 7, 8, 9, 10, 11, 12, 13, 14, 15, 16, 17, 18, 19, 20, 21, 22, 23, 24, or 25 days. In a specific embodiment, NK cells are made using a three-stage method described herein, and said cells are cryopreserved after being cultured in a first medium for 10 days; after being cultured in a second medium for 4 days; and after being cultured in a third medium for 21 days.

In one aspect, provided herein is a method of cryopreserving a population of NK cells, e.g., NK cells produced by a three-stage method described herein. In one embodiment, said method comprises: culturing hematopoietic stem cells or progenitor cells, e.g., CD34$^+$ stem cells or progenitor cells, in a first medium comprising a stem cell mobilizing agent and thrombopoietin (Tpo) to produce a first population of cells, subsequently culturing said first population of cells in a second medium comprising a stem cell mobilizing agent and interleukin-15 (IL-15), and lacking Tpo, to produce a second population of cells, and subsequently culturing said second population of cells in a third medium comprising IL-2 and IL-15, and lacking a stem cell mobilizing agent and LMWH, to produce a third population of cells, wherein the third population of cells comprises natural killer cells that are CD56+, CD3−, CD16− or CD16+, and CD94+ or CD94−, and wherein at least 70%, or at least 80%, of the natural killer cells are viable, and next, cryopreserving the NK cells in a cryopreservation medium. In a specific embodiment, said cryopreservation step further comprises (1) preparing a cell suspension solution; (2) adding cryopreservation medium to the cell suspension solution from step (1) to obtain cryopreserved cell suspension; (3) cooling the cryopreserved cell suspension from step (3) to obtain a cryopreserved sample; and (4) storing the cryopreserved sample below −80° C. In certain embodiments, the method includes no intermediary steps.

Cells provided herein can be cooled in a controlled-rate freezer, e.g., at about 0.1, 0.3, 0.5, 1, or 2 OC/min during cryopreservation. In one embodiment, the cryopreservation temperature is about −80° C. to about −180° C., or about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells can be thawed at a temperature of about 25° C. to about 40° C., more specifically can be thawed to a temperature of about 37° C. In certain embodiments, the cryopreserved cells are thawed after being cryopreserved for about 1, 2, 4, 6, 10, 12, 18, 20 or 24 hours, or for about 1, 2, 3, 4, 5, 6, 7, 8, 9, 10, 11, 12, 13, 14, 15, 16, 17, 18, 19, 20, 21, 22, 23, 24, 25, 26, 27 or 28 days. In certain embodiments, the cryopreserved cells are thawed after being cryopreserved for about 1, 2, 3, 4, 5, 6, 7, 8, 9, 10, 11, 12, 13, 14, 15, 16, 17, 18, 19, 20, 21, 22, 23, 24, 25, 26, 27 or 28 months. In certain embodiments, the cryopreserved cells are thawed after being cryopreserved for about 1, 2, 3, 4, 5, 6, 7, 8, 9 or 10 years.

Suitable thawing medium includes, but is not limited to, normal saline, plasmalyte culture medium including, for example, growth medium, e.g., RPMI medium. In certain embodiments, the thawing medium comprises one or more of medium supplements (e.g., nutrients, cytokines and/or factors). Medium supplements suitable for thawing cells provided herein include, for example without limitation, serum such as human serum AB, fetal bovine serum (FBS) or fetal calf serum (FCS), vitamins, human serum albumin (HSA), bovine serum albumin (BSA), amino acids (e.g., L-glutamine), fatty acids (e.g., oleic acid, linoleic acid or palmitic acid), insulin (e.g., recombinant human insulin), transferrin (iron saturated human transferrin), β-mercaptoethanol, stem cell factor (SCF), Fms-like-tyrosine kinase 3 ligand (Flt3-L), cytokines such as interleukin-2 (IL-2), interleukin-7 (IL-7), interleukin-15 (IL-15), thrombopoietin (Tpo) or heparin. In a specific embodiment, the thawing medium useful in the methods provided herein comprises RPMI. In another specific embodiment, said thawing medium comprises plasmalyte. In another specific embodiment, said thawing medium comprises about 0.5-20% FBS. In another specific embodiment, said thawing medium comprises about 1, 2, 5, 10, 15 or 20% FBS. In another specific embodiment, said thawing medium comprises about 0.5%-20% HSA. In another specific embodiment, said thawing medium comprises about 1, 2.5, 5, 10, 15, or 20% HSA. In a more specific embodiment, said thawing medium comprises RPMI and about 10% FBS. In another more specific embodiment, said thawing medium comprises plasmalyte and about 5% HSA.

The cryopreservation methods provided herein can be optimized to allow for long-term storage, or under conditions that inhibit cell death by, e.g., apoptosis or necrosis. In one embodiments, the post-thaw cells comprise greater than 60%, 65%, 70%, 75%, 80%, 85%, 90%, 95% or 98% of viable cells, as determined by, e.g., automatic cell counter or trypan blue method. In another embodiment, the post-thaw cells comprise about 0.5, 1, 5, 10, 15, 20 or 25% of dead cells. In another embodiment, the post-thaw cells comprise about 0.5, 1, 5, 10, 15, 20 or 25% of early apoptotic cells. In another embodiment, about 0.5, 1, 5, 10, 15 or 20% of post-thaw cells undergo apoptosis after 1, 2, 3, 4, 5, 6, 7, 8, 9, 10, 11, 12, 13, 14, 15, 16, 17, 18, 19, 20, 21, 22, 23, 24, 25, 26, 27 or 28 days after being thawed, e.g., as determined by an apoptosis assay (e.g., TO-PRO3 or AnnV/PI Apoptosis assay kit). In certain embodiments, the post-thaw cells are re-cryopreserved after being cultured, expanded or differentiated using methods provided herein.

4.8. Compositions Comprising NK Cells 4.8.1. NK Cells Produced Using the Three-Stage Method In some embodiments, provided herein is a composition, e.g., a pharmaceutical composition, comprising an isolated NK cell population produced using the three-stage method described herein. In a specific embodiment, said isolated NK cell population is produced from hematopoietic cells, e.g., hematopoietic stem or progenitor cells isolated from placental perfusate, umbilical cord blood, and/or peripheral blood. In another specific embodiment, said isolated NK cell population comprises at least 50% of cells in the composition. In another specific embodiment, said isolated NK cell population, e.g., CD3$^-$CD56$^+$ cells, comprises at least 80%, 85%, 90%, 95%, 98% or 99% of cells in the composition. In certain embodiments, no more than 5%, 10%, 15%, 20%, 25%, 30%, 35%, or 40% of the cells in said isolated NK cell population are CD3$^-$CD56$^+$ cells. In certain embodiments, said CD3$^-$CD56$^+$ cells are CD16$^-$.

In another specific embodiment, said isolated NK cells in said composition are from a single individual. In a more specific embodiment, said isolated NK cells comprise NK cells from at least two different individuals. In another specific embodiment, said isolated NK cells in said composition are from a different individual than the individual for whom treatment with the NK cells is intended. In another specific embodiment, said NK cells have been contacted or brought into proximity with an immunomodulatory compound or thalidomide in an amount and for a time sufficient for said NK cells to express detectably more granzyme B or perforin than an equivalent number of natural killer cells, i.e. NK cells not contacted or brought into proximity with said immunomodulatory compound or thalidomide. In another specific embodiment, said composition additionally comprises an immunomodulatory compound or thalidomide. In certain embodiments, the immunomodulatory compound is a compound described below. See, e.g., U.S. Pat. No. 7,498,171, the disclosure of which is hereby incorporated by reference in its entirety. In certain embodiments, the immunomodulatory compound is an amino-substituted isoindoline. In one embodiment, the immunomodulatory compound is 3-(4-amino-1-oxo-1,3-dihydroisoindol-2-yl)-piperidine-2,6-dione; 3-(4'aminoisoindoline-1'-one)-1-piperidine-2,6-dione; 4-(amino)-2-(2,6-dioxo(3-piperidyl))-isoindoline-1, 3-dione; or 4-Amino-2-(2,6-dioxopiperidin-3-yl)isoindole-1,3-dione. In another embodiment, the immunomodulatory compound is pomalidomide, or lenalidomide. In another embodiment, said immunomodulatory compound is a compound having the structure

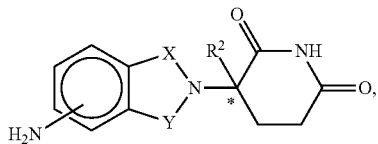

wherein one of X and Y is C=O, the other of X and Y is C=O or $CH_2$, and $R^2$ is hydrogen or lower alkyl, or a pharmaceutically acceptable salt, hydrate, solvate, clathrate, enantiomer, diastereomer, racemate, or mixture of stereoisomers thereof. In another embodiment, said immunomodulatory compound is a compound having the structure

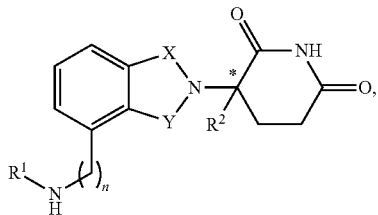

wherein one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $C(O)R^3$, $C(S)R^3$, $C(O)OR^4$, $(C_1-C_8)$alkyl-$N(R^6)_2$, $(C_1-C_8)$alkyl-$OR^5$, $(C_1-C_8)$alkyl-$C(O)OR^5$, $C(O)NHR^3$, $C(S)NHR^3$, $C(O)NR^3R^{3'}$, $C(S)NR^3R^{3'}$ or $(C_1-C_8)$alkyl-$O(CO)R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-$N(R^6)_2$, $(C_1-C_8)$alkyl-$OR^5$, $(C_1-C_8)$alkyl-$C(O)OR^5$, $(C_1-C_8)$alkyl-$O(CO)R^5$, or $C(O)OR^5$;

$R^4$ is $(C_1-C_8)$alkyl, $(C_2-C_8)$alkenyl, $(C_2-C_8)$alkynyl, $(C_1-C_4)$alkyl-$OR^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to form a heterocycloalkyl group;

n is 0 or 1; and

*represents a chiral-carbon center;

or a pharmaceutically acceptable salt, hydrate, solvate, clathrate, enantiomer, diastereomer, racemate, or mixture of stereoisomers thereof. In another embodiment, said immunomodulatory compound is a compound having the structure

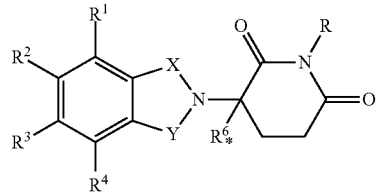

wherein:

one of X and Y is C=O and the other is $CH_2$ or C=O;

R is H or $CH_2OCOR'$;

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —$NHR^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—$CHR^{10}$—$N(R^8R^9)$;

$R^7$ is m-phenylene or p-phenylene or —$(C_nH_{2n})$— in which n has a value of 0 to 4;

each of $R^8$ and $R^9$ taken independently of the other is hydrogen or alkyl of 1 to 8 carbon atoms, or $R^8$ and $R^9$ taken together are tetramethylene, pentamethylene, hexamethylene, or —$CH_2CH_2X_1CH_2CH_2$— in which $X_1$ is —O—, —S—, or —NH—;

$R^{10}$ is hydrogen, alkyl of to 8 carbon atoms, or phenyl; and

*represents a chiral-carbon center;

or a pharmaceutically acceptable salt, hydrate, solvate, clathrate, enantiomer, diastereomer, racemate, or mixture of stereoisomers thereof.

In another specific embodiment, the composition additionally comprises one or more anticancer compounds, e.g., one or more of the anticancer compounds described below.

In a more specific embodiment, the composition comprises NK cells from another source, or made by another method. In a specific embodiment, said other source is placental blood and/or umbilical cord blood. In another specific embodiment, said other source is peripheral blood. In more specific embodiments, the NK cell population in said composition is combined with NK cells from another source, or made by another method in a ratio of about 100:1, 95:5, 90:10, 85:15, 80:20, 75:25, 70:30, 65:35, 60:40, 55:45: 50:50, 45:55, 40:60, 35:65, 30:70, 25:75, 20:80, 15:85, 10:90, 5:95, 100:1, 95:1, 90:1, 85:1, 80:1, 75:1, 70:1, 65:1, 60:1, 55:1, 50:1, 45:1, 40:1, 35:1, 30:1, 25:1, 20:1, 15:1, 10:1, 5:1, 1:1, 1:5, 1:10, 1:15, 1:20, 1:25, 1:30, 1:35, 1:40, 1:45, 1:50, 1:55, 1:60, 1:65, 1:70, 1:75, 1:80, 1:85, 1:90, 1:95, 1:100, or the like.

In another specific embodiment, the composition comprises an NK cell population produced using the three-stage method described herein and either isolated placental perfusate or isolated placental perfusate cells. In a more specific embodiment, said placental perfusate is from the same individual as said NK cell population. In another more specific embodiment, said placental perfusate comprises placental perfusate from a different individual than said NK cell population. In another specific embodiment, all, or substantially all (e.g., greater than 90%, 95%, 98% or 99%) of cells in said placental perfusate are fetal cells. In another specific embodiment, the placental perfusate or placental perfusate cells, comprise fetal and maternal cells. In a more specific embodiment, the fetal cells in said placental perfusate comprise less than about 90%, 80%, 70%, 60% or 50% of the cells in said perfusate. In another specific embodiment, said perfusate is obtained by passage of a 0.9% NaCl solution through the placental vasculature. In another specific embodiment, said perfusate comprises a culture medium. In another specific embodiment, said perfusate has been treated to remove erythrocytes. In another specific embodiment, said composition comprises an immunomodulatory compound, e.g., an immunomodulatory compound described below, e.g., an amino-substituted isoindoline compound. In another specific embodiment, the composition additionally comprises one or more anticancer compounds, e.g., one or more of the anticancer compounds described below.

In another specific embodiment, the composition comprises an NK cell population and placental perfusate cells. In a more specific embodiment, said placental perfusate cells are from the same individual as said NK cell population. In another more specific embodiment, said placental perfusate cells are from a different individual than said NK cell population. In another specific embodiment, the composition comprises isolated placental perfusate and isolated placental perfusate cells, wherein said isolated perfusate and said isolated placental perfusate cells are from different individuals. In another more specific embodiment of any of the above embodiments comprising placental perfusate, said placental perfusate comprises placental perfusate from at least two individuals. In another more specific embodiment of any of the above embodiments comprising placental perfusate cells, said isolated placental perfusate cells are from at least two individuals. In another specific embodiment, said composition comprises an immunomodulatory compound. In another specific embodiment, the composition additionally comprises one or more anticancer compounds, e.g., one or more of the anticancer compounds described below.

4.9. Uses of NK Cells Produced Using the Three-Stage Method

The NK cells produced using the methods described herein, e.g., NK cell produced according to the three-stage method described herein, provided herein can be used in methods of treating individuals having acute myeloid leukemia, e.g., individuals having acute myeloid leukemia cells. In some such embodiments, an effective dosage of NK cells produced using the methods described herein ranges from $1 \times 10^4$ to $5 \times 10^4$, $5 \times 10^4$ to $1 \times 10^5$, $1 \times 10^5$ to $5 \times 10^5$, $5 \times 10^5$ to $1 \times 10^6$, $1 \times 10^6$ to $5 \times 10^6$, $5 \times 10^6$ to $1 \times 10^7$, or more cells/kilogram body weight. In more specific embodiments, an effective dosage of NK cells produced using the methods described herein ranges from $1 \times 10^6$ to $30 \times 10^6$. The NK cells produced using the methods described herein, can also be used in methods of suppressing proliferation of tumor cells.

The NK cells produced using the methods described herein, e.g., NK cell produced according to the three-stage method described herein, provided herein can be used in methods of treating individuals having multiple myeloma, e.g., individuals having multiple myeloma cells. In some such embodiments, an effective dosage of NK cells produced using the methods described herein ranges from $1 \times 10^4$ to $5 \times 10^4$, $5 \times 10^4$ to $1 \times 10^5$, $1 \times 10^5$ to $5 \times 10^5$, $5 \times 10^5$ to $1 \times 10^6$, $1 \times 10^6$ to $5 \times 10^6$, $5 \times 10^6$ to $1 \times 10^7$, or more cells/kilogram body weight. In more specific embodiments, an effective dosage of NK cells produced using the methods described herein ranges from $1 \times 10^6$ to $30 \times 10^6$. The NK cells produced using the methods described herein, can also be used in methods of suppressing proliferation of tumor cells.

4.9.1. Treatment of Individuals Having Cancer

In one embodiment, provided herein is a method of treating an individual having acute myeloid leukemia, comprising administering to said individual a therapeutically effective amount of NK cells produced using the methods described herein, e.g., NK cell populations produced using the three-stage method described herein. In certain embodiments, the individual has a deficiency of natural killer cells, e.g., a deficiency of NK cells active against acute myeloid leukemia. In certain embodiments, provided herein is a method of treating an individual having acute myeloid leukemia, comprising administering to said individual a therapeutically effective amount of NK cells produced using the methods described herein, e.g., NK cell populations produced using the three-stage method described herein, further comprising administering to said individual a therapeutically effective amount of IL-2. In specific embodiments, the IL-2 is rhIL-2.

In one embodiment, provided herein is a method of treating an individual having multiple myeloma, comprising administering to said individual a therapeutically effective amount of NK cells produced using the methods described herein, e.g., NK cell populations produced using the three-stage method described herein. In certain embodiments, the individual has a deficiency of natural killer cells, e.g., a deficiency of NK cells active against multiple myeloma. In certain embodiments, provided herein is a method of treating an individual having multiple myeloma, comprising administering to said individual a therapeutically effective amount of NK cells produced using the methods described herein, e.g., NK cell populations produced using the three-stage method described herein, further comprising administering to said individual a therapeutically effective amount of IL-2. In specific embodiments, the IL-2 is rhIL-2. In certain embodiments, said individual has received chemotherapy prior to administering said natural killer cells. In specific embodiments, the chemotherapy is an alkylating agent. In more specific embodiments, the alkylating agent is melphalan. In certain embodiments, melphalan is administered according to the label.

In one embodiment, administration of an isolated population of NK cells or a pharmaceutical composition thereof is systemic. In specific embodiments, administration of an isolated population of NK cells or a pharmaceutical composition thereof to a subject is by infusion. In more specific embodiments, administration of an isolated population of NK cells or a pharmaceutical composition thereof to a subject is by intravenous (IV) infusion. In certain embodiments, administration of IL-2 to a subject is by subcutaneous injection. In specific embodiments, the IL-2 is rhIL-2.

In certain embodiments, the individual having acute myeloid leukemia is an individual that has received a bone marrow transplant before said administering. In certain embodiments, the bone marrow transplant was in treatment of said acute myeloid leukemia. In certain other embodiments, the bone marrow transplant was in treatment of a condition other than said cancer. In certain embodiments, the individual received an immunosuppressant in addition to said bone marrow transplant. In certain embodiments, the individual who has had a bone marrow transplant exhibits one or more symptoms of graft-versus-host disease (GVHD) at the time of said administration. In certain other embodiments, the individual who has had a bone marrow transplant is administered said cells before a symptom of GVHD has manifested.

In certain embodiments, the individual having multiple myeloma is an individual that has received a bone marrow transplant before said administering. In certain embodiments, the bone marrow transplant was in treatment of said multiple myeloma. In certain other embodiments, the bone marrow transplant was in treatment of a condition other than said cancer. In certain embodiments, the individual received an immunosuppressant in addition to said bone marrow transplant. In certain embodiments, the individual who has had a bone marrow transplant exhibits one or more symptoms of graft-versus-host disease (GVHD) at the time of said administration. In certain other embodiments, the individual who has had a bone marrow transplant is administered said cells before a symptom of GVHD has manifested. In certain embodiments, the individual having multiple myeloma is an individual that has received an autologous stem cell transplant before said administering. In certain embodiments, the autologous stem cell transplant was in treatment of said multiple myeloma. In certain embodiments, the stem cells in the autologous stem cell transplant are peripheral blood mononuclear cells. An autologous stem cell transplant is performed using stem cells harvested from the patient, stored, and frozen for later use. In certain embodiments, the autologous stem cells are harvested from the peripheral blood of a patient, frozen, stored, and re-introduced into the patient after treatment with chemotherapy and/or radiation.

In certain specific embodiments, the individual having acute myeloid leukemia or multiple myeloma has received at least one dose of a TNFα inhibitor, e.g., ETANERCEPT® (Enbrel), prior to said administering. In specific embodiments, said individual received said dose of a TNFα inhibitor within 1, 2, 3, 4, 5, 6, 7, 8, 9, 10, 11 or 12 months of diagnosis of said acute myeloid leukemia. In specific embodiments, NK cells produced using the three-stage methods provided herein are administered to said individual who received said dose of a TNFα inhibitor within 1, 2, 3, 4, 5, 6, 7, 8, 9, 10, 11 or 12 months of receiving said dose of a TNFα inhibitor. In a specific embodiment, the individual who has received a dose of a TNFα inhibitor and exhibits acute myeloid leukemia further exhibits deletion of the long arm of chromosome 5 in blood cells. In another embodiment, the individual having acute myeloid leukemia exhibits a Philadelphia chromosome.

In certain other embodiments, the acute myeloid leukemia or multiple myeloma in said individual is refractory to one or more anticancer drugs. In a specific embodiment, the acute myeloid leukemia or multiple myeloma is refractory to GLEEVEC® (imatinib mesylate).

In certain embodiments, the acute myeloid leukemia in said individual responds to at least one anticancer drug; in this embodiment, placental perfusate, isolated placental perfusate cells, isolated natural killer cells, e.g., placental natural killer cells, e.g., placenta-derived intermediate natural killer cells, isolated combined natural killer cells, or NK cells described herein, and/or combinations thereof, and optionally IL-2, are added as adjunct treatments or as a combination therapy with said anticancer drug. In certain other embodiments, the individual having acute myeloid leukemia has been treated with at least one anticancer drug, and has relapsed, prior to said administering. In certain embodiments, the individual to be treated has a refractory acute myeloid leukemia. In certain embodiments, the individual to be treated has secondary acute myeloid leukemia. In specific embodiments, the secondary myeloid leukemia is treatment-related. In specific embodiments, the secondary acute myeloid leukemia is caused by myelodysplastic syndrome transformation. In certain embodiments, the individual to be treated has had acute myeloid leukemia relapses greater than two months after transplant. In one embodiment, the acute myeloid leukemia treatment method with the cells described herein protects against (e.g., prevents or delays) relapse of acute myeloid leukemia. In one embodiment, the acute myeloid leukemia treatment method described herein results in remission of the acute myeloid leukemia for 1 month or more, 2, 3, 4, 5, 6, 7, 8, 9, 10, 11, or 12 months or more, 1 year or more, 2 years or more, 3 years or more, or 4 years or more.

In another embodiment, provided herein is a method of treating an individual having acute myeloid leukemia, comprising administering to the individual NK cells, wherein said NK cells are effective to treat acute myeloid leukemia in said individual. In a specific embodiment, said NK cells are cord blood NK cells, or NK cells produced from cord blood hematopoietic cells, e.g., hematopoietic stem cells. In another embodiment, said NK cells have been produced by a three-stage method described herein for producing NK cells. In certain specific embodiments of the method of treating an individual with acute myeloid leukemia, said NK cells are produced by a three-stage method, as described herein. In a particular embodiment, the acute myeloid leukemia to be treated by the foregoing methods comprises refractory acute myeloid leukemia, poor-prognosis acute myeloid leukemia, or childhood acute myeloid leukemia. Methods known in the art for administering NK cells for the treatment of refractory acute myeloid leukemia, poor-prognosis acute myeloid leukemia, or childhood acute myeloid leukemia may be adapted for this purpose; see, e.g., Miller et al., 2005, Blood 105:3051-3057; Rubnitz et al., 2010, J Clin Oncol. 28:955-959, each of which is incorporated herein by reference in its entirety. In certain embodiments, said individual has acute myeloid leukemia that has failed at least one non-natural killer cell therapeutic against acute myeloid leukemia. In specific embodiments, said individual is 65 years old or greater, and is in first remission. In specific embodiments, said individual has been conditioned with fludarabine, cytarabine, or both prior to administering said natural killer cells.

In other specific embodiments of the method of treating an individual with acute myeloid leukemia, said NK cells are produced by a method comprising: culturing hematopoietic stem cells or progenitor cells, e.g., CD34$^+$ stem cells or progenitor cells, in a first medium comprising a stem cell mobilizing agent and thrombopoietin (Tpo) to produce a first population of cells, subsequently culturing said first population of cells in a second medium comprising a stem cell mobilizing agent and interleukin-15 (IL-15), and lacking Tpo, to produce a second population of cells, and subsequently culturing said second population of cells in a third medium comprising IL-2 and IL-15, and lacking a stem cell mobilizing agent and LMWH, to produce a third population of cells, wherein the third population of cells comprises natural killer cells that are CD56+, CD3−, CD16− or CD16+, and CD94+ or CD94−, and wherein at least 70%, or at least 80%, of the natural killer cells are viable.

In certain embodiments, the multiple myeloma in said individual responds to at least one anticancer drug; in this embodiment, placental perfusate, isolated placental perfusate cells, isolated natural killer cells, e.g., placental natural killer cells, e.g., placenta-derived intermediate natural killer cells, isolated combined natural killer cells, or NK cells described herein, and/or combinations thereof, and optionally IL-2, are added as adjunct treatments or as a combination therapy with said anticancer drug. In certain other embodiments, the individual having multiple myeloma has been treated with at least one anticancer drug, and has relapsed, prior to said administering. In certain embodiments, the individual to be treated has a refractory multiple myeloma. In certain embodiments, the individual to be treated has secondary multiple myeloma. In specific embodiments, the secondary multiple myeloma is treatment-related. In specific embodiments, the secondary multiple myeloma is caused by myelodysplastic syndrome transformation. In certain embodiments, the individual to be treated has had multiple myeloma relapses greater than two months after transplant. In one embodiment, the multiple myeloma treatment method with the cells described herein protects against (e.g., prevents or delays) relapse of multiple myeloma. In one embodiment, the multiple myeloma treatment method described herein results in remission of the a multiple myeloma for 1 month or more, 2, 3, 4, 5, 6, 7, 8, 9, 10, 11, or 12 months or more, 1 year or more, 2 years or more, 3 years or more, or 4 years or more.

In another embodiment, provided herein is a method of treating an individual having multiple myeloma, comprising administering to the individual NK cells, wherein said NK cells are effective to treat multiple myeloma in said individual. In a specific embodiment, said NK cells are cord blood NK cells, or NK cells produced from cord blood hematopoietic cells, e.g., hematopoietic stem cells. In another embodiment, said NK cells have been produced by a three-stage method described herein for producing NK cells. In certain specific embodiments of the method of treating an individual with multiple myeloma, said NK cells are produced by a three-stage method, as described herein. In specific embodiments, the individual is an adult. In certain embodiments, the individual is 65 years old or greater. In specific embodiments, the individual is in first remission. In certain embodiments, said individual has multiple myeloma that has failed at least one non-natural killer cell therapeutic against multiple myeloma. In specific embodiments, said individual is 65 years old or greater, and is in first remission.

In other specific embodiments of the method of treating an individual with multiple myeloma, said NK cells are produced by a method comprising: culturing hematopoietic stem cells or progenitor cells, e.g., CD34$^+$ stem cells or progenitor cells, in a first medium comprising a stem cell mobilizing agent and thrombopoietin (Tpo) to produce a first population of cells, subsequently culturing said first population of cells in a second medium comprising a stem cell mobilizing agent and interleukin-15 (IL-15), and lacking Tpo, to produce a second population of cells, and subsequently culturing said second population of cells in a third medium comprising IL-2 and IL-15, and lacking a stem cell mobilizing agent and LMWH, to produce a third population of cells, wherein the third population of cells comprises natural killer cells that are CD56+, CD3−, CD16− or CD16+, and CD94+ or CD94−, and wherein at least 70%, or at least 80%, of the natural killer cells are viable.

4.9.2. Suppression of Acute Myeloid Leukemia Cell and Multiple Myeloma Cell Proliferation Further provided herein is a method of suppressing the proliferation of acute myeloid leukemia cells, comprising bringing NK cells produced using the methods described herein, e.g., NK cell populations produced using the three-stage method described herein, into proximity with the acute myeloid leukemia cells, e.g., contacting the acute myeloid leukemia cells with NK cells produced using the methods described herein. In certain embodiments, provided herein is a method of suppressing the proliferation of acute myeloid leukemia cells, comprising bringing NK cells produced using the methods described herein, e.g., NK cell populations produced using the three-stage method described herein, into proximity with the acute myeloid leukemia cells, e.g., contacting the acute myeloid leukemia cells with NK cells produced using the methods described herein, further comprising bringing IL-2 into proximity with the NK cells and/or the acute myeloid leukemia cells, e.g., contacting the NK cells and/or acute myeloid leukemia cells with IL-2. In specific embodiments, the IL-2 is rhIL-2.

Further provided herein is a method of suppressing the proliferation of multiple myeloma cells, comprising bringing NK cells produced using the methods described herein, e.g., NK cell populations produced using the three-stage method described herein, into proximity with the multiple myeloma cells, e.g., contacting the multiple myeloma cells with NK cells produced using the methods described herein. In certain embodiments, provided herein is a method of suppressing the proliferation of multiple myeloma cells, comprising bringing NK cells produced using the methods described herein, e.g., NK cell populations produced using the three-stage method described herein, into proximity with the multiple myeloma cells, e.g., contacting the multiple myeloma cells with NK cells produced using the methods described herein, further comprising bringing IL-2 into proximity with the NK cells and/or the multiple myeloma cells, e.g., contacting the NK cells and/or multiple myeloma with IL-2. In specific embodiments, the IL-2 is rhIL-2. In certain embodiments, said individual has received chemotherapy prior to administering said natural killer cells. In specific embodiments, the chemotherapy is an alkylating agent. In more specific embodiments, the alkylating agent is melphalan. In certain embodiments, melphalan is administered according to the label. In certain embodiments, the individual having multiple myeloma is an individual that has received an autologous stem cell transplant before said administering. In certain embodiments, the autologous stem cell transplant was in treatment of said multiple myeloma. In certain embodiments, the stem cells in the autologous stem cell transplant are peripheral blood mononuclear cells.

As used herein, in certain embodiments, "contacting," with respect to cells, in one embodiment encompasses direct physical, e.g., cell-cell, contact between placental perfusate, placental perfusate cells, natural killer cells, e.g., NK cell populations produced according to the three-stage method described herein, and/or isolated combined natural killer cells and the acute myeloid leukemia cells or multiple myeloma cells. In another embodiment, "contacting" encompasses presence in the same physical space, e.g., placental perfusate, placental perfusate cells, natural killer cells, e.g., placental intermediate natural killer cells, natural killer cells described herein, e.g., NK cell populations produced according to the three-stage method described herein, and/or isolated combined natural killer cells are placed in the same container (e.g., culture dish, multiwell plate) as acute myeloid leukemia cells or multiple myeloma cells. In another embodiment, "contacting" placental perfusate, placental perfusate cells, combined natural killer cells, placental intermediate natural killer cells, or natural killer cells described herein, e.g., NK cell populations produced according to the three-stage method described herein, and acute myeloid leukemia cells or multiple myeloma cells is accomplished, e.g., by injecting or infusing the placental perfusate or cells, e.g., placental perfusate cells, combined natural killer cells or natural killer cells, e.g., placental intermediate natural killer cells into an individual, e.g., a human comprising acute myeloid leukemia cells, e.g., a cancer patient. "Contacting," in the context of immunomodulatory compounds and/or thalidomide, means, e.g., that the cells and the immunomodulatory compound and/or thalidomide are directly physically contacted with each other, or are placed within the same physical volume (e.g., a cell culture container or an individual).

As used herein, "therapeutically beneficial" and "therapeutic benefits" include, but are not limited to, e.g., reduction in the size of a tumor; lessening or cessation of expansion of a tumor; reducing or preventing metastatic disease; reduction in the number of cancer cells in a tissue sample, e.g., a blood sample, per unit volume; the clinical improvement in any symptom of the particular cancer or tumor said individual has, the lessening or cessation of worsening of any symptom of the particular cancer the individual has, etc.

4.9.3. Treatment of Acute Myeloid Leukemia or Multiple Myeloma Cells Using NK Cells and IL-2

Treatment of an individual having acute myeloid leukemia using the NK cells produced using the methods described herein, e.g., NK cell populations produced using the three-stage method described herein, can be part of an anticancer therapy regimen that includes administration of IL-2. Treatment of an individual having multiple myeloma using the NK cells produced using the methods described herein, e.g., NK cell populations produced using the three-stage method described herein, can be part of an anticancer therapy regimen that includes administration of IL-2. In certain embodiments, the IL-2 is human IL-2. In certain embodiments, the IL-2 is recombinant human IL-2 (rhIL-2). In certain embodiments, the rhIL-2 is aldesleukin (PROLEUKIN®, Novartis). A non-limiting example of an amino acid sequence of rhIL-2 is provided with GenBank Accession No. NP_000577.2. In certain embodiments, the rhIL-2 has an amino acid sequence that has a 99% sequence identity to GenBank Accession No. NP_000577.2. In certain embodiments, IL-2 is administered in combination with acetaminophen and/or diphenhydramine. In certain embodiments, the NK cells and optional IL-2 are administered after a conditioning regimen. For example, the conditioning regimen can, for example, take place immediately prior to or one, two, three, or four days prior to administration of the NK cells and optional administration of IL-2. In specific embodiments, the conditioning regimen comprises administration of one or more chemotherapies, for example, administration of fludarabine and/or cyclophosphamide. In more specific embodiments, the conditioning regimen comprises treatment with fludarabine and cyclophosphamide. In even more specific embodiments, the conditioning regimen comprises treatment with fludarabine for three, four, five, six, or seven days and cyclophosphamide for one, two, three, or four days.

4.9.4. Administration

Determination of the number of cells, e.g., NK cell populations produced using the three-stage method described herein, and determination of the amount of IL-2, can be performed independently of each other.

Administration of an isolated population of NK cells or a pharmaceutical composition thereof is systemic. In specific embodiments, administration of an isolated population of NK cells or a pharmaceutical composition thereof to a subject is by infusion. In specific embodiments, administration of an isolated population of NK cells or a pharmaceutical composition thereof to a subject is by intravenous (IV) infusion. In certain embodiments, administration of IL-2 or a pharmaceutical composition thereof to a subject is by injection. In specific embodiments, administration of IL-2 or a pharmaceutical composition thereof to a subject is by subcutaneous injection. In certain embodiments, NK cells produced using the methods described herein are administered to a subject in combination with one or more doses of IL-2, for example rhIL-2. In certain embodiments, IL-2 or a pharmaceutical composition thereof is administered to a subject at a dose of 6 million units every other day for a total of 6 doses. In certain embodiments, administration of NK cells is preceded by a conditioning regimen described herein, for example, a conditioning regimen comprising administration of fludarabine and/or cyclophosphamide. In certain embodiments, NK cells produced using the methods described herein are administered to a subject in combination with one or more doses of rhIL-2, wherein administration of NK cells is preceded by a conditioning regimen comprising administration of fludarabine and cyclophosphamide, and wherein administration of each dose rhIL-2 is preceded and followed by administration of acetaminophen and diphenhydramine.

4.9.4.1. Administration of Cells

In certain embodiments, NK cells produced using the methods described herein, e.g., NK cell populations produced using the three-stage method described herein, are used, e.g., administered to an individual, in any amount or number that results in a detectable therapeutic benefit to the individual, e.g., an effective amount, wherein the individual has acute myeloid leukemia, e.g., an acute myeloid leukemia patient. In other embodiments, the individual has multiple myeloma, e.g., a multiple myeloma patient. Such cells can be administered to such an individual by absolute numbers of cells, e.g., said individual can be administered at about, at least about, or at most about, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, or $1 \times 10^{11}$ NK cells produced using the methods described herein. In specific embodiments, said individual is administered at about, at least about, or at most about $3 \times 10^6$, $1 \times 10^7$, $3 \times 10^7$, $1 \times 10^8$, $3 \times 10^8$, or $1 \times 10^9$ NK cells produced using the methods described herein. In specific embodiments, said individual is administered at about, at least about, or at most about $1 \times 10^6$ NK cells produced using the methods described herein. In specific embodiments, said individual is administered at about, at least about, or at most about $3 \times 10^6$ NK cells produced using the methods described herein. In specific embodiments, said individual is administered at about, at least about, or at most about $10 \times 10^6$ NK cells produced using the methods described herein. In specific embodiments, said individual is administered at about, at least about, or at most about $30 \times 10^6$ NK cells produced using the methods described herein. In other embodiments, NK cells produced using the methods described herein can be administered to such an individual by relative numbers of cells, e.g., said individual can be administered at about, at least about, or at most about, $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^{10}$, $1 \times 10^{10}$, $5 \times 10^{10}$, or $1 \times 10^{11}$ NK cells produced using the methods described herein per kilogram of the individual. In specific embodiments, said individual is administered at about, at least about, or at most about $1 \times 10^6$, $3 \times 10^6$, $10 \times 10^6$, or $30 \times 10^6$ NK cells produced using the methods described therein per kilogram of the individual. In other embodiments, NK cells produced using the methods described herein can be administered to such an individual by relative numbers of cells, e.g., said individual can be administered at about, at least about, or at most about, $1 \times 10$, $5 \times 10^5$, $1 \times 10^6$, $5 \times 10^6$, $1 \times 10^7$, $5 \times 10^7$, $1 \times 10^8$, or $5 \times 10^8$ NK cells produced using the methods described herein per kilogram of the individual.

In certain embodiments, the method of suppressing the proliferation of acute myeloid leukemia cells, e.g., in an individual; treatment of an individual having a deficiency in the individual's natural killer cells; or treatment of an individual having acute myeloid leukemia cells, e.g., an individual having acute myeloid leukemia cells, comprises bringing the acute myeloid leukemia cells into proximity with, or administering to said individual, a combination of NK cells produced using the methods described herein and one or more of placental perfusate and/or placental perfusate cells.

In certain embodiments, the method of suppressing the proliferation of multiple myeloma cells, e.g., in an individual; treatment of an individual having a deficiency in the individual's natural killer cells; or treatment of an individual having multiple myeloma cells, e.g., an individual having multiple myeloma cells, comprises bringing the multiple myeloma cells into proximity with, or administering to said individual, a combination of NK cells produced using the methods described herein and one or more of placental perfusate and/or placental perfusate cells.

In another specific embodiment, treatment of an individual having a deficiency in the individual's natural killer cells; treatment of an individual having acute myeloid leukemia; or suppression of acute myeloid leukemia cell proliferation; or suppression of multiple myeloma cell proliferation, is performed using an immunomodulatory compound or thalidomide in combination with NK cells produced using the methods described herein, wherein said cells are supplemented with conditioned medium, e.g., medium conditioned by CD34$^-$, CD10$^+$, CD105$^+$, CD200$^+$ tissue culture plastic-adherent placental cells, e.g., 0.1, 0.2, 0.3, 0.4, 0.5, 0.6, 0.1, 0.8, 0.9, 1, 2, 3, 4, 5, 6, 7, 8, 9, 10 mL of stem cell-conditioned culture medium per unit of perfusate, or per $10^4$, $10^5$, $10^6$, $10^7$, $10^8$, $10^9$, $10^{10}$, or $10^{11}$ NK cells produced using the methods described herein. In certain embodiments, the tissue culture plastic-adherent placental cells are the multipotent adherent placental cells described in U.S. Pat. No. 7,468,276 and U.S. Patent Application Publication No. 2007/0275362, the disclosures of which are incorporated herein by reference in their entireties. In another specific embodiment, the method additionally comprises bringing the tumor cells into proximity with, or administering to the individual, an immunomodulatory compound or thalidomide.

The NK cells produced using the methods described herein and optionally perfusate or perfusate cells, can be administered once to an individual having acute myeloid leukemia, or an individual having acute myeloid leukemia cells, during a course of anticancer therapy; or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10, 24, 36 or more weeks during therapy.

The NK cells produced using the methods described herein and optionally perfusate or perfusate cells, can be administered once to an individual having multiple myeloma, or an individual having multiple myeloma cells, during a course of anticancer therapy; or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10, 24, 36 or more weeks during therapy.

In certain embodiments, NK cells produced using the methods described herein, e.g., NK cell populations produced using the three-stage method described herein, are used, e.g., administered to an individual, in any amount or number that results in a detectable therapeutic benefit to the individual, e.g., an effective amount, wherein the individual has acute myeloid leukemia, e.g., an acute myeloid leukemia patient, or wherein the individual has multiple myeloma, e.g., a multiple myeloma patient.

The NK cells produced using the methods described herein can be administered without regard to whether NK cells produced using the methods described herein have been administered to the individual in the past.

4.9.4.2. Administration of IL-2

In another specific embodiment, treatment of an individual having a deficiency in the individual's natural killer cells; treatment of an individual having acute myeloid leukemia; or suppression of acute myeloid leukemia cell proliferation; or treatment of an individual having multiple myeloma; or suppression of multiple myeloma cell proliferation, said NK cells produced using the methods described herein are supplemented with interleukin-2 (IL-2). In embodiments in which cells and IL-2 are used, the IL-2 and cells can be administered to the individual together, e.g., in the same formulation; separately, e.g., in separate formulations, at approximately the same time; or can be administered separately, e.g., on different dosing schedules or at different times of the day. In certain embodiments, the IL-2 is human IL-2. In certain embodiments, the IL-2 is recombinant human IL-2 (rhIL-2). In certain embodiments, the rhIL-2 is aldesleukin (PROLEUKIN®, Novartis). A non-limiting example of an amino acid sequence of rhIL-2 is provided with GenBank Accession No. NP_000577.2. In certain embodiments, the rhIL-2 has an amino acid sequence that has a 99% sequence identity to GenBank Accession No. NP_000577.2. In certain embodiments, IL-2 units refer to international units.

In embodiments in which cells and IL-2 are used, the IL-2 can be administered subcutaneously. In specific embodiments, the IL-2 can be administered subcutaneously by injection. In more specific embodiments, subcutaneous IL-2 injections are started no earlier than 4 hours after NK cell infusion in the absence of Grade 4 (e.g., Grade 4 according to the National Cancer Institute Common Toxicity Criteria) infusion-related toxicity. In more specific embodiments, subcutaneous IL-2 injections are started within the following 48 hours after NK cell infusion if the subject has experienced Grade 4 (e.g., Grade 4 according to the National Cancer Institute Common Toxicity Criteria) infusion-related toxicity and it resolves to Grade 2 (e.g., Grade 2 according to the National Cancer Institute Common Toxicity Criteria) or better. In certain embodiments, if IL-2 cannot be started within 48 hours after NK cell infusion, no IL-2 will be given.

In certain embodiments, IL-2 or a pharmaceutical composition thereof is administered to a subject at a dose of 6 million units. In certain embodiments, IL-2 or a pharmaceutical composition thereof is administered to a subject at a dose of 3 million, 4 million, 5 million, 6 million, 7 million, 8 million, or 9 million units. In certain embodiments, IL-2 or a pharmaceutical composition thereof is administered to a subject every other day for a total of 6 doses. In certain embodiments, IL-2 or a pharmaceutical composition thereof is administered to a subject every other day for a total of 3, 4, 5, 6, 7, 8, or 9 doses. In certain embodiments, IL-2 or a pharmaceutical composition thereof is administered to a subject every day for a total of 6 doses. In certain embodiments, IL-2 or a pharmaceutical composition thereof is administered to a subject every day for a total of 3, 4, 5, 6, 7, 8, or 9 doses. In certain embodiments, IL-2 or a pharmaceutical composition thereof is administered to a subject every 1, 2, 3, 4, or 5 days for a total of 6 doses. In certain embodiments, IL-2 or a pharmaceutical composition thereof is administered to a subject every week for 6 doses. In certain embodiments, IL-2 or a pharmaceutical composition thereof is administered to a subject every 1, 2, 3, 4, or 5 days for a total of 3, 4, 5, 6, 7, 8, or 9 doses. In certain embodiments, IL-2 or a pharmaceutical composition thereof is administered to a subject every week for a total of 3, 4, 5, 6, 7, 8, or 9 doses. In certain embodiments, IL-2 or a pharmaceutical composition thereof is administered to a subject at a dose of 3 million, 4 million, 5 million, 6 million, 7 million, 8 million, or 9 million units every other day. In certain embodiments, IL-2 or a pharmaceutical composition thereof is administered to a subject at a dose of 3 million, 4 million, 5 million, 6 million, 7 million, 8 million, or 9 million units every other day for a total of 6 doses. In certain embodiments, IL-2 or a pharmaceutical composition thereof is administered to a subject at a dose of 3 million, 4 million, 5 million, 6 million, 7 million, 8 million, or 9 million units every other day for a total of 3, 4, 5, 6, 7, 8, or 9 doses. In certain embodiments, IL-2 or a pharmaceutical composition thereof is administered to a subject at a dose of 6 million units every other day. In certain embodiments, IL-2 or a pharmaceutical composition thereof is administered to a subject at a dose of 6 million units every other day for a total of 3, 4, 5, 6, 7, 8, or 9 doses. In certain embodiments, IL-2 or a pharmaceutical composition thereof is administered to a subject at a dose of 6 million units every 1, 2, 3, 4, or 5 days for a total of 6 doses.

In certain embodiments, IL-2 is administered in combination with acetaminophen. In certain embodiments, IL-2 is administered in combination with diphenhydramine. In specific embodiments, IL-2 is administered in combination with acetaminophen and diphenhydramine. In more specific embodiments, the acetaminophen and diphenhydramine are administered before the IL-2. In more specific embodiments, the acetaminophen and diphenhydramine are administered after the IL-2. In more specific embodiments, the acetaminophen and diphenhydramine are administered before and after the IL-2.

In embodiments in which cells and IL-2 are used, the IL-2 can be administered at a dose of 6 million units every other day for a total of 6 doses. In specific embodiments, for patients weighing less than 45 kilograms, IL-2 is administered at 3 million units/m$^2$ every other day for a total of 6 doses. In specific embodiments, pre-medication with acetaminophen 650 mg PO and diphenhydramine 25 mg PO/IV before and 4 hours after each dose of IL-2 is administered. In more specific embodiments, the development of a new (i.e., not pre-existing) Grade 3 (e.g., Grade 3 according to the National Cancer Institute Common Toxicity Criteria) or higher adverse event of greater than 24 hour duration results in a 50% reduction of the dose of IL-2. In specific embodiments, the Grade 3 (e.g., Grade 3 according to the National Cancer Institute Common Toxicity Criteria) or higher adverse event is selected from the group consisting of the following events: cardiac disorders, investigations (excluding hematological), nervous system disorders, renal and urinary disorders, and respiratory (pulmonary) disorders. In specific embodiments, if the toxicity resolves to Grade 2 (e.g., Grade 2 according to the National Cancer Institute Common Toxicity Criteria) or better within 48 hours, the IL-2 is resumed at a dose reduced by 50% and continued at that reduced dose. In more specific embodiments, if the same toxicity persists, worsens, or recurs, rhIL-2 is permanently discontinued. In specific embodiments, if the toxicity is Grade 4 (e.g., Grade 4 according to the National Cancer Institute Common Toxicity Criteria), the IL-2 is permanently discontinued.

4.9.4.3. Conditioning Regimen

In certain embodiments, a conditioning regimen is administered to a subject prior to treatment with NK cells and optional IL-2. In specific embodiments, the conditioning regimen comprises treatment with fludarabine. In specific embodiments, the conditioning regimen comprises treatment with fludarabine for five days. In specific embodiments, the conditioning regimen comprises treatment with fludarabine for five days, wherein treatment with fludarabine starts 6 days prior to treatment with NK cells and optional IL-2. In specific embodiments, the conditioning regimen comprises treatment with 25 mg/m$^2$ fludarabine for five days. In specific embodiments, the conditioning regimen comprises treatment with 20 to 30 mg/m$^2$ fludarabine for five days. In specific embodiments, the conditioning regimen comprises treatment with 25 mg/m$^2$ fludarabine for five days, wherein treatment with fludarabine starts 6 days prior to treatment with NK cells and optional IL-2. In specific embodiments, the conditioning regimen comprises treatment with 20 to 30 mg/m$^2$ fludarabine for five days, wherein treatment with fludarabine starts 6 days prior to treatment with NK cells and optional IL-2. In specific embodiments, the conditioning regimen comprises treatment with cyclophosphamide. In specific embodiments, the conditioning regimen comprises treatment with cyclophosphamide for 2 days. In specific embodiments, the conditioning regimen comprises treatment with cyclophosphamide for 2 days, wherein treatment with cyclophosphamide starts 5 days prior to treatment with NK cells and optional IL-2. In specific embodiments, the conditioning regimen comprises treatment with 60 mg/kg cyclophosphamide for 2 days. In specific embodiments, the conditioning regimen comprises treatment with 50 to 70 mg/kg cyclophosphamide for 2 days. In specific embodiments, the conditioning regimen comprises treatment with 60 mg/kg cyclophosphamide for 2 days, wherein treatment with cyclophosphamide starts 5 days prior to treatment with NK cells and optional IL-2. In specific embodiments, the conditioning regimen comprises treatment with 50 to 70 mg/kg cyclophosphamide for 2 days, wherein treatment with cyclophosphamide starts 5 days prior to treatment with NK cells and optional IL-2. In specific embodiments, the conditioning regimen comprises treatment with fludarabine and cyclophosphamide. In specific embodiments, the conditioning regimen comprises treatment with fludarabine for five days and cyclophosphamide for two days. In specific embodiments, the conditioning regimen comprises treatment with fludarabine for five days and cyclophosphamide for two days, wherein treatment with fludarabine starts 6 days prior to treatment with NK cells and optional IL-2 and treatment with cyclophosphamide starts 5 days prior to treatment with NK cells and optional IL-2. In specific embodiments, the conditioning regimen comprises treatment with 25 mg/m$^2$ fludarabine for five days and 60 mg/kg cyclophosphamide for two days. In specific embodiments, the conditioning regimen comprises treatment with 20 to 30 mg/m$^2$ fludarabine for five days and 50 to 70 mg/kg cyclophosphamide for two days. In specific embodiments, the conditioning regimen comprises treatment with 25 mg/m$^2$ fludarabine for five days and 60 mg/kg cyclophosphamide for two days, wherein treatment with fludarabine starts 6 days prior to treatment with NK cells and optional IL-2 and treatment with cyclophosphamide starts 5 days prior to treatment with NK cells and optional IL-2. In specific embodiments, the conditioning regimen comprises treatment with 20 to 30 mg/m$^2$ fludarabine for five days and 50 to 70 mg/kg cyclophosphamide for two days, wherein treatment with fludarabine starts 6 days prior to treatment with NK cells and optional IL-2 and treatment with cyclophosphamide starts 5 days prior to treatment with NK cells and optional IL-2.

In specific embodiments, the conditioning regimen comprises treatment with fludarabine for three, four, five, six, or seven days. In specific embodiments, the conditioning regimen comprises treatment with fludarabine for three, four, five, six, or seven days, wherein treatment with fludarabine starts 4, 5, 6, 7, or 8 days prior to treatment with NK cells and optional IL-2. In specific embodiments, the conditioning regimen comprises treatment with 25 mg/m² fludarabine for three, four, five, six, or seven days. In specific embodiments, the conditioning regimen comprises treatment with 20 to 30 mg/m² fludarabine for three, four, five, six, or seven days. In specific embodiments, the conditioning regimen comprises treatment with 25 mg/m² fludarabine for three, four, five, six, or seven days, wherein treatment with fludarabine starts 4, 5, 6, 7, or 8 days prior to treatment with NK cells and optional IL-2. In specific embodiments, the conditioning regimen comprises treatment with 20 to 30 mg/m² fludarabine for three, four, five, six, or seven days, wherein treatment with fludarabine starts 4, 5, 6, 7, or 8 days prior to treatment with NK cells and optional IL-2. In specific embodiments, the conditioning regimen comprises treatment with cyclophosphamide. In specific embodiments, the conditioning regimen comprises treatment with cyclophosphamide for 1, 2, 3, or 4 days. In specific embodiments, the conditioning regimen comprises treatment with cyclophosphamide for 1, 2, 3, or 4 days, wherein treatment with cyclophosphamide starts 4, 5, 6, or 7 days prior to treatment with NK cells and optional IL-2. In specific embodiments, the conditioning regimen comprises treatment with 60 mg/kg cyclophosphamide for 1, 2, 3, or 4 days. In specific embodiments, the conditioning regimen comprises treatment with 50 to 70 mg/kg cyclophosphamide for 1, 2, 3, or 4 days. In specific embodiments, the conditioning regimen comprises treatment with 60 mg/kg cyclophosphamide for 1, 2, 3, or 4 days, wherein treatment with cyclophosphamide starts 4, 5, 6, or 7 days prior to treatment with NK cells and optional IL-2. In specific embodiments, the conditioning regimen comprises treatment with 50 to 70 mg/kg cyclophosphamide for 1, 2, 3, or 4 days, wherein treatment with cyclophosphamide starts 4, 5, 6, or 7 days prior to treatment with NK cells and optional IL-2. In specific embodiments, the conditioning regimen comprises treatment with fludarabine and cyclophosphamide. In specific embodiments, the conditioning regimen comprises treatment with fludarabine for three, four, five, six, or seven days and cyclophosphamide for one, two, three, or four days. In specific embodiments, the conditioning regimen comprises treatment with fludarabine for three, four, five, six, or seven days and cyclophosphamide for one, two, three, or four days, wherein treatment with fludarabine starts 4, 5, 6, 7, or 8 days prior to treatment with NK cells and optional IL-2 and treatment with cyclophosphamide starts 4, 5, 6, or 7 days prior to treatment with NK cells and optional IL-2. In specific embodiments, the conditioning regimen comprises treatment with 25 mg/m² fludarabine for three, four, five, six, or seven days and 60 mg/kg cyclophosphamide for one, two, three, or four days. In specific embodiments, the conditioning regimen comprises treatment with 20 to 30 mg/m² fludarabine for three, four, five, six, or seven days and 50 to 70 mg/kg cyclophosphamide for one, two, three, or four days. In specific embodiments, the conditioning regimen comprises treatment with 25 mg/m² fludarabine for three, four, five, six, or seven days and 60 mg/kg cyclophosphamide for one, two, three, or four days, wherein treatment with fludarabine starts 6 days prior to treatment with NK cells and optional IL-2 and treatment with cyclophosphamide starts 5 days prior to treatment with NK cells and optional IL-2. In specific embodiments, the conditioning regimen comprises treatment with 20 to 30 mg/m² fludarabine for three, four, five, six, or seven days and 50 to 70 mg/kg cyclophosphamide for one, two, three, or four days, wherein treatment with fludarabine starts 4, 5, 6, 7, or 8 days prior to treatment with NK cells and optional IL-2 and treatment with cyclophosphamide starts 4, 5, 6, or 7 days prior to treatment with NK cells and optional IL-2.

5. KITS

Provided herein is a pharmaceutical pack or kit comprising one or more containers filled with one or more of the compositions described herein, e.g., a composition comprising NK cells produced by a method described herein, e.g., NK cell populations produced using the three-stage method described herein. Optionally associated with such container(s) can be a notice in the form prescribed by a governmental agency regulating the manufacture, use or sale of pharmaceuticals or biological products, which notice reflects approval by the agency of manufacture, use or sale for human administration.

The kits encompassed herein can be used in accordance with the methods described herein, e.g., methods of suppressing the growth of acute myeloid leukemia cells and/or methods of treating acute myeloid leukemia or methods of suppressing the growth of multiple myeloma cells and/or methods of treating multiple myeloma. In one embodiment, a kit comprises NK cells produced by a method described herein or a composition thereof, in one or more containers. In a specific embodiment, provided herein is a kit comprising an NK cell population produced by a three-stage method described herein, or a composition thereof. In one embodiment, a kit comprises NK cells produced by a method described herein or a composition thereof, in one or more containers and IL-2 or a composition thereof, in one or more containers. In one embodiment, a kit comprises (i) NK cells produced by a method described herein or a composition thereof, in one or more containers, (ii) IL-2 or a composition thereof, in one or more containers, and (iii) acetaminophen in one or more containers, and/or (iv) diphenhydramine in one or more containers. In one embodiment, a kit comprises (i) NK cells produced by a method described herein or a composition thereof, in one or more containers, (ii) IL-2 or a composition thereof, in one or more containers, and (iii) fludarabine in one or more containers, and/or (iv) cyclophosphamide in one or more containers. In one embodiment, a kit comprises (i) NK cells produced by a method described herein or a composition thereof, in one or more containers, (ii) IL-2 or a composition thereof, in one or more containers, and (iii) acetaminophen in one or more containers, and/or (iv) diphenhydramine in one or more containers, and (v) fludarabine in one or more containers, and/or (vi) cyclophosphamide in one or more containers.

6. EXAMPLES

6.1. Example 1: Clinical Study—Acute Myeloid Leukemia

A Phase I, multicenter, open-label, dose-escalating safety study of human cord blood derived, culture expanded three-stage natural killer cells infusion with subcutaneous recombinant human IL-2 (rhIL-2) is conducted in adults with relapsed and/or refractory acute myeloid leukemia.

The screening/baseline period is defined as the 21 days from day -28 to day -7, before administration of the three-stage NK cells, during which the subjects are evaluated for eligibility. The screening/baseline period is followed by a 5-day conditioning treatment period consisting of cyclophosphamide (60 mg/kg×2 days on days -5 and -4, except that if less than 4 months from the prior transplant, omit the day -4 dose of cyclophosphamide), and fludarabine (25 mg/m$^2$×5 days starting day -6) (study days -6 to -2). The second day of fludarabine is omitted if less than four months has passed from a prior transplant.

During the treatment period, subjects are pre-medicated with acetaminophen 650 mg PO and diphenhydramine 25 mg PO/IV within 60 minutes prior to three-stage NK cells infusion and approximately 4 hours after three-stage NK cells infusion. The three-stage NK cells infusion is administered IV on Day 0. No sooner than 4 hours after the end of infusion, and in the absence of any Grade 4 (according to the National Cancer Institute Common Toxicity Criteria) infusion-related toxicity, 6 million units of rhIL-2 is injected subcutaneously (SC) according to instructions. The rhIL-2 injection is then repeated every other day for a total of 6 injections beginning with Day 0. Acetaminophen 650 mg PO and diphenhydramine 25 mg PO is recommended to be used as a pre-medication prior to each rhIL-2 injection and as post-medication after reach rhIL-2 injection.

The timing of these pre- and post-medications is at the discretion of the investigator or according to the site's protocol. Meperidine may also be administered to control rigors, if clinically indicated.

The study utilizes a 3+3 dose escalation design with 3 to 6 subjects enrolled into each of 4 dose cohorts ($1\times10^6$ cells/kg, $3\times10^6$ cells/kg, $10\times10^6$ cells/kg, and $30\times10^6$ cells/kg), and 4 additional subjects added to the maximum tolerated dose (MTD).

Initially, three subjects are enrolled to receive a single infusion of $1\times10^6$ cells/kg. Subjects are assigned to a dose cohort based on the order of entry into the study. Four three-stage NK cell dose levels are planned in this study:

Dose Level 1: $1\times10^6$ cells/kg administered on study day 0.

Dose Level 2: $3\times10^6$ cells/kg administered on study day 0.

Dose Level 3: $10\times10^6$ cells/kg administered on study day 0.

Dose Level 4: $30\times10^6$ cells/kg administered on study day 0.

The primary outcome measures are to assess dose-limiting toxicity (DLT), the number and severity of adverse events within 28 days of administration, and MTD, the maximum dose safely administered for the treatment of patients with AML. The time frame for the primary outcome measures is up to approximately 28 days. The number of adverse events is determined for up to approximately 12 months.

The secondary outcome measures are complete remission with incomplete platelet recovery (CRp) and complete remission (CR). CRp is defined as leukemia clearance (<5% marrow blasts and no circulating peripheral blasts) and neutrophil recovery but with incomplete platelet recovery. CR is defined as leukemia clearance ((<5% marrow blasts and no circulating peripheral blasts) in conjunction with normal values for absolute neutrophil count (>1000/μL) and platelet count (>100,000/μL) and independence from red cell transfusion. The time frame for secondary outcome measures is up to approximately 42 days.

Subject must have an eligible disease to be enrolled in the study, as follows:
Primary acute myeloid leukemia induction failure: no CR after 2 or more induction attempts; or
Relapsed acute myeloid leukemia: not in CR after 1 or more cycles of standard re-induction chemotherapy. For relapsed subjects greater than 60 years of age, the 1 cycle of standard re-induction chemotherapy is not required if either of the following criteria is met: a relapse within 6 months of last chemotherapy; or a blast count <30% within 10 days of starting this protocol therapy; or
Secondary acute myeloid leukemia (MDS transformation or treatment related); or
Acute myeloid leukemia relapses >2 months after transplant subjects with prior central nervous system involvement are eligible provided that it has been treated and cerebrospinal fluid is clear for at least two weeks prior to visit 1.

6.2. Example 2: Clinical Study—Multiple Myeloma

A Phase I, multicenter, open-label, safety study of human cord blood derived, culture expanded three-stage natural killer cells infusion with subcutaneous recombinant human IL-2 (rhIL-2) following autologous stem cell transplant (ASCT) is conducted in adults with multiple myeloma (MM).

The primary objective of the study is to assess safety and determine the maximum tolerated dose of the three-stage NK cells in subjects with MM following ASCT. The secondary objective is to explore the potential clinical efficacy by day 100.

The maximum tolerated dose for the three-stage natural killer cells is evaluated at Day 2 and Day 7 post-ASCT, and is identified at Day 14 post-ASCT. Administration of the three-stage natural killer cells is intravenous, and followed by a total of six IL-2 injections to support the NK cells in the body.

Primary outcome measures are adverse events and dose limiting toxicity, both with a time frame of up to 28 days. The secondary outcome measure is response rate, with a time frame of up to 100 days, wherein response includes minimum residual disease.

The study protocol is as follows: first, melphalan is administered, followed by ASCT (Day -5 to Day 0), followed by administration of three-stage natural killer cells at up to 3 varying dose levels followed by rhIL-2 every other day, from day 0 to day 13.

EQUIVALENTS

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes. The citation of any publication is for its disclosure prior to the filing date and should not be construed as an admission that the present invention is not entitled to antedate such publication by virtue of prior invention.

What is claimed is:

1. A method of treating an individual having acute myeloid leukemia by administering an effective amount of a cell population comprising natural killer cells, wherein the cell population comprising natural killer cells is produced by a method comprising the steps of:
   (a) culturing hematopoietic stem or progenitor cells in a first medium comprising a stem cell mobilizing agent and thrombopoietin (Tpo) to produce a first population of cells;
   (b) culturing the first population of cells in a second medium comprising a stem cell mobilizing agent and interleukin-15 (IL-15), and lacking Tpo, to produce a second population of cells; and
   (c) culturing the second population of cells in a third medium comprising IL-2 and IL-15, and lacking a stem cell mobilizing agent and low-molecular weight heparin (LMWH), to produce a third population of cells;
   wherein said stem cell mobilizing agent is an aryl hydrocarbon receptor inhibitor, wherein the third population of cells comprises natural killer cells that are CD56+, CD3−, CD16− or CD16+, and CD94+ or CD94−, wherein at least 80% of the natural killer cells are viable; and
   wherein the method of treatment additionally comprises administering to the patient an effective amount of IL-2.

2. The method of claim 1, wherein said hematopoietic stem cells are CD34+ hematopoietic stem cells, or wherein said hematopoietic stem cells are placental hematopoietic stem cells.

3. The method of claim 2, wherein said placental hematopoietic stem cells are obtained from, or obtainable from, human placental perfusate, or wherein said placental hematopoietic stem cells are obtained from, or obtainable from, nucleated cells isolated from human placental perfusate.

4. The method of claim 1, wherein said aryl hydrocarbon receptor inhibitor is StemRegenin-1 (SR-1) (4-(2-(2-(benzo[b]thiophen-3-yl)-9-isopropyl-9H-purin-6-ylamino)ethyl)phenol), wherein said aryl hydrocarbon receptor inhibitor is resveratrol, wherein said aryl hydrocarbon receptor inhibitor is the compound CH223191 (1-Methyl-N-[2-methyl-4-[2-(2-methylphenyl)diazenyl]phenyl-1H-pyrazole-5-carboxamide].

5. The method of claim 1, wherein said first medium additionally comprises one or more of Low Molecular Weight Heparin (LMWH), Flt-3 Ligand (Flt-3L), stem cell factor (SCF), IL-6, IL-7, granulocyte colony-stimulating factor (G-CSF), or granulocyte-macrophage-stimulating factor (GM-CSF), or wherein said first medium comprises each of LMWH, Flt-3L, SCF, IL-6, IL-7, G-CSF, and GM-CSF.

6. The method of claim 5, wherein said LMWH, Flt-3, SCF, IL-6, IL-7, G-CSF, and/or GM-CSF are not comprised within an undefined component of the first medium, second medium or third medium, or wherein said LMWH, Flt-3, SCF, IL-6, IL-7, G-CSF, and/or GM-CSF are not comprised within serum.

7. The method of claim 1, wherein said second medium additionally comprises one or more of LMWH, Flt-3, SCF, IL-6, IL-7, G-CSF, and GM-CSF, or wherein said second medium additionally comprises each of LMWH, Flt-3, SCF, IL-6, IL-7, G-CSF, and GM-CSF.

8. The method of claim 1, wherein said third medium additionally comprises one or more of SCF, IL-6, IL-7, G-CSF, or GM-CSF, or wherein said third medium comprises each of SCF, IL-6, G-CSF, and GM-CSF.

9. The method of claim 1, wherein any of said first medium, second medium or third medium comprises human serum-AB, wherein any of said first medium, second medium or third medium comprises 2-mercaptoethanol, or wherein any of said first medium, second medium or third medium comprises gentamycin.

10. The method of claim 1, wherein said method comprises culturing the hematopoietic stem cells in the first medium for 7-13 days, wherein said method comprises culturing the hematopoietic stem cells in the first medium for 8-12 days, or wherein said method comprises culturing the hematopoietic stem cells in the first medium for about 10 days.

11. The method of claim 1, wherein said method comprises culturing said first population of cells in said second medium for 2-6 days, wherein said method comprises culturing said first population of cells in said second medium for 3-5 days, or wherein said method comprises culturing said first population of cells in said second medium for about 4 days.

12. The method of claim 1, wherein said method comprises culturing said second population of cells in said third medium for 10-30 days, wherein said method comprises culturing said second population of cells in said third medium for 15-25 days, or wherein said method comprises culturing said second population of cells in said third medium for about 21 days.

13. The method of claim 1, wherein said method produces natural killer cells that comprise at least 20% CD56+CD3− natural killer cells, wherein said method produces natural killer cells that comprise at least 40% CD56+CD3− natural killer cells, wherein said method produces natural killer cells that comprise at least 60% CD56+CD3−natural killer cells, or wherein said method produces natural killer cells that comprise at least 80% CD56+CD3− natural killer cells.

14. The method of claim 1, additionally comprising cryopreserving said population of cells after step (c), additionally comprising cryopreserving said natural killer cells after step (c), or wherein said natural killer cells have been cryopreserved prior to said contacting or said administering.

15. The method of claim 1, wherein said individual is administered about $1 \times 10^6$, $3 \times 10^6$, $10 \times 10^6$, or $30 \times 10^6$ natural killer cells per kilogram of the individual.

16. A method of treating an individual having multiple myeloma by administering an effective amount of a cell population comprising natural killer cells, wherein the cell population comprising natural killer cells is produced by a method comprising the steps of:
   (a) culturing hematopoietic stem or progenitor cells in a first medium comprising a stem cell mobilizing agent and thrombopoietin (Tpo) to produce a first population of cells;
   (b) culturing the first population of cells in a second medium comprising a stem cell mobilizing agent and interleukin-15 (IL-15), and lacking Tpo, to produce a second population of cells; and
   (c) culturing the second population of cells in a third medium comprising IL-2 and IL-15, and lacking a stem cell mobilizing agent and LMWH, to produce a third population of cells;
   wherein said stem cell mobilizing agent is an aryl hydrocarbon receptor inhibitor, wherein the third population of cells comprises natural killer cells that are CD56±, CD3−, CD16− or CD16+, and CD94+ or CD94−, wherein at least 80% of the natural killer cells are viable; and wherein the method of treatment additionally comprises administering to the patient an effective amount of IL-2.

17. A method of suppressing the proliferation of multiple myeloma cells comprising contacting the multiple myeloma cells with a plurality of natural killer cells, wherein the natural killer cells are by a method comprising the steps of:
(a) culturing hematopoietic stem or progenitor cells in a first medium comprising a stem cell mobilizing agent and thrombopoietin (Tpo) to produce a first population of cells;
(b) culturing the first population of cells in a second medium comprising a stem cell mobilizing agent and interleukin-15 (IL-15); and lacking Tpo, to produce a second population of cells; and
(c) culturing the second population of cells in a third medium comprising IL-2 and IL-15, and lacking a stem cell mobilizing agent and LMWH, to produce a third population of cells;
wherein said stein cell mobilizing agent is an aryl hydrocarbon receptor inhibitor, wherein the third population of cells comprises natural killer cells that are CD56+, CD3—, CD16− or CD16+, and CD94+ or CD94−, wherein at least 80% of the natural killer cells are viable; and
wherein said method of suppressing additionally comprises contacting the multiple myeloma cells with IL-2.

18. The method of claim 17, wherein said natural killer cells have been cryopreserved prior to said contacting or said administering.

* * * * *